US008030464B2

(12) United States Patent
Altman

(10) Patent No.: US 8,030,464 B2
(45) Date of Patent: Oct. 4, 2011

(54) STABILIZED BIOACTIVE PEPTIDES AND METHODS OF IDENTIFICATION, SYNTHESIS, AND USE

(75) Inventor: Elliot Altman, Athens, GA (US)

(73) Assignee: The University of Georgia Research Foundation, Inc, Athens, GA (US)

( * ) Notice: Subject to any disclaimer, the term of this patent is extended or adjusted under 35 U.S.C. 154(b) by 273 days.

(21) Appl. No.: 12/074,357

(22) Filed: Mar. 3, 2008

(65) Prior Publication Data
US 2009/0004696 A1 Jan. 1, 2009

Related U.S. Application Data

(63) Continuation of application No. 11/213,668, filed on Aug. 26, 2005, now Pat. No. 7,365,162, which is a continuation of application No. 10/210,023, filed on Jul. 31, 2002, now abandoned, and a continuation-in-part of application No. 09/701,947, filed as application No. PCT/US99/23731 on Oct. 12, 1999, now Pat. No. 6,818,611.

(60) Provisional application No. 60/104,013, filed on Oct. 13, 1998, provisional application No. 60/112,150, filed on Dec. 14, 1998.

(51) Int. Cl.
C07H 21/02 (2006.01)
A61K 38/00 (2006.01)
(52) U.S. Cl. ............ 536/23.1; 435/320.1; 435/69.1; 435/69.2; 530/42; 530/300; 514/2
(58) Field of Classification Search .......... None
See application file for complete search history.

(56) References Cited

U.S. PATENT DOCUMENTS

| 4,711,847 A | 12/1987 | Konig et al. |
| 4,725,535 A * | 2/1988 | Sonenshein et al. ........... 435/6 |
| 4,732,864 A | 3/1988 | Tolman |
| 4,987,070 A | 1/1991 | Magota et al. |
| 5,049,545 A * | 9/1991 | Lobermann et al. ......... 514/5.9 |
| 5,093,241 A | 3/1992 | Bennett et al. |
| 5,175,101 A * | 12/1992 | Gotz et al. .................. 435/6 |
| 5,187,261 A | 2/1993 | Latta et al. |
| 5,212,083 A | 5/1993 | Haldenwang |
| 5,270,181 A | 12/1993 | McCoy et al. |
| 5,292,646 A | 3/1994 | McCoy et al. |
| 5,302,519 A | 4/1994 | Blackwood et al. |
| 5,380,712 A | 1/1995 | Ballance et al. |
| 5,427,927 A | 6/1995 | Meyer et al. |
| 5,445,954 A | 8/1995 | Huang et al. |
| 5,589,364 A | 12/1996 | Williams et al. |
| 5,633,229 A | 5/1997 | Kokryakov et al. |
| 5,635,182 A * | 6/1997 | McCoy et al. ............. 424/192.1 |
| 5,646,016 A | 7/1997 | McCoy et al. |
| 5,654,451 A | 8/1997 | Kari |
| 5,665,863 A | 9/1997 | Yeh |
| 5,677,172 A | 10/1997 | Makarow |
| 5,741,646 A | 4/1998 | Sherley et al. |
| 5,759,802 A | 6/1998 | Maki et al. |
| 5,766,883 A | 6/1998 | Ballance et al. |
| 5,792,831 A | 8/1998 | Maloy |
| 5,804,553 A | 9/1998 | Kokryakov et al. |
| 5,807,746 A | 9/1998 | Lin et al. |
| 5,888,763 A | 3/1999 | Hanafusa et al. |
| 6,057,129 A | 5/2000 | Young et al. |
| 6,143,524 A | 11/2000 | McCoy et al. |
| 6,165,470 A | 12/2000 | Becquart et al. |
| 6,180,343 B1 | 1/2001 | Anderson et al. |
| 6,329,209 B1 | 12/2001 | Wagner et al. |
| 6,548,632 B1 | 4/2003 | Anderson et al. |
| 6,562,617 B1 | 5/2003 | Anderson et al. |
| 6,566,498 B1 | 5/2003 | Ni, Jr. et al. |
| 6,630,197 B1 | 10/2003 | Wood et al. |
| 6,686,179 B2 | 2/2004 | Fleer et al. |
| 6,818,611 B1 | 11/2004 | Altman |
| 7,365,162 B2 | 4/2008 | Altman et al. |
| 2001/0034333 A1 * | 10/2001 | Kosak ....................... 514/44 |
| 2001/0056075 A1 | 12/2001 | Gyuris et al. |
| 2003/0190740 A1 | 10/2003 | Altman |
| 2004/0235091 A1 | 11/2004 | Altman |
| 2007/0099262 A1 | 5/2007 | Anderson et al. |

FOREIGN PATENT DOCUMENTS
WO    WO 90/07862    7/1990
(Continued)

OTHER PUBLICATIONS

Tagami et al. (1995) Role of CRP in transcription activation at Escherichia coli lac promoter: CRP is dispensable after the formation of open complex, Nucleic acids Res., 23, No. 4, pp. 599-605.*
Saida et al. (2006) Expression of highly toxic genes in E. coli: special strategies and genetic tool, Curr. Protein Pept. Sci., vol. 7, No. 1, pp. 47-56.*
Kentsis et al. (2004) Unfolded state of polyalanine is a segmented polyproline II helix, Proteins, vol. 55, No. 3, pp. 493-501.*
Fasman (ed.), Prediction of Protein Structure and the Principles of Protein Conformation. Plenum Press, New York, NY; 1989. Title page, publisher's page, and table of contents only; 5 pages.
McTigue et al., "Crystal structures of a schistosomal drug and vaccine target: Glutathione S-transferase from Schistosoma japanica and its complex with the leading antischistosomal drug Praziquantel," 1995 J. Mol. Biol. 246:21-27.
Tang and Dill, "Native protein fluctuations: The conformational-motion temperature and the inverse correlation of protein flexibility with protein stability, " 1998 J. Biomol. Struct. Dynam. 16(2):397-411.
"Structural Classification of Proteins" [online]. 1.73 release (Nov. 2007) Available on the Internet since 1994 [retrieved on Jan. 19, 2009]. Retrieved from //scop.mrc-lmb.cam.ac.uk/scop/; 3 pages.

(Continued)

Primary Examiner — Anand Desai
Assistant Examiner — Samuel Liu
(74) Attorney, Agent, or Firm — Mueting, Raasch & Gebhardt, P.A.

(57) ABSTRACT

An intracellular selection system allows screening for peptide bioactivity and stability. Randomized recombinant peptides are screened for bioactivity in a tightly regulated expression system, preferably derived from the wild-type lac operon. Bioactive peptides thus identified are inherently protease- and peptidase-resistant. Also provided are bioactive peptides stabilized by a stabilizing group at the N-terminus, the C-terminus, or both. The stabilizing group can be a small stable protein, such as the Rop protein, glutathione sulfotransferase, thioredoxin, maltose binding protein, or glutathione reductase, an α-helical moiety, or one or more proline residues.

22 Claims, 9 Drawing Sheets

FOREIGN PATENT DOCUMENTS

| WO | WO 91/01743 | | 2/1991 |
|---|---|---|---|
| WO | WO 92/07071 | | 4/1992 |
| WO | WO 93/03156 | | 2/1993 |
| WO | WO 93/23544 | | 11/1993 |
| WO | WO 96/40721 | | 12/1996 |
| WO | WO 97/04110 | | 2/1997 |
| WO | WO 97/29127 | | 8/1997 |
| WO | WO 98/22141 | A2 | 5/1998 |
| WO | WO 98/22141 | A3 | 1/1999 |
| WO | WO 99/35494 | A1 | 7/1999 |
| WO | WO 99/36554 | A1 | 7/1999 |
| WO | WO 99/53079 | A1 | 10/1999 |
| WO | WO 00/22112 | A1 | 4/2000 |
| WO | WO 01/45746 | A2 | 6/2001 |
| WO | WO 01/45746 | A3 | 10/2001 |
| WO | WO 01/77137 | A1 | 10/2001 |
| WO | WO 01/79258 | A1 | 10/2001 |
| WO | WO 01/79442 | A2 | 10/2001 |
| WO | WO 01/79443 | A2 | 10/2001 |
| WO | WO 01/79444 | A2 | 10/2001 |
| WO | WO 01/79480 | A1 | 10/2001 |
| WO | WO 01/79443 | A3 | 2/2002 |
| WO | WO 01/79444 | A3 | 5/2002 |
| WO | WO 01/79442 | A3 | 6/2002 |
| WO | WO 2004/011485 | A2 | 2/2004 |
| WO | WO 2004/011485 | A3 | 4/2005 |

OTHER PUBLICATIONS

Agerberth et al., "Amino Acid Sequence of PR-39, Isolation from Pig Intestine of a New Member of the Family of Proline-arginine-rich Antibacterial Peptides," 1991. *Eur J Biochem.*, 202(3):849-854.

Altman et al., "Characterization of Region in Mature LamB Protein That Interacts with a Component of the Export Machinery of *Escherichia coli*", 1990. *J. Biol. Chem.*, 265(30):18148-18153.

Amann et al., "'ATG vectors' for regulated high-level expression of cloned genes in *Escherichia coli*", 1985. Gene, 40:183-190.

Amann et al., "Tightly regulated *tac* promoter vectors useful for the expression of unfused and fused proteins in *Escherichia coli*", 1988. *Gene*, 69-301-315.

Ast et al., "A rapid and sensitive bacterial assay to determine the inhibitory effect of 'interface' peptides on HIV-1 protease co-expressed in *Escherichia coli*," 1998. *J. Virological Methods*, 71:77-85.

Bai et al., "Structural Specificity of Mucosal-Cell Transport and Metabolism of Peptide Drugs: Implication for Oral Peptide Drug Delivery", 1992. *Pharmaceutical Res.*, 9(8):969-978.

Bai et al., "Targeting of Peptide and Protein Drugs to Specific Sites in the Oral Route", 1995. *Crit. Rev. Ther. Drug Carrier Systems*, 12(4):339-371.

Balbás et al., "Plasmid vector pBR322 and its special-purpose derivatives—a review", 1986. *Gene*, 50:3-40.

Banner et al., "Structure of the ColE1 Rop Protein at 1.7 Å Resolution," 1987. *J. Mol. Biol.*, 196:657-675.

Barling et al., "Indirect [$^3$H] Methyl Exchange as a General Method for Labeling Methionine Residues: Application to Calcitonin," 1985. *Analytical Biochemistry*, 144(2):542-552.

Bechinger et al., "Structure and orientation of the antibiotic peptide magainin in membranes by solid-state nuclear magnetic resonance spectroscopy," 1993. *Protein Science*, 2:2077-2084.

Bedarkar et al., "Polypeptide hormone-receptor interactions: the structure and receptor binding of insulin and glucagon," 1978. *Molecular Interactions and Activity in Proteins: Ciba Foundation Symposium*, Excerpta Medica, Amsterdam, 60:105-121.

Beremand et al., "Synthesis, Cloning, and Expression in *Escherichia coli* of a Spinach Acyl Carrier Protein-1 Gene", 1987. *Arch. Biochem. Biophys.*, 256(1):90-100.

Betz et al., "*De Novo* Design of Native Proteins: Characterization of Proteins Intended to Fold into Antiparallel, Rop-like, Four-Helix Bundles," 1997. *Biochemistry*, 36:2450-2458.

Blanc et al., "Examination of the Requirement for an Amphiphilic Helical Structure in β-Endorphin through the Design, Synthesis, and Study of Model Peptides," *J. Biol. Chem.*, 258(13):8277-8284.

Bolivar et al., "Construction and Characterization of New Cloning Vehicles", 1977. *Gene*, 2:95-113.

Brosius et al., "Regulation of ribosomal RNA promoters with a synthetic *lac* operator," 1984. *Proc. Nat'l. Acad. Sci. USA*, 81:6929-6933.

Brown et al., "lac repressor can regulate expression from a hybrid SV40 early promotor containing a lac operator in animal cells," 1987. *Cell*, 49(5):603-12.

Brownlees et al., "Peptidases, Peptides, and the Mammalian Blood-Brain Barrier", 1993. *J. Neurochem.*, 60(3):793-803.

Bryson et al., "Protein Design: A Hierarchic Approach," 1995. *Science*, 270:935-941.

Cachia et al., "Calmodulin and Troponin C: A Comparative Study of the Interaction of Mastoparan and Troponin I Inhibitory Peptide [104-115]," 1986. *Biochemistry*, 25:3553-3562.

Carmona et al., "Conformational Structure of bombesin as studied by vibrational and circular dichroism spectroscopy," 1995. *Biochim. Biophys. Acta*, 1246:128-134.

Casadaban et al., "Analysis of Gene Control Signals by DNA Fusion and Cloning in *Escherichia coli*", 1980. *J. Mol. Biol.*, 138:179-207.

Cesareni et al., "Control of ColE1 DNA replication: The *rop* gene product negatively affects transcription from the replication primer promoter", 1982. *Proc. Nat'l Acad. Sci. USA*, 79:6313-6317.

Chou et al., "Prediction of the Secondary Structure of Proteins from Their Amino Acid Sequence", 1978. *Adv. Enzymol.*, 47:45-148.

Chou, "Prediction of Protein Structural Classes from Amino Acid Compositions", 1989. *Prediction of Protein Structure and the Principles of Protein Conformation*, Fasman, G.D. ed., Plenum Press, New York, N.Y., pp. 549-586 (1989).

Colas et al., "Genetic selection of peptide aptamers that recognize and inhibit cyclin-dependent kinase 2," 1996. *Nature*, 380:548-550.

Creighton, *Proteins—Structures and Molecular Properties*, W.H. Freeman and Company, N.Y., pp. 182-186 (1993).

Cunningham et al., "Proline Specific Peptidases," 1997. *Biochi. Biophy. Acta*, 1343:160-186.

Cwirla et al., "Peptides on phage: A vast library of peptides for identifying ligands", 1990. *Proc. Nat'l. Acad. Sci. USA*, 87:6378-6382.

Devlin et al., "Random Peptide Libraries: A Source of Specific Protein Binding Molecules", 1990. *Science*, 249:404-406.

Eberle et al., "Proton Nuclear Magnetic Resonance Assignments and Secondary Structure Determination of the col. E1 rop (rom) Protein", 1990. *Biochemistry*, 29:7402-7407.

Egleton et al., "Bioavailability and Transport of Peptides and Peptide Drugs into the Brain", 1997. *Peptides*, 18(9):1431-1439.

Eichler et al. "Peptide, Peptidomimetic, and Organic Synthetic Combinatorial Libraries", 1995. *Medicinal Research Reviews*, 15(6):481-496.

Eren et al., "Chemical Synthesis and Expression of a Synthetic Gene for the Flavodoxin from *Clostridium* MP", 1989. *J. Biol. Chem.*, 264(25):14874-14879.

Fabbrizio et al., "Inhibition of mammalian cell proliferation by genetically selected peptide aptamers that functionally antagonize E2F activity," 1999. *Oncogene*, 18:4357-4363.

Favrin et al., "Folding of a small helical protein using hydrogen bonds and hydrophobicity forces," 2002 *Proteins* 47(2):99-105.

Fezoui et al., "*De novo* design and structural characterization of an α-helical hairpin peptide: A model system for the study of protein folding intermediates," 1994. *Proc. Natl. Acad. Sci. USA*, 91:3675-3679.

Fong et al., "Necessity of the Disulfide Bond of Vasopressin for Antidiuretic Activity," 1964. *Biochem. Biophys. Res. Comm.*, 14(3):302-306.

Frank et al., "Amino Acid Sequences of Two Proline-rich Bactenecins. Antimicrobial Peptides of Bovine Neutrophils," 1990. *J. Biol. Chem.*, 265(31):18871-18874.

Garnier et al., "Analysis of the Accuracy and Implications of Simple Methods for Predicting the Secondary Structure of Globular Proteins" 1978. *J. Mol. Biol.*, 120:97-120.

Geyer et al., "Chapter 13: Selection of Genetic Agents from Random Peptide Aptamer Expression Libraries," 2000. *Methods in Enzymology*, Academic Press, 171-208.

Ghosh et al., "cDNA Cloning, Expression, and Rapid Purification of a Kunitz-Type Winged Bean Chymotrypsin Inhibitor", 1997.*Protein Expression and Purification*, 10:100-106.

Giza et al., "A Self-inducing Runaway-replication Plasmid Expression System Utilizing the Rop Protein," 1989. *Gene*, 78(1):73-84.

Godson, "An over-expression plasmid for *Escherichia coli* primase", 1991. *Gene*, 100:59-64.

Grâna et al., "The Effects of Mutations in the *ant* Promoter of Phage P22 Depend on Context", 1988. *Genetics*, 120:319-327.

Gronenborn et al., "A $^1$H-NMR study of the solution conformation of secretin," 1987. *FEBS Letters*, 215(1):88-94.

Grosjean et al., "Preferential codon usage in prokaryotic genes: the optimal codon-anticodon interaction energy and the selective codon usage in efficiently expressed genes", 1982. *Gene*, 18:199-209.

Guyer et al., Identification of a Sex-factor-affinity Site in *E. coli* as γδ, 1980. *Cold Spring Harbor Symp. Quant. Biol.*, 45:135-140.

Gyuris et al., "Cdi1, a Human G1 and S Phase Protein Phosphatase That Associates with Cdk2," 1993. *Cell*, 75:791-803.

Heitz et al., "$^1$H 2D NMR and Distance Geometry Study of the Folding of *Ecballium elaterium* Trypsin Inhibitor, a Member of the Squash Inhibitors Family," 1989; *Biochemistry*, 28:2392-2398.

Ikemura, "Correlation between the Abundance of *Escherichia coli* Transfer RNAs and the Occurrence of the Respective Codons in its Protein Genes: A Proposal for a Synonymous Codon Choice that is Optimal for the *E. coli* Translational System", 1981. *J. Mol. Biol.*, 151:389-409.

Itakura et al., "Expression in *Escherichia coli* of a Chemically Synthesized Gene for the Hormone Somatostatin", 1977. *Science*, 198:1056-1063.

Kaplan et al., "Conformational stability of pGEX-expressed Schistosoma japonicum glutathione S-transferase: a detoxification enzyme and fusion-protein affinity tag," 1997. *Protein Sci.*, 6(2):399-406.

Katz et al., "Targeting of retroviral integrase by fusion to a heterologous DNA binding domain: in vitro activities and incorporation of a fusion protein into viral particles," 1996 *Virology* 217:178-190.

Khan et al., "Sequence-Specific $^1$H NMR Assignments and Secondary Structure of Porcine Motilin," 1990. *Biochemistry*, 29:5743-5751.

Klein et al., "The detection and classification of membrane-spanning proteins", 1985. *Biochim. Biophys. Acta*, 815:468-476.

Kresse et al., "Four-helix bundle topology re-engineered: monomeric Rop protein variants with different loop arrangements," 2001. *Protein Eng.*, 14:897-901.

Lah et al., "Phage surface presentation and secretion of antibody fragments using an adaptable phagemid vector," 1994. *Hum Antibodies Hybridomas* 5(1-2):48-56.

Lam, "Application of combinatorial library methods in cancer research and drug discovery", 1997. *Anti-Cancer Drug Design*, 12:145-167.

Lanzer et al., "Promoters largely determine the efficiency of repressor action," 1988. *Proc. Natl. Acad Sci. USA*, 85(23):8973-8977.

LaVallie et al., "A Thioredoxin Gene Fusion Expression System That Circumvents Inclusion Body Formation in the *E. coli* Cytoplasm," 1993. *BioTechnology*, 11(2):187-193.

Lebl et al., "Synthetic Peptide Libraries", 1997. *Meth. Enzymol.*, 289:336-392.

Lehrer et al., "Neutrophils and Host Defense," 1988. *Am. Intern. Med.*, 109(2):127-142.

Lin-Chao et al., "High copy number of the pUC plasmid results from a Rom/Rop-suppressible point mutation in RNA II", 1992. *Mol. Microbiol.*, 6(22):3385-3393.

Linden et al., "The glycan domain of thrombopoietin enhances its secretion," 2000. *Biochemistry*. 39:3044-3051.

Lowenadler et al., "Production of specific antibodies against protein A fusion proteins," 1986 *EMBO Journal* 5(9):2393-2398.

Lowman, "Bacteriophage Display and Discovery of Peptide Leads For Drug Development", 1997. *Annu. Rev. Biophys. Biomol. Struct.*, 26:401-424.

Lu et al., "Expression of Thioredoxin Random Peptide Libraries on the *Escherichia coli* Cell Surface as Functional Fusions to Flagellin: A System Designed for Exploring Protein-Protein Interactions," 1995. *Bio/Technology*. 13:366-372.

MacKerell, Jr., "Molecular modeling dynamics of neuropeptide," 1988 *J. Comput. Aided Mol. Des.* 2(1):55-63.

Makrides et al., "Extended in Vivo Half-Life of human soluble complement receptor type 1 fused to a serum Albumin-binding receptor," 1996, *J. Pharmacology and Experimental Therapeutics*. 277(1 ):534-542.

Miller, "Experiments in Molecular Genetics", 1972. Cold Spring Harbor Laboratoiy, Cold Spring Harbor, N.Y., Title Page and Table of Contents.

Miller et al., "An *E. coli* Gene Product Required for λ Site-Specific Recombination" 1980. *Cell*, 20:711-719.

Miller et. al., "Interior and Surface of Monomeric Proteins" 1987. *Mol. Biol*. 196:641-656.

Miller, "Protein Degradation and Proteolytic Modification", *Escherichia coli and Salmonella*, Cellular and Molecular Biology, 1996. 2nd Edition (Neidhardt, F.C. ed.), ASM Press, Washington, D.C., vol. 1:938-954.

Misono et al., "Rat Atrial Natriuretic Factor: Complete Amino Acid Sequence and Disulfide Linkage Essential for Biological Activity," 1984. *Biochem. Biophys. Res. Comm.*, 119(2):524-529.

Mor et al., "Structure, Synthesis, and Activity of Dermaseptin *b*, a Novel Vertebrate Defensive Peptide from Frog Skin: Relationship with Adenoregulin," 1994. *Biochemistry*, 33:6642-6650.

Morgan, "Chapter 3: The cell-cycle control system" in *The cell cycle: Principles of control*. New Science Press Ltd (1999) pp. 1-2.

Muller et al., "Repression of lac promotor as a function of distance, phase and quality of an auxiliary lac operator," 1996. *J Mol Biol*. 22:257(1):21-29.

Müller-Hill, "Lac Repressor and Lac Operator", 1975. *Prog. Biophys. Molec. Biol.*, 30(2/3):227-252.

Müller-Hill, *The lac Operon: A Short History of a Genetic Paradigm*, Walter de Gruyter, Berlin, New York, Title Page and Table of Contents (1996).

Munson et al., "Speeding up Protein Folding: Mutations that Increase the Rate at Which Rop folds and Unfolds by Over Four Orders of Magnitude," 1997. *Folding & Design*, 2:77-87.

Namboodiri et al., "Activation of Pineal Acetyl Coenzyme A Hydrolase by Disulfide Peptides," 1982. *J. Biol. Chem.*, 257:10030-10032.

National Center for Biotechnology Information, National Library of Medicine, National Institutes of Health, GenBank Locus ECOLAC 7477 pb ds-DNA, Accession No. J01636, "*E. coli* Lactose Operon with lacI, lacZ, lacY and lacA Genes,"[online]. Bethesda, MD (Sep. 15, 1989). <URL: //www.ncbi.nlm.nih.gov/entrez/query.fcgi?cmd=Retrieve&db=Nucleotide&list_uids=146575&dopt=GenBank, (13 pgs.).

National Center for Biotechnology Information, National Library of Medicine, National Institutes of Health, GenBank Locus SYNPBR322 4361 bp DNA circular SYN, Accession No. J01749, "Plasmid pBR322, Complete Genome," [online]. Bethesda, MD (May 20, 1991). <URL: //www.ncbi.nlm.nih.gov/entrez/query.fcgi?cmd=Retrieve&db=Nucleotide&list_uids=208958&dopt=GenBank, (13 pgs.)

National Center for Biotechnology Information, National Library of Medicine, National Institutes of Health, GenBank Locus SYNPUC8CV 2665 bp DNA circular SYN, Accession No. L09132, "pUC8c Cloning Vector (beta-galactosidase mRNA on Complementary Strand)," [online]. Bethesda, MD (Mar. 4, 1993). <URL: //www.ncbi.nlm.nih.gov/entrez/query.fcgi?cmd=Retrieve&db=Nucleotide&list_uids=146575&dopt=GenBank, (18 pgs.)

National Center for Biotechnology Information, National Library of Medicine, National Institutes of Health, GenBank Locus YP_498670, Accession No. YP_498670, "protein A (*Staphylococcus aureus* subsp. aureus NCTC 8325)," [online]. Bethesda, MD (Dec. 18, 2006). <URL: //www.ncbi.nlm.nih.gov/entrez/viewer.fcgi?db=protein&val=88193885>, (2 pgs.)

Nishida et al., "Three-dimensional Structure of *Escherichia coli* Gluthatione S-transferase Complexed with Glutathione Sulfonate: Catalytic Roles of Cys10 and His106," 1998. *J. Mol. Biol.*, 281:135-147.

Oehler et al., "Quality and position of the three lac operators of *E. coli* define efficiency of repression," 1994. *EMBO J.* 13(14):3348-55.

Olivera et al., "Conotoxins," *J. Biol. Chem.*, 1991. 266(33):22067-22070.

O'Neil et al., "A Thermodynamic Scale for the Helix-Forming Tendencies of the Commonly Occurring Amino Acids", 1990. *Science*, 250:646-651.
Ooki et al., "High level expression of rat γ-D-crystallin in *Escherischia coli*," 1994. *Biochemie*, 76(5):398-403.
Plaxco, Simplified Proteins: Minimalist Solutions to the "Protein Folding Problem," 1998. *Curr. Opin. Struct Biol.*, 8:80-85.
Plow et al., "Inhibition of Fibrinogen Binding to Human Platelets by the Tetrapeptide Glycyl-L-prolyl-L-arginyl-L-proline," 1982.*Proc. Natl. Acad. Sci. USA*, 79:3711-3715.
Posfai et al., "Overproduction of the *Bacillus sphaericus* R modification methylase in *Escherichia coli* and its purification of homogeneity", 1986. *Gene*, 50:63-67.
Prior et al, "High-level expression of soluble protein in *Escherichia coli* using a His6-tag and maltose-binding-protein double-affinity fusion system," 1997. *Protein Expr Purif.*, 10(3):309-319.
Raleigh et al. "McrA and McrB restriction phenotypes of some *E. coli* strains and implications for gene cloning", 1988. *Nucleic Acids Research*, 16:1563-1575.
Ranie et al., "Cloning of the triosephosphate isomerase gene of *Plasmodium falciparum* and expression in *Escherichia coli*", 1993. *Molecular and Biochemical Parasitology*, 61:159-169.
Rawlings et al., "Evolutionary families of peptidases", 1993. *Biochem J.*, 290:205-218.
Reed et al., "Circular Dichroic Investigations of Secondary Structure in Synthetic Peptide Inhibitors of cAMP-Dependent Protein Kinase: A Model for Inhibitory Potential," 1987. *Biochemistry*, 26:7641-7647.
Robinson et al., "Electrostatic Stabilization in Four-Helix Bundle Proteins," 1993. *Protein Science*, 2:826-837.
Ronnmark et al., Human immunoglobulin A (IgA)-specific ligands from combinatorial engineering of protein A., 2002. *Eur. J. Biochem.* 269:2647-2655.
Roseman, "Hydrophilicity of polar amino acid side-chains is markedly reduced by flanking peptide bonds," 1988. *J Mol Biol.*, 200(3):513-522.
Rosinski et al., "Molecular evolution of helix-turn-helix proteins," 1999 *J. Mol. Evol.* 49(3):301-309.
Sachdev et al., "Solubility of Proteins Isolated from Inclusion Bodies is Enhanced by Fusion to Maltose-binding Protein or Thioredoxin," 1998. *Protein Expr. Purif.*, 12:122:132.
Sanders, "Drug delivery systems and routes of administration of peptide and protein drugs", 1990. *European Journal of Drug Metabolism and Pharmacokinetics*, 15(2):95-102.
Schmidt-Krey et al., "The Three-dimensional map of microsomal glutathione transferase 1 at 6 A resolution," *EMBO J.*, 19:6311-6316, (2000).
Scott et al., "Searching for Peptide Ligands with an Epitope Library", 1990. *Science*, 249:386-390.
Scrutton et al., "Purification and characterization of glutathione reductase encoded by a cloned and over-expressed gene in *Escherichia coli*", 1987. *Biochem J.*, 245:875-880.
Sherman et al, "Methionine or Not Methionine at the Beginning of a Protein", 1985. *BioEssays*, 3(1):27-31.
Shimizu et al., "Enhancement of Antimicrobial Activity of Neuropeptide Y by N-terminal Truncation," 1998. *Antimicrob. Agents Chemother.*, 42:2745-2746.
Singer et al., "A Collection of Strains Containing Genetically Linked Alternating Antibiotic Resistance Elements for Genetic Mapping of *Escherichia coli*", 1989. *Microbiol. Rev.*, 53(1):1-24.
Smith, "Filamentous Fusion Phage: Novel Expression Vectors that Display Cloned Antigens on the Virion Surface", 1985. *Science*, 228:1315-1317.
Smith et al., "[15] Libraries of Peptides and Proteins Displayed on Filamentous Phage", 1993. *Meth. Enzymol.*, 217:228-257.
Soberon et al., "Construction and Characterization of New Cloning Vehicles. IV. Deletion Derivatives of pBR322 and pBR325," 1980. *Gene*, 9(3-4):287:305.

Spurlino et al., "The 2.3—A Resolution Structure of the Maltose- or Maltodextrin-binding Protein, a Primary Receptor of Bacterial Active Transport and Chemotaxis," 1991. *J. Biol. Chem.*, 266:5202-5219.
Steif et al., "Subunit Interactions Provide a Significant Contribution to the Stability of the Dimeric Four-α-Helical-Bundle Protein ROP," 1993. *Biochemistry*, 32(15):3867-3875.
Studier et al., "Use of Bacteriophage T7 RNA Polymerase to Direct Selective High-level Expression of Cloned Genes", 1986. *J. Mol. Biol.*, 189:113-130.
Studier et al., "Use of T7 RNA Polymerase to Direct Expression of Cloned Genes", 1990. *Meth. Enzymol.*, 185:60-89.
Studier, "Use of Bacteriophage T7 Lysozyme to Improve an Inducible T7 Expression System", 1991. *J. Mol. Biol.*, 219:37-44.
Sugio et al., "Crystal structure of human serum albumin at 2.5 Å resolution," *Protein Engineering*, 1999; 12(6):439-446.
Takeuchi et al., "Cloning of the enomycin structural gene from *Streptomyces* mauvecolor and production of recombinant enomycin in *Escherichia coli*," 1997 *J. Antibiol* (Tokyo). 50:27-31.
Terwilliger et al., "The Structure of Melittin," 1982. *J. Biol. Chem.*, 257(11):6010-6015.
Urry et al., "Confirmational Studies on Neurohypophyseal Hormones: The Disulfide Bridge of Oxytocin," 1968. *Proc. Natl. Acad. Sci. USA*, 60:967-974.
Vanhoof et al., "Proline Motifs in Peptides and Their Biological Processing," 1995. *FASEB J.*, 9:736-744.
Vieira et al., "The pUC plasmids, an M13mp7-derived system for insertion mutagenesis and sequencing with synthetic universal primers", 1982. *Gene*, 19:259-268.
Volkel et al., "Large-scale production, purification and refolding of the full-length cellular prion protein from Syrian golden hamster in *Escherichia coli* using the glutathione S-transferase-fusion system," 1998. *Eur J Biochem.*, 251(1-2):462-71.
Walter et al., "Proline Specific Endo- and Exopeptidases," 1980. *Mol. Cell. Bioch.*, 30(2):111-127.
Wang et al., "Modification of cyclin A expression by hepatitis B virus DNA integration in a hepatocellular carcinoma," 1992 *Oncogene* 7(8):1653-1656.
Watt et al., "Refolding of recombinant *Pasteurella haemolytica* A1 glycoprotease expressed in an *Escherichia coli* thioredoxin gene fusion system," 1997. *Cell Stress Chaperones*, 3:180-190.
Wearley, "Recent Progress in Protein and Peptide Delivery by Noninvasive Routes", 1991. *Crit. Rev. Ther. Drug Carrier Systems*, 8(4):331-394.
Weisemann et al., "Direct Selection of Mutations Reducing Transcription or Translation of the *recA* Gene of *Escherichia coli* with *recA-lacZ* Protein Fusion", 1985. *J. Bacteriol.*, 163(2):748-755.
Weiss et al., "Overexpression of Active Syrian Golden Hamster Prion Protein PrPc as a Glutathione S-transferase Fusion in Heterologous Systems," 1995. *J. Virol.*, 69:476-483.
Williams et al., "Secondary Structure of Substance P Bound to Liposomes in Organic Solvents and in Solution from Raman and CD Spectroscopy," 1990. *J. Biol. Chem.*, 265(5):2505-2513.
Wolfenden et al., "Affinities of Amino Acid Side Chains for Solvent Water", 1981. *Biochemistry*, 20:849-855.
Xu et al., "Primary Structure and Anticandidal Activity of the Major Histatin from Parotid Secretion of the Subhuman Primate, *Macaca fascicularis*," 1990. *J. Dent. Res.*, 69(11):1717-1723.
Yanisch-Perron et al., "Improved M13 phage cloning vectors and host strains: nucleotide sequences of the M13mp18 and pUC19 vectors", 1985. *Gene*, 33:103-119.
Yansura et al., "Use of the *Escherichia coli lac* repressor and Operator to Control Gene Expression in *Bacillus subtilis*," 1984. *Proc. Natl. Acad. Sci. USA*, 81:439-443.
Yaron et al., "Proline-Dependent Structural and Biological Properties of Peptides and Proteins," 1993. *Crit. Rev. Biochem. Mol. Biol.*, 28(1):31-81.
Yeh et al., "Design of yeast-secreted albumin derivatives for human therapy: Biological and antiviral properties of serum albumin-CD4 genetic conjugate," 1992. *Proc. Natl. Acad. Sci. USA*, 89:1904-1908.

Zukowski et al., "Chromogenic identification of genetic regulatory signals in *Bacillus subtilis* based on expression of cloned *Pseudomonas* gene," 1983. *Proc. Nat'l. Acad. Sci. USA*, 80:1101-1105.

Kametkar et al., "Protein Motifs. 7. The four-helix bundle: what determines a fold?," Aug. 1995 *FASEB J.* 9(11):1013-1022.

* cited by examiner

SEQ ID No: 1

```
        lacI
        stop
GGCAGTGAGCGCAACGCAATT AATGTGAGTTAGCTCACTCA TTAGGCACCCCAGGC TTTACA CTTTA
        O3                    CAP                                -35
                                                                        lacZ
                        +1                                      SD     start
TGCTTCCGGCTCG TATGTT GTGTGG AATTGTGAGCGGATAACAATTT CACAC AGGA AACAGCTATG
              -10              O1
```

FIG. 1 met  glu⁻ asp⁻ glu⁻ asp⁻  xaa  xaa  xaa  xaa  xaa  xaa  xaa  xaa
     lys⁺ arg⁺ lys⁺ arg⁺  xaa                          xaa  xaa
                               xaa  xaa  xaa  xaa  xaa

FIG. 9

SEQUENCE LISTING

<160> NUMBER OF SEQ ID NOS: 115

<210> SEQ ID NO 1
<211> LENGTH: 133
<212> TYPE: DNA
<213> ORGANISM: Escherichia coli

<400> SEQUENCE: 1
ggcagtgagc gcaacgcaat taatgtgagt tagctcactc attaggcacc ccaggcttta      60
cactttatgc ttccggctcg tatgttgtgt ggaattgtga gcggataaca atttcacaca     120
ggaaacagct atg                                                        133

<210> SEQ ID NO 2
<211> LENGTH: 25
<212> TYPE: PRT
<213> ORGANISM: ARTIFICIAL
<220> FEATURE:
<223> OTHER INFORMATION: peptide having opposite charge ending motif
<220> FEATURE:
<221> NAME/KEY: SITE
<222> LOCATION: (6)..(21)
<223> OTHER INFORMATION: any amino acid

<400> SEQUENCE: 2

Met Glu Asp Glu Asp Xaa Xaa Xaa Xaa Xaa Xaa Xaa Xaa Xaa Xaa
1               5                   10                  15

Xaa Xaa Xaa Xaa Xaa Arg Lys Arg Lys
            20                  25

<210> SEQ ID NO 3
<211> LENGTH: 14
<212> TYPE: PRT
<213> ORGANISM: ARTIFICIAL
<220> FEATURE:
<223> OTHER INFORMATION: stabilized angiotesin

<400> SEQUENCE: 3

Pro Pro Asp Arg Val Tyr Ile His Pro Phe His Ile Pro Pro
1               5                   10

<210> SEQ ID NO 4
<211> LENGTH: 18
<212> TYPE: PRT
<213> ORGANISM: ARTIFICIAL
<220> FEATURE:
<223> OTHER INFORMATION: stabilized angiotensin

<400> SEQUENCE: 4

Glu Asp Glu Asp Asp Arg Val Tyr Ile His Pro Phe His Ile Arg Lys
1               5                   10                  15

Arg Lys

<210> SEQ ID NO 5
<211> LENGTH: 10
<212> TYPE: PRT
<213> ORGANISM: Homo Sapiens

<400> SEQUENCE: 5

Asp Arg Val Tyr Ile His Pro Phe His Ile
1               5                   10

<210> SEQ ID NO 6
<211> LENGTH: 20

```
<212> TYPE: DNA
<213> ORGANISM: ARTIFICIAL
<220> FEATURE:
<223> OTHER INFORMATION: primer

<400> SEQUENCE: 6
gttgccattg ctgcaggcat                                             20

<210> SEQ ID NO 7
<211> LENGTH: 42
<212> TYPE: DNA
<213> ORGANISM: ARTIFICIAL
<220> FEATURE:
<223> OTHER INFORMATION: primer

<400> SEQUENCE: 7
attgaattca taagatcttt cctgtgtgaa attgttatcc gc                    42

<210> SEQ ID NO 8
<211> LENGTH: 37
<212> TYPE: DNA
<213> ORGANISM: ARTIFICIAL
<220> FEATURE:
<223> OTHER INFORMATION: primer

<400> SEQUENCE: 8
attgaattca ccatggacac catcgaatgg tgcaaaa                          37

<210> SEQ ID NO 9
<211> LENGTH: 19
<212> TYPE: DNA
<213> ORGANISM: ARTIFICIAL
<220> FEATURE:
<223> OTHER INFORMATION: primer

<400> SEQUENCE: 9
gttgttgcca ttgctgcag                                              19

<210> SEQ ID NO 10
<211> LENGTH: 43
<212> TYPE: DNA
<213> ORGANISM: ARTIFICIAL
<220> FEATURE:
<223> OTHER INFORMATION: primer

<400> SEQUENCE: 10
tgtatgaatt cccgggtacc atggttgaag acgaaagggc ctc                   43

<210> SEQ ID NO 11
<211> LENGTH: 36
<212> TYPE: DNA
<213> ORGANISM: ARTIFICIAL
<220> FEATURE:
<223> OTHER INFORMATION: primer

<400> SEQUENCE: 11
tactatagat ctatgaccat gattacggat tcactg                           36

<210> SEQ ID NO 12
<211> LENGTH: 36
<212> TYPE: DNA
<213> ORGANISM: ARTIFICIAL
<220> FEATURE:
<223> OTHER INFORMATION: primer

<400> SEQUENCE: 12
tacataaagc ttggcctgcc cggttattat tatttt                           36
```

<210> SEQ ID NO 13
<211> LENGTH: 47
<212> TYPE: DNA
<213> ORGANISM: ARTIFICIAL
<220> FEATURE:
<223> OTHER INFORMATION: primer

<400> SEQUENCE: 13
tatcatctgc agaggaaaca gctatgacca tgattacgga ttcactg         47

<210> SEQ ID NO 14
<211> LENGTH: 47
<212> TYPE: DNA
<213> ORGANISM: ARTIFICIAL
<220> FEATURE:
<223> OTHER INFORMATION: primer

<400> SEQUENCE: 14
tacatactcg agcaggaaag cttggcctgc ccggttatta ttatttt         47

<210> SEQ ID NO 15
<211> LENGTH: 47
<212> TYPE: DNA
<213> ORGANISM: ARTIFICIAL
<220> FEATURE:
<223> OTHER INFORMATION: primer

<400> SEQUENCE: 15
tatcatggat ccaggaaaca gctatgacca tgattacgga ttcactg         47

<210> SEQ ID NO 16
<211> LENGTH: 36
<212> TYPE: DNA
<213> ORGANISM: ARTIFICIAL
<220> FEATURE:
<223> OTHER INFORMATION: primer

<400> SEQUENCE: 16
tactatagat ctatggctat cgacgaaaac aaacag         36

<210> SEQ ID NO 17
<211> LENGTH: 40
<212> TYPE: DNA
<213> ORGANISM: ARTIFICIAL
<220> FEATURE:
<223> OTHER INFORMATION: primer

<400> SEQUENCE: 17
atatataagc ttttaaaaat cttcgttagt ttctgctacg         40

<210> SEQ ID NO 18
<211> LENGTH: 35
<212> TYPE: DNA
<213> ORGANISM: ARTIFICIAL
<220> FEATURE:
<223> OTHER INFORMATION: primer

<400> SEQUENCE: 18
tactatagat ctatgaacaa aggtgtaatg cgacc         35

<210> SEQ ID NO 19
<211> LENGTH: 35
<212> TYPE: DNA
<213> ORGANISM: ARTIFICIAL
<220> FEATURE:
<223> OTHER INFORMATION: primer

```
<400> SEQUENCE: 19
attagtgaat tcgcacaatc tctgcaataa gtcgt                                35

<210> SEQ ID NO 20
<211> LENGTH: 15
<212> TYPE: DNA
<213> ORGANISM: ARTIFICIAL
<220> FEATURE:
<223> OTHER INFORMATION: primer fragment

<400> SEQUENCE: 20
agatcttatg aattc                                                     15

<210> SEQ ID NO 21
<211> LENGTH: 15
<212> TYPE: DNA
<213> ORGANISM: ARTIFICIAL
<220> FEATURE:
<223> OTHER INFORMATION: primer fragment

<400> SEQUENCE: 21
agatcttatg aattc                                                     15

<210> SEQ ID NO 22
<211> LENGTH: 15
<212> TYPE: DNA
<213> ORGANISM: ARTIFICIAL
<220> FEATURE:
<223> OTHER INFORMATION: primer fragment

<400> SEQUENCE: 22
agatcttatg aattc                                                     15

<210> SEQ ID NO 23
<211> LENGTH: 93
<212> TYPE: DNA
<213> ORGANISM: ARTIFICIAL
<220> FEATURE:
<223> OTHER INFORMATION: randomized oligonucleotide
<220> FEATURE:
<221> NAME/KEY: misc_feature
<222> LOCATION: (16)..(75)
<223> OTHER INFORMATION: a, g, c, or t

<400> SEQUENCE: 23
tactatagat ctatgnnnnn nnnnnnnnnn nnnnnnnnnn nnnnnnnnnn nnnnnnnnnn     60
nnnnnnnnnn nnnntaata agaattctcg aca                                  93

<210> SEQ ID NO 24
<211> LENGTH: 18
<212> TYPE: DNA
<213> ORGANISM: ARTIFICIAL
<220> FEATURE:
<223> OTHER INFORMATION: primer

<400> SEQUENCE: 24
tgtcgagaat tcttatta                                                  18

<210> SEQ ID NO 25
<211> LENGTH: 20
<212> TYPE: DNA
<213> ORGANISM: ARTIFICIAL
<220> FEATURE:
<223> OTHER INFORMATION: primer

<400> SEQUENCE: 25
```

```
tcattaatgc agctggcacg                                                    20

<210> SEQ ID NO 26
<211> LENGTH: 20
<212> TYPE: DNA
<213> ORGANISM: ARTIFICIAL
<220> FEATURE:
<223> OTHER INFORMATION: primer

<400> SEQUENCE: 26
ttcatacacg gtgcctgact                                                    20

<210> SEQ ID NO 27
<211> LENGTH: 20
<212> TYPE: DNA
<213> ORGANISM: ARTIFICIAL
<220> FEATURE:
<223> OTHER INFORMATION: primer

<400> SEQUENCE: 27
tagctcactc attaggcacc                                                    20

<210> SEQ ID NO 28
<211> LENGTH: 20
<212> TYPE: DNA
<213> ORGANISM: ARTIFICIAL
<220> FEATURE:
<223> OTHER INFORMATION: primer

<400> SEQUENCE: 28
gatgacgatg agcgcattgt                                                    20

<210> SEQ ID NO 29
<211> LENGTH: 92
<212> TYPE: DNA
<213> ORGANISM: ARTIFICIAL
<220> FEATURE:
<223> OTHER INFORMATION: antisense oligonucleotide

<400> SEQUENCE: 29
tactatagat ctacggtcac tgaattttgt ggcttgttgg accaactgcc ttagtaatag        60
tggaaggctg aaattaataa gaattctcga ca                                      92

<210> SEQ ID NO 30
<211> LENGTH: 91
<212> TYPE: DNA
<213> ORGANISM: ARTIFICIAL
<220> FEATURE:
<223> OTHER INFORMATION: antisense oligonucleotide

<400> SEQUENCE: 30
tactatagat ctacgtggcg ggactcatgg attaagggta gggacgtggg gtttatgggt        60
taaaatagtt tgataataag aattctcgac a                                       91

<210> SEQ ID NO 31
<211> LENGTH: 92
<212> TYPE: DNA
<213> ORGANISM: ARTIFICIAL
<220> FEATURE:
<223> OTHER INFORMATION: antisense oligonucleotide

<400> SEQUENCE: 31
tactatagat ctacgaacgg ccgaaccaaa cgaatccggg acccaccagc cgcctaaaca        60
gctaccagct gtggtaataa gaattctcga ca                                      92
```

```
<210> SEQ ID NO 32
<211> LENGTH: 93
<212> TYPE: DNA
<213> ORGANISM: ARTIFICIAL
<220> FEATURE:
<223> OTHER INFORMATION: antisense oligonucleotide

<400> SEQUENCE: 32
tactatagat ctacggaccg tgaagtgatg tgtgcggcaa acaggaatg gaaggaacga      60 acgccatagg ccgcgtaata agaattctcg aca                                 93

<210> SEQ ID NO 33
<211> LENGTH: 93
<212> TYPE: DNA
<213> ORGANISM: ARTIFICIAL
<220> FEATURE:
<223> OTHER INFORMATION: antisense oligonucleotide

<400> SEQUENCE: 33
tactatagat ctacgagggg cgccaactaa ggggggggga aggtatttgt cccgtgcata     60
atctcgggtg ttgtctaata agaattctcg aca                                 93

<210> SEQ ID NO 34
<211> LENGTH: 13
<212> TYPE: PRT
<213> ORGANISM: ARTIFICIAL
<220> FEATURE:
<223> OTHER INFORMATION: stabilized peptide

<400> SEQUENCE: 34

Met Val Thr Glu Phe Cys Gly Leu Leu Asp Gln Leu Pro
1               5                   10

<210> SEQ ID NO 35
<211> LENGTH: 86
<212> TYPE: DNA
<213> ORGANISM: ARTIFICIAL
<220> FEATURE:
<223> OTHER INFORMATION: nucleic acid encoding stabilized peptide

<400> SEQUENCE: 35
caggaaagat ctatggtcac tgaattttgt ggcttgttgg accaactgcc ttagtaatag     60
tggaaggctg aaattaataa gaattc                                         86

<210> SEQ ID NO 36
<211> LENGTH: 16
<212> TYPE: PRT
<213> ORGANISM: ARTIFICIAL
<220> FEATURE:
<223> OTHER INFORMATION: stabilized peptide

<400> SEQUENCE: 36

Met Trp Arg Asp Ser Trp Ile Lys Gly Arg Asp Val Gly Phe Met Gly
1               5                   10                  15

<210> SEQ ID NO 37
<211> LENGTH: 85
<212> TYPE: DNA
<213> ORGANISM: ARTIFICIAL
<220> FEATURE:
<223> OTHER INFORMATION: nucleic acid encoding stabilized peptide

<400> SEQUENCE: 37
caggaaagat ctatgtggcg ggactcatgg attaaggta gggacgtggg gtttatgggt     60
```

```
taaaatagtt tgataataag aattc                                             85

<210> SEQ ID NO 38
<211> LENGTH: 141
<212> TYPE: DNA
<213> ORGANISM: ARTIFICIAL
<220> FEATURE:
<223> OTHER INFORMATION: nucleic acid encoding stabilized peptide

<400> SEQUENCE: 38
caggaaagat ctatgtcagg gggacatgtg acgagggagt gcaagtcggc gatgtccaat       60
cgttggatct acgtaataag aattctcatg tttgacagct tatcatcgat aagctttaat      120
gcggtagttt atcacagtta a                                                141

<210> SEQ ID NO 39
<211> LENGTH: 42
<212> TYPE: PRT
<213> ORGANISM: ARTIFICIAL
<220> FEATURE:
<223> OTHER INFORMATION: stabilized peptide

<400> SEQUENCE: 39

Met Ser Gly Gly His Val Thr Arg Glu Cys Lys Ser Ala Met Ser Asn
 1               5                  10                  15

Arg Trp Ile Tyr Val Ile Arg Ile Leu Met Phe Asp Ser Leu Ser Ser
            20                  25                  30

Ile Ser Phe Asn Ala Val Val Tyr His Ser
        35                  40

<210> SEQ ID NO 40
<211> LENGTH: 6
<212> TYPE: PRT
<213> ORGANISM: ARTIFICIAL
<220> FEATURE:
<223> OTHER INFORMATION: stabilized peptide

<400> SEQUENCE: 40

Met Tyr Leu Phe Ile Gly
 1               5

<210> SEQ ID NO 41
<211> LENGTH: 75
<212> TYPE: DNA
<213> ORGANISM: ARTIFICIAL
<220> FEATURE:
<223> OTHER INFORMATION: nucleic acid encoding stabilized peptide

<400> SEQUENCE: 41
caggaaagat ctatgtattt gttcatcgga taatacttaa tggtccgctg gagaacttca       60
gtttaataag aattc                                                        75

<210> SEQ ID NO 42
<211> LENGTH: 87
<212> TYPE: DNA
<213> ORGANISM: ARTIFICIAL
<220> FEATURE:
<223> OTHER INFORMATION: nucleic acid encoding stabilized peptide

<400> SEQUENCE: 42
caggaaagat ctatgcttct atttggggggg gactgcgggc agaaagccgg atactttact      60
gtgctaccgt caaggtaata agaattc                                           87
```

```
<210> SEQ ID NO 43
<211> LENGTH: 20
<212> TYPE: PRT
<213> ORGANISM: ARTIFICIAL
<220> FEATURE:
<223> OTHER INFORMATION: stabilized peptide

<400> SEQUENCE: 43

Met Leu Leu Phe Gly Gly Asp Cys Gly Lys Ala Gly Tyr Phe Thr Val
1               5                   10                  15

Leu Pro Ser Arg
            20

<210> SEQ ID NO 44
<211> LENGTH: 75
<212> TYPE: DNA
<213> ORGANISM: ARTIFICIAL
<220> FEATURE:
<223> OTHER INFORMATION: nucleic acid encoding stabilized peptide

<400> SEQUENCE: 44
caggaaagat ctatgattgg gggatcgttg agcttcgcct gggcaatagt ttgtaataag      60
aattctcatg tttga                                                      75

<210> SEQ ID NO 45
<211> LENGTH: 20
<212> TYPE: PRT
<213> ORGANISM: ARTIFICIAL
<220> FEATURE:
<223> OTHER INFORMATION: stabilized peptide

<400> SEQUENCE: 45

Met Ile Gly Gly Ser Leu Ser Phe Ala Trp Ala Ile Val Cys Asn Lys
1               5                   10                  15

Asn Ser His Val
            20

<210> SEQ ID NO 46
<211> LENGTH: 14
<212> TYPE: PRT
<213> ORGANISM: ARTIFICIAL
<220> FEATURE:
<223> OTHER INFORMATION: stabilized peptide

<400> SEQUENCE: 46

Met Asn Gly Arg Thr Lys Arg Ile Arg Asp Pro Pro Ala Ala
1               5                   10

<210> SEQ ID NO 47
<211> LENGTH: 86
<212> TYPE: DNA
<213> ORGANISM: ARTIFICIAL
<220> FEATURE:
<223> OTHER INFORMATION: nucleic acid encoding stabilized peptide

<400> SEQUENCE: 47
caggaaagat ctatgaacgg ccgaaccaaa cgaatccggg acccaccagc cgcctaaaca      60
gctaccagct gtggtaataa gaattc                                          86

<210> SEQ ID NO 48
<211> LENGTH: 18
<212> TYPE: PRT
<213> ORGANISM: ARTIFICIAL
<220> FEATURE:
<223> OTHER INFORMATION: stabilized peptide
```

-continued

```
<400> SEQUENCE: 48

Met Asp Arg Glu Val Met Cys Ala Ala Lys Gln Glu Trp Lys Glu Arg
1               5                   10                  15

Thr Pro

<210> SEQ ID NO 49
<211> LENGTH: 87
<212> TYPE: DNA
<213> ORGANISM: ARTIFICIAL
<220> FEATURE:
<223> OTHER INFORMATION: nucleic acid encoding stabilized peptide

<400> SEQUENCE: 49
caggaaagat ctatggaccg tgaagtgatg tgtgcggcaa acaggaatg gaaggaacga      60 acgccatagg ccgcgtaata agaattc                                        87

<210> SEQ ID NO 50
<211> LENGTH: 87
<212> TYPE: DNA
<213> ORGANISM: ARTIFICIAL
<220> FEATURE:
<223> OTHER INFORMATION: nucleic acid encoding stabilized peptide

<400> SEQUENCE: 50
caggaaagat ctatgtagcc caatgcactg ggagcacgcg tgttaggtct agaagccacg      60
tacccattta atccataata agaattc                                         87

<210> SEQ ID NO 51
<211> LENGTH: 12
<212> TYPE: PRT
<213> ORGANISM: ARTIFICIAL
<220> FEATURE:
<223> OTHER INFORMATION: stabilized peptide

<400> SEQUENCE: 51

Met Leu Gly Leu Glu Ala Thr Tyr Pro Phe Asn Pro
1               5                   10

<210> SEQ ID NO 52
<211> LENGTH: 5
<212> TYPE: PRT
<213> ORGANISM: ARTIFICIAL
<220> FEATURE:
<223> OTHER INFORMATION: stabilized peptide

<400> SEQUENCE: 52

Met Arg Gly Ala Asn
1               5

<210> SEQ ID NO 53
<211> LENGTH: 87
<212> TYPE: DNA
<213> ORGANISM: ARTIFICIAL
<220> FEATURE:
<223> OTHER INFORMATION: nucleic acid encoding stabilized peptide

<400> SEQUENCE: 53
caggaaagat ctatgagggg cgccaactaa gggggggga aggtatttgt cccgtgcata       60
atctcgggtg ttgtctaata agaattc                                         87

<210> SEQ ID NO 54
<211> LENGTH: 4
<212> TYPE: PRT
<213> ORGANISM: ARTIFICIAL
```

```
<220> FEATURE:
<223> OTHER INFORMATION: N-terminal protective sequence
<220> FEATURE:
<221> NAME/KEY: SITE
<222> LOCATION: (1)..(1)
<223> OTHER INFORMATION: any amino acid
<220> FEATURE:
<221> NAME/KEY: SITE
<222> LOCATION: (4)..(4)
<223> OTHER INFORMATION: any amino acid

<400> SEQUENCE: 54

Xaa Pro Pro Xaa
1

<210> SEQ ID NO 55
<211> LENGTH: 36
<212> TYPE: DNA
<213> ORGANISM: ARTIFICIAL
<220> FEATURE:
<223> OTHER INFORMATION: primer

<400> SEQUENCE: 55
tactatagat ctatgaccaa acaggaaaaa accgcc                                 36

<210> SEQ ID NO 56
<211> LENGTH: 36
<212> TYPE: DNA
<213> ORGANISM: ARTIFICIAL
<220> FEATURE:
<223> OTHER INFORMATION: primer

<400> SEQUENCE: 56
tatacgtatt cagttgctca catgttcttt cctgcg                                 36

<210> SEQ ID NO 57
<211> LENGTH: 41
<212> TYPE: DNA
<213> ORGANISM: ARTIFICIAL
<220> FEATURE:
<223> OTHER INFORMATION: primer

<400> SEQUENCE: 57
aattcatact atagatctat gaccaaacag gaaaaaaccg c                           41

<210> SEQ ID NO 58
<211> LENGTH: 42
<212> TYPE: DNA
<213> ORGANISM: ARTIFICIAL
<220> FEATURE:
<223> OTHER INFORMATION: primer

<400> SEQUENCE: 58
tatataatac atgtcagaat tcgaggtttt caccgtcatc ac                          42

<210> SEQ ID NO 59
<211> LENGTH: 96
<212> TYPE: DNA
<213> ORGANISM: ARTIFICIAL
<220> FEATURE:
<223> OTHER INFORMATION: randomized oligonucleotide
<220> FEATURE:
<221> NAME/KEY: misc_feature
<222> LOCATION: (16)..(75)
<223> OTHER INFORMATION: a, g, c, or t

<400> SEQUENCE: 59
tactatagat ctatgnnnnn nnnnnnnnnn nnnnnnnnnn nnnnnnnnnn nnnnnnnnn        60
```
nnnnnnnnnn nnnnncatag atctgcgtgc tgtgat 96

```
<210> SEQ ID NO 60
<211> LENGTH: 21
<212> TYPE: DNA
<213> ORGANISM: ARTIFICIAL
<220> FEATURE:
<223> OTHER INFORMATION: primer

<400> SEQUENCE: 60
```
atcacagcac gcagatctat g 21

```
<210> SEQ ID NO 61
<211> LENGTH: 36
<212> TYPE: DNA
<213> ORGANISM: ARTIFICIAL
<220> FEATURE:
<223> OTHER INFORMATION: randomized oligonucleotide
<220> FEATURE:
<221> NAME/KEY: misc_feature
<222> LOCATION: (13)..(15)
<223> OTHER INFORMATION: a, g, c, or t

<400> SEQUENCE: 61
```
tactatgaat tcnnngaatt ctgccaccac tactat 36

```
<210> SEQ ID NO 62
<211> LENGTH: 21
<212> TYPE: DNA
<213> ORGANISM: ARTIFICIAL
<220> FEATURE:
<223> OTHER INFORMATION: primer

<400> SEQUENCE: 62
```
atagtagtgg tggcagaatt c 21

```
<210> SEQ ID NO 63
<211> LENGTH: 105
<212> TYPE: DNA
<213> ORGANISM: ARTIFICIAL
<220> FEATURE:
<223> OTHER INFORMATION: randomized oligonucleotide
<220> FEATURE:
<221> NAME/KEY: misc_feature
<222> LOCATION: (22)..(81)
<223> OTHER INFORMATION: a, g, c, or t

<400> SEQUENCE: 63
```
tactatagat ctatgccgcc gnnnnnnnnn nnnnnnnnnn nnnnnnnnnn nnnnnnnnnn 60
nnnnnnnnnn nnnnnnnnnn nccgccgtaa taagaattcg tacat 105

```
<210> SEQ ID NO 64
<211> LENGTH: 24
<212> TYPE: DNA
<213> ORGANISM: ARTIFICIAL
<220> FEATURE:
<223> OTHER INFORMATION: primer

<400> SEQUENCE: 64
```
atgtacgaat tcttattacg gcgg 24

```
<210> SEQ ID NO 65
<211> LENGTH: 90
<212> TYPE: DNA
<213> ORGANISM: ARTIFICIAL
<220> FEATURE:
<223> OTHER INFORMATION: randomized oligonucleotide
<220> FEATURE:
```

```
<221> NAME/KEY: misc_feature
<222> LOCATION: (18)..()
<223> OTHER INFORMATION: a, g, c, or t
<220> FEATURE:
<221> NAME/KEY: misc_feature
<222> LOCATION: (21)..()
<223> OTHER INFORMATION: a, g, c, or t
<220> FEATURE:
<221> NAME/KEY: misc_feature
<222> LOCATION: (24)..()
<223> OTHER INFORMATION: a, g, c, or t
<220> FEATURE:
<221> NAME/KEY: misc_feature
<222> LOCATION: (27)..()
<223> OTHER INFORMATION: a, g, c, or t
<220> FEATURE:
<221> NAME/KEY: misc_feature
<222> LOCATION: (30)..()
<223> OTHER INFORMATION: a, g, c, or t
<220> FEATURE:
<221> NAME/KEY: misc_feature
<222> LOCATION: (33)..()
<223> OTHER INFORMATION: a, g, c, or t
<220> FEATURE:
<221> NAME/KEY: misc_feature
<222> LOCATION: (36)..()
<223> OTHER INFORMATION: a, g, c, or t
<220> FEATURE:
<221> NAME/KEY: misc_feature
<222> LOCATION: (39)..()
<223> OTHER INFORMATION: a, g, c, or t
<220> FEATURE:
<221> NAME/KEY: misc_feature
<222> LOCATION: (42)..()
<223> OTHER INFORMATION: a, g, c, or t
<220> FEATURE:
<221> NAME/KEY: misc_feature
<222> LOCATION: (45)..()
<223> OTHER INFORMATION: a, g, c, or t
<220> FEATURE:
<221> NAME/KEY: misc_feature
<222> LOCATION: (48)..()
<223> OTHER INFORMATION: a, g, c, or t
<220> FEATURE:
<221> NAME/KEY: misc_feature
<222> LOCATION: (51)..()
<223> OTHER INFORMATION: a, g, c, or t
<220> FEATURE:
<221> NAME/KEY: misc_feature
<222> LOCATION: (54)..()
<223> OTHER INFORMATION: a, g, c, or t
<220> FEATURE:
<221> NAME/KEY: misc_feature
<222> LOCATION: (57)..()
<223> OTHER INFORMATION: a, g, c, or t
<220> FEATURE:
<221> NAME/KEY: misc_feature
<222> LOCATION: (60)..()
<223> OTHER INFORMATION: a, g, c, or t
<220> FEATURE:
<221> NAME/KEY: misc_feature
<222> LOCATION: (63)..()
<223> OTHER INFORMATION: a, g, c, or t
<220> FEATURE:
<221> NAME/KEY: misc_feature
<222> LOCATION: (66)..()
<223> OTHER INFORMATION: a, g, c, or t

<400> SEQUENCE: 65
tactatagat ctatgvanva nvanvanvan vanvanvanv anvanvanva nvanvanvan      60
vanvantaat aagaattctg ccagcactat                                       90

<210> SEQ ID NO 66
<211> LENGTH: 24
<212> TYPE: DNA
<213> ORGANISM: ARTIFICIAL
<220> FEATURE:
```

```
<223> OTHER INFORMATION: primer

<400> SEQUENCE: 66
atagtgctgg cagaattctt atta                                          24

<210> SEQ ID NO 67
<211> LENGTH: 105
<212> TYPE: DNA
<213> ORGANISM: ARTIFICIAL
<220> FEATURE:
<223> OTHER INFORMATION: randomized oligonucleotide
<220> FEATURE:
<221> NAME/KEY: misc_feature
<222> LOCATION: (28)..(75)
<223> OTHER INFORMATION: a, g, c, or t

<400> SEQUENCE: 67
tactatagat ctatggaaga cgaagacnnn nnnnnnnnnn nnnnnnnnnn nnnnnnnnnn   60
nnnnnnnnnn nnnnncgtaa acgtaaataa taagaattcg tacat                  105

<210> SEQ ID NO 68
<211> LENGTH: 30
<212> TYPE: DNA
<213> ORGANISM: ARTIFICIAL
<220> FEATURE:
<223> OTHER INFORMATION: primer

<400> SEQUENCE: 68
atgtacgaat tcttattatt tacgtttacg                                    30

<210> SEQ ID NO 69
<211> LENGTH: 81
<212> TYPE: DNA
<213> ORGANISM: ARTIFICIAL
<220> FEATURE:
<223> OTHER INFORMATION: nucleic acid encoding stabilized peptide

<400> SEQUENCE: 69
agatctatgc cgccgattct atggggcgaa gcgagaaagc gcttgtgggg tgggatcat    60 acaccgccgt aataagaatt c                                             81

<210> SEQ ID NO 70
<211> LENGTH: 21
<212> TYPE: PRT
<213> ORGANISM: ARTIFICIAL
<220> FEATURE:
<223> OTHER INFORMATION: stabilized peptide

<400> SEQUENCE: 70

Met Pro Pro Ile Leu Trp Gly Glu Ala Arg Lys Arg Leu Trp Gly Gly
1               5                   10                  15

Asp His Thr Pro Pro
            20

<210> SEQ ID NO 71
<211> LENGTH: 90
<212> TYPE: DNA
<213> ORGANISM: ARTIFICIAL
<220> FEATURE:
<223> OTHER INFORMATION: nucleic acid encoding stabilized peptide

<400> SEQUENCE: 71
agatctatgc cgccgccgtt ggatattgtg tcgggtattg aggtaggggg gcatttgtgg   60
tgccgccgta ttaagaattc tcatgtttga                                    90
```

```
<210> SEQ ID NO 72
<211> LENGTH: 27
<212> TYPE: PRT
<213> ORGANISM: ARTIFICIAL
<220> FEATURE:
<223> OTHER INFORMATION: stabilized peptide

<400> SEQUENCE: 72

Met Pro Pro Leu Asp Ile Val Ser Gly Ile Glu Val Gly Gly His
1               5                   10                  15

Leu Trp Cys Arg Arg Ile Lys Asn Ser His Val
            20                  25

<210> SEQ ID NO 73
<211> LENGTH: 81
<212> TYPE: DNA
<213> ORGANISM: ARTIFICIAL
<220> FEATURE:
<223> OTHER INFORMATION: nucleic acid encoding stabilized peptide

<400> SEQUENCE: 73
agatctatgc cgccggacaa tccggtcctg tgatgaagcg gaggtcgacc aagggggatat    60 cagccgccgt aataagaatt c                                               81

<210> SEQ ID NO 74
<211> LENGTH: 8
<212> TYPE: PRT
<213> ORGANISM: ARTIFICIAL
<220> FEATURE:
<223> OTHER INFORMATION: stabilized peptide

<400> SEQUENCE: 74

Met Pro Pro Asp Asn Pro Val Leu
1               5

<210> SEQ ID NO 75
<211> LENGTH: 81
<212> TYPE: DNA
<213> ORGANISM: ARTIFICIAL
<220> FEATURE:
<223> OTHER INFORMATION: nucleic acid encoding stabilized peptide

<400> SEQUENCE: 75
agatctatgc cgccgctatt ggacggagat gacaaataga tatatgcgtg gttgttttc    60 tgtccgccgt aataagaatt c                                              81

<210> SEQ ID NO 76
<211> LENGTH: 10
<212> TYPE: PRT
<213> ORGANISM: ARTIFICIAL
<220> FEATURE:
<223> OTHER INFORMATION: stabilized peptide

<400> SEQUENCE: 76

Met Pro Pro Leu Leu Asp Gly Asp Asp Lys
1               5                   10

<210> SEQ ID NO 77
<211> LENGTH: 79
<212> TYPE: DNA
<213> ORGANISM: ARTIFICIAL
<220> FEATURE:
<223> OTHER INFORMATION: nucleic acid encoding stabilized peptide

<400> SEQUENCE: 77
```

```
agatctatgc cgccgaggtg aagatgttg ataagacagt gacagatgcg ttccattact    60
cccgccgtaa taagaattc                                               79
```

<210> SEQ ID NO 78
<211> LENGTH: 11
<212> TYPE: PRT
<213> ORGANISM: ARTIFICIAL
<220> FEATURE:
<223> OTHER INFORMATION: stabilized peptide

<400> SEQUENCE: 78

```
Met Pro Pro Arg Trp Lys Met Leu Ile Arg Gln
1               5                   10
```

<210> SEQ ID NO 79
<211> LENGTH: 39
<212> TYPE: DNA
<213> ORGANISM: ARTIFICIAL
<220> FEATURE:
<223> OTHER INFORMATION: nucleic acid encoding stabilized peptide

<400> SEQUENCE: 79

```
agatctatga tgagagtagc gccgccgtaa taagaattc                          39
```

<210> SEQ ID NO 80
<211> LENGTH: 7
<212> TYPE: PRT
<213> ORGANISM: ARTIFICIAL
<220> FEATURE:
<223> OTHER INFORMATION: stabilized peptide

<400> SEQUENCE: 80

```
Met Met Arg Val Ala Pro Pro
1               5
```

<210> SEQ ID NO 81
<211> LENGTH: 81
<212> TYPE: DNA
<213> ORGANISM: ARTIFICIAL
<220> FEATURE:
<223> OTHER INFORMATION: nucleic acid encoding stabilized peptide

<400> SEQUENCE: 81

```
agatctatgc cgccgttgcg cggggcatgc gatgtatatg ggtaaattg aatgtcttgt    60 gggccgccgt aataagaatt c                                             81
```

<210> SEQ ID NO 82
<211> LENGTH: 14
<212> TYPE: PRT
<213> ORGANISM: ARTIFICIAL
<220> FEATURE:
<223> OTHER INFORMATION: stabilized peptide

<400> SEQUENCE: 82

```
Met Pro Pro Leu Arg Gly Ala Cys Asp Val Tyr Gly Val Asn
1               5                   10
```

<210> SEQ ID NO 83
<211> LENGTH: 81
<212> TYPE: DNA
<213> ORGANISM: ARTIFICIAL
<220> FEATURE:
<223> OTHER INFORMATION: nucleic acid encoding stabilized peptide

<400> SEQUENCE: 83

```
agatctatgc cgccggggag aggggaagcg gtgggagtga catgcttgag cgcgaacgtg    60
```

```
tacccgccgt aataagaatt c                                             81
```

<210> SEQ ID NO 84
<211> LENGTH: 21
<212> TYPE: PRT
<213> ORGANISM: ARTIFICIAL
<220> FEATURE:
<223> OTHER INFORMATION: stabilized peptide

<400> SEQUENCE: 84

```
Met Pro Pro Gly Arg Gly Glu Ala Val Gly Val Thr Cys Leu Ser Ala
1               5                   10                  15

Asn Val Tyr Pro Pro
            20
```

<210> SEQ ID NO 85
<211> LENGTH: 81
<212> TYPE: DNA
<213> ORGANISM: ARTIFICIAL
<220> FEATURE:
<223> OTHER INFORMATION: nucleic acid encoding stabilized peptide

<400> SEQUENCE: 85

```
agatctatgc cgccgggaag ggtagtgttc tttgtcgcta tctttgtttc cgcaatatgc    60
ctcccgccgt aataagaatt c                                             81
```

<210> SEQ ID NO 86
<211> LENGTH: 21
<212> TYPE: PRT
<213> ORGANISM: ARTIFICIAL
<220> FEATURE:
<223> OTHER INFORMATION: stabilized peptide

<400> SEQUENCE: 86

```
Met Pro Pro Gly Arg Val Val Phe Phe Val Ala Ile Phe Val Ser Ala
1               5                   10                  15

Ile Cys Leu Pro Pro
            20
```

<210> SEQ ID NO 87
<211> LENGTH: 81
<212> TYPE: DNA
<213> ORGANISM: ARTIFICIAL
<220> FEATURE:
<223> OTHER INFORMATION: nucleic acid encoding stabilized peptide

<400> SEQUENCE: 87

```
agatctatgc cgccgaggtt cgctcatgag agtgttaaag ggctggggga cgttacaaaa    60
gctccgccgt aataagaatt c                                             81
```

<210> SEQ ID NO 88
<211> LENGTH: 21
<212> TYPE: PRT
<213> ORGANISM: ARTIFICIAL
<220> FEATURE:
<223> OTHER INFORMATION: stabilized peptide

<400> SEQUENCE: 88

```
Met Pro Pro Arg Phe Ala His Glu Ser Val Lys Gly Leu Gly Asp Val
1               5                   10                  15

Thr Lys Ala Pro Pro
            20
```

```
<210> SEQ ID NO 89
<211> LENGTH: 72
<212> TYPE: DNA
<213> ORGANISM: ARTIFICIAL
<220> FEATURE:
<223> OTHER INFORMATION: nucleic acid encoding stabilized peptide

<400> SEQUENCE: 89
agatctatgc atgacgaaca agaggaggag cacaataaaa aggataacga aaagaacac      60 taataagaat tc                                                         72

<210> SEQ ID NO 90
<211> LENGTH: 18
<212> TYPE: PRT
<213> ORGANISM: ARTIFICIAL
<220> FEATURE:
<223> OTHER INFORMATION: stabilized peptide

<400> SEQUENCE: 90

Met His Asp Glu Gln Glu Glu His Asn Lys Lys Asp Asn Glu Lys
1               5                   10                  15

Glu His

<210> SEQ ID NO 91
<211> LENGTH: 75
<212> TYPE: DNA
<213> ORGANISM: ARTIFICIAL
<220> FEATURE:
<223> OTHER INFORMATION: nucleic acid encoding stabilized peptide

<400> SEQUENCE: 91
agatctatgc agcaggagca cgagcaaggc aggatgagca agaggatgaa gaataataag      60
aattctcatg tttga                                                      75

<210> SEQ ID NO 92
<211> LENGTH: 22
<212> TYPE: PRT
<213> ORGANISM: ARTIFICIAL
<220> FEATURE:
<223> OTHER INFORMATION: stabilized peptide

<400> SEQUENCE: 92

Met Gln Gln Glu His Glu Gln Gly Arg Met Ser Lys Arg Met Lys Asn
1               5                   10                  15

Asn Lys Asn Ser His Val
            20

<210> SEQ ID NO 93
<211> LENGTH: 75
<212> TYPE: DNA
<213> ORGANISM: ARTIFICIAL
<220> FEATURE:
<223> OTHER INFORMATION: nucleic acid encoding stabilized peptide

<400> SEQUENCE: 93
agatctatga accatcataa tgaggccatg atcaacacaa tgaaaacgag gaataataag      60
aattctcatg tttga                                                      75

<210> SEQ ID NO 94
<211> LENGTH: 22
<212> TYPE: PRT
<213> ORGANISM: ARTIFICIAL
<220> FEATURE:
<223> OTHER INFORMATION: stabilized peptide
```

<400> SEQUENCE: 94

Met Asn His His Asn Glu Ala Met Ile Asn Thr Met Lys Thr Arg Asn
1               5                   10                  15

Asn Lys Asn Ser His Val
            20

<210> SEQ ID NO 95
<211> LENGTH: 72
<212> TYPE: DNA
<213> ORGANISM: ARTIFICIAL
<220> FEATURE:
<223> OTHER INFORMATION: nucleic acid encoding stabilized peptide

<400> SEQUENCE: 95
agatctatga acgacgacaa tcagcaagag gataatcatg atcagcataa ggataacaaa    60
taataagaat tc                                                       72

<210> SEQ ID NO 96
<211> LENGTH: 18
<212> TYPE: PRT
<213> ORGANISM: ARTIFICIAL
<220> FEATURE:
<223> OTHER INFORMATION: stabilized peptide

<400> SEQUENCE: 96

Met Asn Asp Asp Asn Gln Gln Glu Asp Asn His Asp Gln His Lys Asp
1               5                   10                  15

Asn Lys

<210> SEQ ID NO 97
<211> LENGTH: 72
<212> TYPE: DNA
<213> ORGANISM: ARTIFICIAL
<220> FEATURE:
<223> OTHER INFORMATION: nucleic acid encoding stabilized peptide

<400> SEQUENCE: 97
agatctatgc aagagcagga tcagcataat gataaccatc acgaggataa acataagaag    60
taataagaat tc                                                       72

<210> SEQ ID NO 98
<211> LENGTH: 18
<212> TYPE: PRT
<213> ORGANISM: ARTIFICIAL
<220> FEATURE:
<223> OTHER INFORMATION: stabilized peptide

<400> SEQUENCE: 98

Met Gln Glu Gln Asp Gln His Asn Asp Asn His His Glu Asp Lys His
1               5                   10                  15

Lys Lys

<210> SEQ ID NO 99
<211> LENGTH: 93
<212> TYPE: DNA
<213> ORGANISM: ARTIFICIAL
<220> FEATURE:
<223> OTHER INFORMATION: nucleic acid encoding stabilized peptide

<400> SEQUENCE: 99
agatctatgg aagacgaaga cgagggtgcg tcagcgtggg gagcagaact ttggtcgtgg    60
cagtcggtgc gtaaacgtaa ataataagaa ttc                                93

<210> SEQ ID NO 100
<211> LENGTH: 25
<212> TYPE: PRT
<213> ORGANISM: ARTIFICIAL
<220> FEATURE:
<223> OTHER INFORMATION: stabilized peptide

<400> SEQUENCE: 100

Met Glu Asp Glu Asp Glu Gly Ala Ser Ala Trp Gly Ala Glu Leu Trp
1               5                   10                  15

Ser Trp Gln Ser Val Arg Lys Arg Lys
            20                  25

<210> SEQ ID NO 101
<211> LENGTH: 93
<212> TYPE: DNA
<213> ORGANISM: ARTIFICIAL
<220> FEATURE:
<223> OTHER INFORMATION: nucleic acid encoding stabilized peptide

<400> SEQUENCE: 101
agatctatgg aagacgaaga cggtctaggc atgggggggtg ggttggtcag gctcacttta    60
ttattcttcc gtaaacgtaa ataataagaa ttc                                  93

<210> SEQ ID NO 102
<211> LENGTH: 25
<212> TYPE: PRT
<213> ORGANISM: ARTIFICIAL
<220> FEATURE:
<223> OTHER INFORMATION: stabilized peptide

<400> SEQUENCE: 102

Met Glu Asp Glu Asp Gly Leu Gly Met Gly Gly Gly Leu Val Arg Leu
1               5                   10                  15

Thr Leu Leu Phe Phe Arg Lys Arg Lys
            20                  25

<210> SEQ ID NO 103
<211> LENGTH: 93
<212> TYPE: DNA
<213> ORGANISM: ARTIFICIAL
<220> FEATURE:
<223> OTHER INFORMATION: nucleic acid encoding stabilized peptide

<400> SEQUENCE: 103
agatctatgg aagacgaaga cggggagagg atccaggggg cccgctgtcc agtagcgctg    60
gtagatagac gtaaacgtaa ataataagaa ttc                                  93

<210> SEQ ID NO 104
<211> LENGTH: 25
<212> TYPE: PRT
<213> ORGANISM: ARTIFICIAL
<220> FEATURE:
<223> OTHER INFORMATION: stabilized peptide

<400> SEQUENCE: 104

Met Glu Asp Glu Asp Gly Glu Arg Ile Gln Gly Ala Arg Cys Pro Val
1               5                   10                  15

Ala Leu Val Asp Arg Arg Lys Arg Lys
            20                  25

<210> SEQ ID NO 105
<211> LENGTH: 11
<212> TYPE: PRT

```
<213> ORGANISM: ARTIFICIAL
<220> FEATURE:
<223> OTHER INFORMATION: stabilized peptide

<400> SEQUENCE: 105

Met Glu Asp Glu Asp Arg Gly Arg Gly Arg
1               5                   10

<210> SEQ ID NO 106
<211> LENGTH: 93
<212> TYPE: DNA
<213> ORGANISM: ARTIFICIAL
<220> FEATURE:
<223> OTHER INFORMATION: nucleic acid encoding stabilized peptide

<400> SEQUENCE: 106
agatctatgg aagacgaaga cgacaggggg cgtgggcggt agctttaagt tgcgctaagt      60
tgcgagatac gtaaacgtaa ataataagaa ttc                                  93

<210> SEQ ID NO 107
<211> LENGTH: 93
<212> TYPE: DNA
<213> ORGANISM: ARTIFICIAL
<220> FEATURE:
<223> OTHER INFORMATION: nucleic acid encoding stabilized peptide

<400> SEQUENCE: 107
agatctatgg aagacgaaga cggggggggcc gggaggagtg cctgtctttg ttccgcgctt      60 gttgggaac gtaaacgtaa ataataagaa ttc                                   93

<210> SEQ ID NO 108
<211> LENGTH: 25
<212> TYPE: PRT
<213> ORGANISM: ARTIFICIAL
<220> FEATURE:
<223> OTHER INFORMATION: stabilized peptide

<400> SEQUENCE: 108

Met Glu Asp Glu Asp Gly Gly Ala Gly Arg Arg Ala Cys Leu Cys Ser
1               5                   10                  15

Ala Leu Val Gly Glu Arg Lys Arg Lys
            20                  25

<210> SEQ ID NO 109
<211> LENGTH: 90
<212> TYPE: DNA
<213> ORGANISM: ARTIFICIAL
<220> FEATURE:
<223> OTHER INFORMATION: nucleic acid encoding stabilized peptide

<400> SEQUENCE: 109
agatctatgg aagacgaaga caagcgtcgc gagaggagtg caaaagggcg tcatgtcggt      60
cggtcgatgc gtaaacgtaa ataagactgt                                      90

<210> SEQ ID NO 110
<211> LENGTH: 25
<212> TYPE: PRT
<213> ORGANISM: ARTIFICIAL
<220> FEATURE:
<223> OTHER INFORMATION: stabilized peptide

<400> SEQUENCE: 110

Met Glu Asp Glu Asp Lys Arg Arg Glu Arg Ser Ala Lys Gly Arg His
1               5                   10                  15
```

```
Val Gly Arg Ser Met Arg Lys Arg Lys
            20                  25

<210> SEQ ID NO 111
<211> LENGTH: 17
<212> TYPE: PRT
<213> ORGANISM: ARTIFICIAL
<220> FEATURE:
<223> OTHER INFORMATION: a-helical moiety

<400> SEQUENCE: 111

Asp Trp Leu Lys Ala Arg Val Glu Gln Glu Leu Gln Ala Leu Glu Ala
1               5                   10                  15

Arg

<210> SEQ ID NO 112
<211> LENGTH: 20
<212> TYPE: PRT
<213> ORGANISM: ARTIFICIAL
<220> FEATURE:
<223> OTHER INFORMATION: peptide from neuropeptide Y

<400> SEQUENCE: 112

Ala Glu Asp Leu Ala Arg Tyr Tyr Ser Ala Leu Arg His Tyr Ile Asn
1               5                   10                  15

Leu Ile Thr Arg
            20

<210> SEQ ID NO 113
<211> LENGTH: 21
<212> TYPE: PRT
<213> ORGANISM: ARTIFICIAL
<220> FEATURE:
<223> OTHER INFORMATION: peptide from human mannose binding protein

<400> SEQUENCE: 113

Ala Ala Ser Glu Arg Lys Ala Leu Gln Thr Glu Met Ala Arg Ile Lys
1               5                   10                  15

Lys Ala Leu Thr Ala
            20

<210> SEQ ID NO 114
<211> LENGTH: 24
<212> TYPE: PRT
<213> ORGANISM: ARTIFICIAL
<220> FEATURE:
<223> OTHER INFORMATION: peptide from helodermin

<400> SEQUENCE: 114

Ala Ile Phe Thr Glu Glu Tyr Ser Lys Leu Leu Ala Lys Leu Ala Leu
1               5                   10                  15

Gln Lys Tyr Leu Ala Ser Ile Leu
            20

<210> SEQ ID NO 115
<211> LENGTH: 34
<212> TYPE: PRT
<213> ORGANISM: ARTIFICIAL
<220> FEATURE:
<223> OTHER INFORMATION: peptide from ribosomal protein L9

<400> SEQUENCE: 115

Pro Ala Asn Leu Lys Ala Leu Glu Ala Gln Lys Gln Lys Glu Gln Arg
1               5                   10                  15

Gln Ala Ala Glu Glu Leu Ala Asn Ala Lys Lys Leu Lys Glu Gln Leu
```

-continued

```
            20              25              30
Glu Lys
```

STABILIZED BIOACTIVE PEPTIDES AND METHODS OF IDENTIFICATION, SYNTHESIS, AND USE

CROSS-REFERENCE TO RELATED APPLICATIONS

This application is a continuation of U.S. Ser. No. 11/213,668, filed 26 Aug. 2005 issued as U.S. Pat. No. 7,365,162 on Apr. 23, 2008), which is a continuation of U.S. Ser. No. 10/210,023, filed 31 Jul. 2002 (now abandoned), which is a continuation-in-part of U.S. Ser. No. 09/701,947, filed Dec. 5, 2000 (issued as U.S. Pat. No. 6,818,611 on Nov. 16, 2004), which is a National Stage application under 35 U.S.C. §371 PCT/US99/23731, filed Oct. 12, 1999 (published as WO/0022112 on Apr. 20, 2000), which in turn claims the benefit of U.S. Provisional Patent Applications Serial Nos. 60/104,013, filed Oct. 13, 1998, and 60/112,150, filed Dec. 14, 1998, each of which is incorporated herein by reference in its entirety.

TECHNICAL FIELD

This invention relates to stabilized bioactive peptides, and more particularly to bioactive peptides that contain heterologous stabilizing groups attached to one or both of the bioactive peptide's termini.

BACKGROUND

Bioactive peptides are small peptides that elicit a biological activity. Since the discovery of secretin in 1902, over 500 of these peptides which average 20 amino acids in size have been identified and characterized. They have been isolated from a variety of systems, exhibit a wide range of actions, and have been utilized as therapeutic agents in the field of medicine and as diagnostic tools in both basic and applied research. Tables 1 and 2 list some of the best known bioactive peptides.

TABLE 1

Bioactive peptides utilized in medicine

| Name | Isolated From | Size in Amino Acids | Therapeutic Use |
|---|---|---|---|
| Angiotensin II | Human Plasma | 8 | Vasoconstrictor |
| Bradykinin | Human Plasma | 9 | Vasodilator |
| Caerulein | From Skin | 10 | Choleretic Agent |
| Calcitonin | Human Parathyroid Gland | 32 | Calcium Regulator |
| Cholecystokinin | Porcine Intestine | 33 | Choleretic Agent |
| Corticotropin | Porcine Pituitary Gland | 39 | Hormone |
| Eledoisin | Octopod Venom | 11 | Hypotensive Agent |
| Gastrin | Porcine Stomach | 17 | Gastric Activator |
| Glucagon | Porcine Pancreas | 29 | Antidiabetic Agent |
| Gramicidin D | *Bacillus brevis* Bacteria | 11 | Antibacterial Agent |
| Insulin | Canine Pancreas | | Antidiabetic Agent |
| Insulin A | | 21 | |
| Insulin B | | 30 | |
| Kallidin | Human Plasma | 10 | Vasodilator |
| Luteinizing Hormone-Releasing Factor | Bovine Hypothalamus | 10 | Hormone Stimulator |
| Melittin | Bee Venom | 26 | Antirheumatic Agent |
| Oxytocin | Bovine Pituitary Gland | 9 | Oxytocic Agent |
| Secretin | Canine Intestine | 27 | Hormone |
| Sermorelin | Human Pancreas | 29 | Hormone Stimulator |
| Somatostatin | Bovine Hypothalamus | 14 | Hormone Inhibitor |
| Vasopressin | Bovine Pituitary Gland | 9 | Antidiuretic Agent |

TABLE 2

Bioactive peptides utilized in applied research

| Name | Isolated From | Size in Amino Acids | Biological Activity |
|---|---|---|---|
| Atrial Natriuretic Peptide | Rat Atria | 28 | Natriuretic Agent |
| Bombesin | Frog Skin | 14 | Gastric Activator |
| Conantokin G | Snail Venom | 17 | Neurotransmitter |
| Conotoxin G1 | Snail Venom | 13 | Neuromuscular Inhibitor |
| Defensin HNP-1 | Human Neutrophils | 30 | Antimicrobial Agent |
| Delta Sleep-Inducing Peptide | Rabbit Brain | 9 | Neurological Affector |
| Dermaseptin | Frog Skin | 34 | Antimicrobial Agent |
| Dynorphin | Porcine Brain | 17 | Neurotransmitter |
| EETI II | *Ecballium elaterium* seeds | 29 | Protease Inhibitor |
| Endorphin | Human Brain | 30 | Neurotransmitter |
| Enkephalin | Human Brain | 5 | Neurotransmitter |
| Histatin 5 | Human Saliva | 24 | Antibacterial Agent |
| Mastoparan | Vespid Wasps | 14 | Mast Cell Degranulator |
| Magainin 1 | Frog Skin | 23 | Antimicrobial Agent |
| Melanocyte Stimulating Hormone | Porcine Pituitary Gland | 13 | Hormone Stimulator |
| Motilin | Canine Intestine | 22 | Gastric Activator |
| Neurotensin | Bovine Brain | 13 | Neurotransmitter |
| Physalaemin | Frog Skin | 11 | Hypotensive Agent |
| Substance P | Horse Intestine | 11 | Vasodilator |
| Vasoactive Intestinal Peptide | Porcine Intestine | 28 | Hormone |

Where the mode of action of these peptides has been determined, it has been found to be due to the interaction of the bioactive peptide with a specific protein target. In most of the cases, the bioactive peptide acts by binding to and inactivating its protein target with extremely high specificities. Binding constants of these peptides for their protein targets typically have been determined to be in the nanomolar (nM, $10^{-9}$ M) range with binding constants as high as $10^{-12}$ M (picomolar range) having been reported. Table 3 shows target proteins inactivated by several different bioactive peptides as well as the binding constants associated with binding thereto.

TABLE 3

Binding constants of bioactive peptides

| Bioactive Peptide | Size in Amino Acids | Inhibited Protein | Binding Constant |
|---|---|---|---|
| α-Conotoxin GIA | 15 | Nicotinic Acetylcholine | $1.0 \times 10^{-9}$ M |
| EETI II | 29 | Trypsin | $1.0 \times 10^{-12}$ M |

TABLE 3-continued

Binding constants of bioactive peptides

| Bioactive Peptide | Size in Amino Acids | Inhibited Protein | Binding Constant |
|---|---|---|---|
| H2 (7-5) | 8 | HSV Ribonucleotide Reductase | $3.6 \times 10^{-5}$M |
| Histatin 5 | 24 | Bacteroides gingivalis Protease | $5.5 \times 10^{-8}$M |
| Melittin | 26 | Calmodulin | $3.0 \times 10^{-9}$M |
| Myotoxin (29-42) | 14 | ATPase | $1.9 \times 10^{-5}$M |
| Neurotensin | 13 | Ni Regulatory Protein | $5.6 \times 10^{-11}$M |
| Pituitary Adenylate Cyclase Activating Polypeptide | 38 | Calmodulin | $1.5 \times 10^{-8}$M |
| PKI (5-24) | 20 | CAMP-Dependent Protein Kinase | $2.3 \times 10^{-9}$M |
| SCP (153-180) | 27 | Calpain | $3.0 \times 10^{-8}$M |
| Secretin | 27 | HSR G Protein | $3.2 \times 10^{-9}$M |
| Vasoactive Intestinal Peptide | 28 | GPRNI G Protein | $2.5 \times 10^{-9}$M |

Recently, there has been an increasing interest in employing synthetically derived bioactive peptides as novel pharmaceutical agents due to the impressive ability of the naturally occurring peptides to bind to and inhibit specific protein targets. Synthetically derived peptides could be useful in the development of new antibacterial, antiviral, and anticancer agents. Examples of synthetically derived antibacterial or antiviral peptide agents would be those capable of binding to and preventing bacterial or viral surface proteins from interacting with their host cell receptors, or preventing the action of specific toxin or protease proteins. Examples of anticancer agents would include synthetically derived peptides that could bind to and prevent the action of specific oncogenic proteins.

To date, novel bioactive peptides have been engineered through the use of two different in vitro approaches. The first approach produces candidate peptides by chemically synthesizing a randomized library of 6-10 amino acid peptides (J. Eichler et al., Med. Res. Rev. 15: 481-496 (1995); K. Lam, Anticancer Drug Des. 12:145-167 (1996); M. Lebl et al., Methods Enzymol. 289:336-392 (1997)). In the second approach, candidate peptides are synthesized by cloning a randomized oligonucleotide library into a Ff filamentous phage gene, which allows peptides that are much larger in size to be expressed on the surface of the bacteriophage (H. Lowman, Ann. Rev. Biophys. Biomol. Struct. 26: 401-424 (1997); G. Smith et al., et al. Meth. Enz. 217: 228-257 (1993)). To date, randomized peptide libraries up to 38 amino acids in length have been made, and longer peptides are likely achievable using this system. The peptide libraries that are produced using either of these strategies are then typically mixed with a preselected matrix-bound protein target. Peptides that bind are eluted, and their sequences are determined. From this information new peptides are synthesized and their inhibitory properties are determined. This is a tedious process that only screens for one biological activity at a time.

Although these in vitro approaches show promise, the use of synthetically derived peptides has not yet become a mainstay in the pharmaceutical industry. The primary obstacle remaining is that of peptide instability within the biological system of interest as evidenced by the unwanted degradation of potential peptide drugs by proteases and/or peptidases in the host cells. There are three major classes of peptidases which can degrade larger peptides: amino and carboxy exopeptidases which act at either the amino or the carboxy terminal end of the peptide, respectively, and endopeptidases which act on an internal portion of the peptide. Aminopeptidases, carboxypeptidases, and endopeptidases have been identified in both prokaryotic and eukaryotic cells. Many of those that have been extensively characterized were found to function similarly in both cell types. Interestingly, in both prokaryotic and eukaryotic systems, many more aminopeptidases than carboxypeptidases have been identified to date.

Approaches used to address the problem of peptide degradation have included the use of D-amino acids or modified amino acids as opposed to the naturally occurring L-amino acids (e.g., J. Eichler et al., Med Res Rev. 15:481 496 (1995); L. Sanders, Eur. J. Drug Metabol. Pharmacokinetics 15:95-102 (1990)), the use of cyclized peptides (e.g., R. Egleton, et al., Peptides 18:1431-1439 (1997)), and the development of enhanced delivery systems that prevent degradation of a peptide before it reaches its target in a patient (e.g., L. Wearley, Crit. Rev. Ther. Drug Carrier Syst. 8:331-394 (1991); L. Sanders, Eur. J. Drug Metabol. Pharmacokinetics 15: 95-102 (1990)). Although these approaches for stabilizing peptides and thereby preventing their unwanted degradation in the biosystem of choice (e.g., a patient) are promising, there remains no way to routinely and reliably stabilize peptide drugs and drug candidates. Moreover, many of the existing stabilization and delivery methods cannot be directly utilized in the screening and development of novel useful bioactive peptides. A biological approach that would serve as both a method of stabilizing peptides and a method for identifying novel bioactive peptides would represent a much needed advance in the field of peptide drug development.

SUMMARY OF THE INVENTION

The present invention provides an intracellular screening method for identifying novel bioactive peptides. A host cell is transformed with an expression vector comprising a tightly regulable control region operably linked to a nucleic acid sequence encoding a peptide. Typically, the encoded peptide has a stabilizing group positioned at one or both ends of the peptide. The transformed host cell is first grown under conditions that repress expression of the peptide and then, subsequently, expression of the peptide is induced. Phenotypic changes in the host cell upon expression of the peptide are indicative of bioactivity, and are evaluated. If, for example, expression of the peptide is accompanied by complete or partial inhibition of host cell growth, the expressed peptide constitutes a bioactive peptide, in that it functions as an inhibitory peptide.

Intracellular identification of bioactive peptides can be advantageously carried out in a pathogenic microbial host cell. Bioactive peptides having antimicrobial activity are readily identified in a microbial host cell system. Further, the method can be carried out in a host cell that has not been modified to reduce or eliminate the expression of naturally expressed proteases or peptidases. When carried out in a host cell comprising proteases and peptidases, the selection process of the invention is biased in favor of bioactive peptides that are protease and peptidase-resistant.

The tightly regulable control region of the expression vector used to transform the microbial host cell according to the invention can be derived from the wild-type Escherichia coli lac operon, and the transformed host cell can include an amount of Lac repressor protein effective to repress expression of the peptide during host cell growth under repressed conditions. To insure a sufficient amount of Lac repressor protein, the host cell can be transformed with a second vector that overproduces Lac repressor protein.

Optionally, the expression vector used to transform the host cell can be genetically engineered to encode a stabilized peptide that is resistant to peptidases and proteases. For example, the coding sequence can be designed to encode a stabilizing group at either or both of the peptide's N-terminus or C-terminus. As another example, the coding sequence can be designed to encode a stabilizing motif such as an α-helix motif or an opposite charge ending motif, as described below. The presence of a stabilizing group at a peptide terminus and/or of a stabilizing motif can slow down the rate of intracellular degradation of the peptide.

A plurality of vectors can be used to screen a randomized library of candidate bioactive peptides.

The present invention also provides a polypeptide that includes a bioactive peptide and a stabilizing group coupled to at least one terminus of the bioactive peptide. Preferably, the bioactive peptide is 50 or fewer amino acids in length. The stabilizing group is heterologous to the bioactive peptide and can be, for example, a proline, a proline-containing peptide, a single α-helix or multiple helix bundle, or other polypeptide or small protein such as Rop, human serum albumin, and the like. In one embodiment of the stabilized polypeptide, the stabilizing group(s) lack the capacity to participate in the formation of an intramolecular disulfide bond within the polypeptide. Thus, the stabilizing group is preferably not a thioredoxin polypeptide.

When a polypeptide includes a stabilizing group on each terminus, the stabilizing groups can be the same or different. If different, the stabilizing groups are optionally heterologous to each other, as that term is defined below. The first and second stabilizing groups can, but need not, interact to form a naturally occurring secondary or tertiary structure. Further, the first and second stabilizing groups can, but need not, confine the N-terminus and the C-terminus of the bioactive peptide in close proximity.

The invention further includes a nucleic acid encoding the polypeptide of the invention. A vector that contains such a nucleic acid is also included. Preferably the vector contains a tightly regulable expression control sequence operably linked to the nucleic acid sequence encoding the stabilized polypeptide.

The present invention also includes a method for making a stabilized polypeptide that involves coupling a stabilizing group to at least one terminus of a bioactive peptide. Coupling can be achieved chemically or enzymatically, or can occur as the result of translation in a host cell of a vector containing a nucleic acid sequence encoding the stabilized polypeptide. The vector comprises an expression control sequence operably linked to the coding sequence; preferably, the expression control sequence is tightly regulable in said host cell. Optionally the method includes determining stability of said stabilized polypeptide relative to said bioactive peptide.

When the method is performed in a host cell, the host cell is first transformed with an exogenous nucleic acid encoding the stabilized polypeptide, then the stabilized polypeptide is expressed and recovered. The host cells can be prokaryotic, such as bacteria, or eukaryotic.

Phage display can be used to identify a bioactive peptide that can be subsequently stabilized according to the invention. When displayed on the surface of a bacteriophage, bioactive peptides are tethered at one end by a bacteriophage protein. The free bioactive peptide (i.e., uncoupled from the bacteriophage protein) may exhibit a lack of stability in vivo. Hence, the invention involves stabilizing these bioactive peptides by coupling them to a stabilizing group at the end that had been tethered during phage display, thereby effectively replacing the bacteriophage protein as a stabilizing feature. Coupling can take place chemically, enzymatically, or by way of recombinant genetic engineering, as described herein. Polypeptides thus stabilized are also included in the invention.

Alternatively, the stabilized polypeptide can be produced as a direct product of phage display. A bacteriophage that contains an exogenous nucleic acid encoding a polypeptide comprising a bioactive peptide (or candidate bioactive peptide), a bacteriophage protein coupled to one terminus of the bioactive peptide, and a stabilizing group coupled to the other terminus of the bioactive peptide is cultured under conditions to cause the bacteriophage to express the stabilized polypeptide and display it on its surface. The stabilizing group can be coupled to either end of the bioactive peptide, and the bacteriophage protein is coupled to the other end. Optionally the stabilized polypeptide is cleaved from the host cell surface to yield a stabilized bioactive peptide comprising the bioactive peptide and the stabilizing group.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

BRIEF DESCRIPTION OF THE DRAWINGS

FIG. 1 shows the control region (SEQ ID NO: 1) of the wild-type lac operon from the auxiliary operator O3 through the translational start of the lacZ gene. DNA binding sites include the operators O3 and O1 (both underlined), catabolite gene activator protein (CAP) (boxed), the −35 site (boxed), and the −10 site (boxed), while important RNA and protein sites include the LacI translation stop site (TGA), the +1 lacZ transcription start site, the Shine Dalgarno (SD) ribosome binding site for lacZ, and the LacZ translation start site (ATG).

FIG. 9 illustrates a peptide (SEQ ID NO:2) having the opposite charge ending motif, wherein the amino and carboxy termini of the peptide are stabilized by the interactions of the opposite charge ending amino acids.

DETAILED DESCRIPTION

Figure 2:
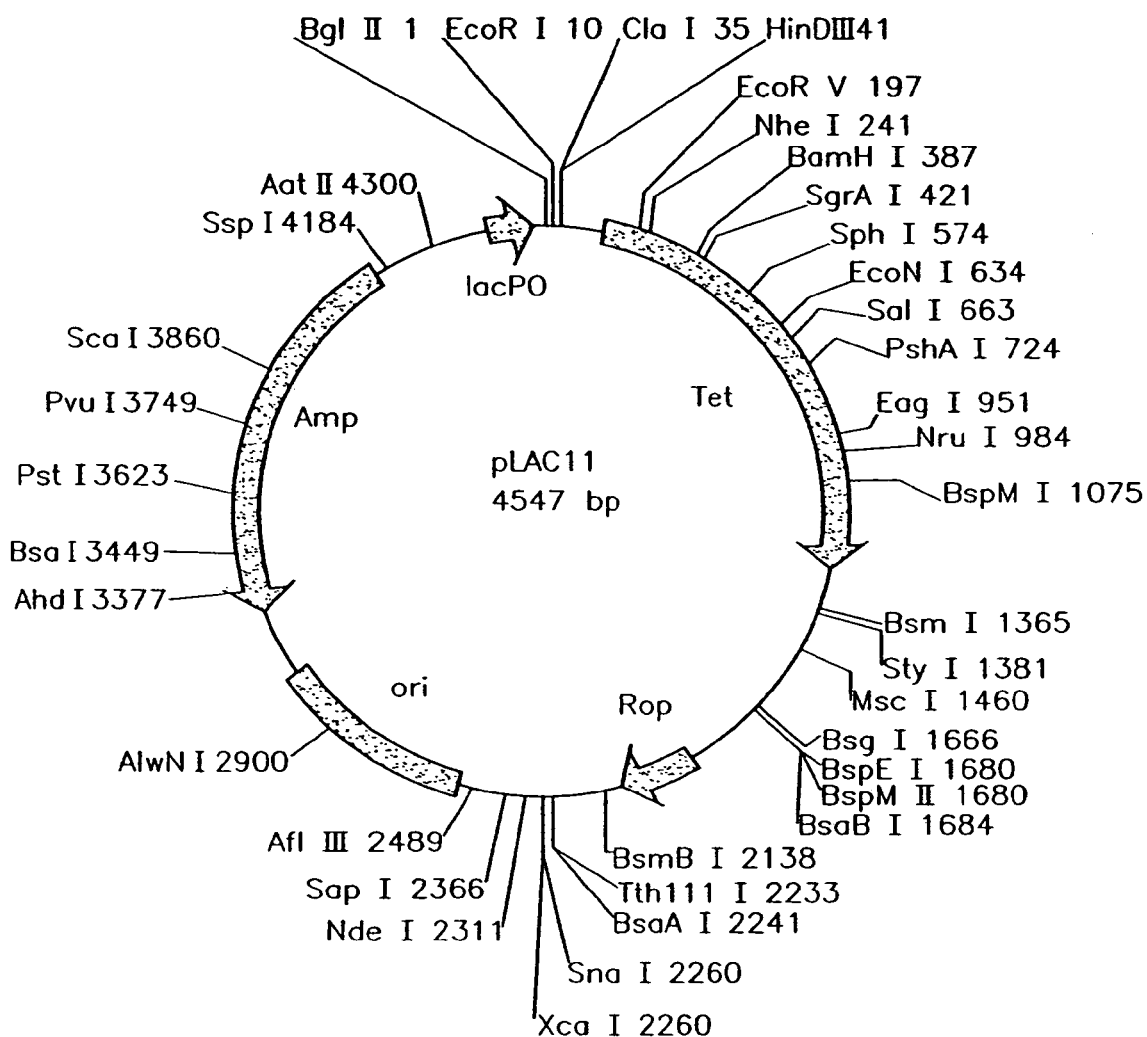
FIG. 2 is a map of plasmid pLAC11. The unique restriction sites and the base pair at which they cut are indicated. Other sites of interest are also shown, including Tet (98-1288), Rop (1931-2122), origin of replication (ori) (2551-3138), Amp (3309-25 4 169), and lacPO (4424-4536).

The present invention represents a significant advance in the art of peptide drug development by allowing concurrent screening for peptide bioactivity and stability. Randomized recombinant peptides are screened for bioactivity in a tightly regulated inducible expression system that permits essentially complete repression of peptide expression in the host cell. Subsequent induction of peptide expression can then be used to identify peptides that inhibit host cell growth or possess other bioactivities.

Intracellular screening of randomized peptides has many advantages over existing methods. Bioactivity is readily apparent, many diverse bioactivities can be screened for simultaneously, very large numbers of peptides can be screened using easily generated peptide libraries, and the host cell, if desired, can be genetically manipulated to identify an affected protein target. Advantageously, randomized peptides can be screened in a host cell that is identical to or closely resembles the eventual target cell for antimicrobial, anticancer, and other therapeutic applications. An additional and very important feature of this system is that selection is naturally biased in favor of peptides that are stable in an intracellular environment, i.e., that are resistant to proteases and peptidases. Fortuitously, bacterial peptidases are very similar to eukaryotic peptidases. Peptides that are stable in a bacterial host are thus likely to be stable in a eukaryotic cell as well, allowing bacterial cells to be used in initial screens to identify drugs that may eventually prove useful as human or animal therapeutics.

The invention is directed to the identification and use of bioactive peptides. A bioactive peptide is a peptide having a biological activity. The term "bioactivity" as used herein includes, but is not limited to, any type of interaction with another biomolecule, such as a protein, glycoprotein, carbohydrate, for example an oligosaccharide or polysaccharide, nucleotide, polynucleotide, fatty acid, hormone, enzyme, cofactor or the like, whether the interactions involve covalent or noncovalent binding. Bioactivity further includes interactions of any type with other cellular components or constituents including salts, ions, metals, nutrients, foreign or exogenous agents present in a cell such as viruses, phage and the like, for example binding, sequestration or transport-related interactions. Bioactivity of a peptide can be detected, for example, by observing phenotypic effects in a host cell in which it is expressed, or by performing an in vitro assay for a particular bioactivity, such as affinity binding to a target molecule, alteration of an enzymatic activity, or the like. Examples of bioactive peptides include antimicrobial peptides and peptide drugs. Antimicrobial peptides are peptides that adversely affect a microbe such as a bacterium, virus, protozoan, or the like. Antimicrobial peptides include, for example, inhibitory peptides that slow the growth of a microbe, microbiocidal peptides that are effective to kill a microbe (e.g., bacteriocidal and virocidal peptide drugs, sterilants, and disinfectants), and peptides effective to interfere with microbial reproduction, host toxicity, or the like. Peptide drugs for therapeutic use in humans or other animals include, for example, antimicrobial peptides that are not prohibitively toxic to the patient, and peptides designed to elicit, speed up, slow down, or prevent various metabolic processes in the host such as insulin, oxytocin, calcitonin, gastrin, somatostatin, anticancer peptides, and the like.

The term "peptide" as used herein refers to a plurality of amino acids joined together in a linear chain via peptide bonds. Accordingly, the term "peptide" as used herein includes a dipeptide, tripeptide, oligopeptide and polypeptide. A dipeptide contains two amino acids; a tripeptide contains three amino acids; and the term oligopeptide is typically used to describe peptides having between 2 and about 50 or more amino acids. Peptides larger than about 50 are often referred to as polypeptides or proteins. For purposes of the present invention, a "peptide" is not limited to any particular number of amino acids. Preferably, however, the peptide contains about 2 to about 50 amino acids (e.g., about 5 to about 40 amino acids, about 5 to about 20 amino acids, or about 7 to 15 amino acids).

The library used to transform the host cell is formed by cloning a randomized, peptide-encoding oligonucleotide into a nucleic acid construct having a tightly regulable expression control region. An expression control region can be readily evaluated to determine whether it is "tightly regulable," as the term is used herein, by bioassay in a host cell engineered to contain a mutant nonfunctional gene "X." Transforming the engineered host cell with an expression vector containing a tightly regulable expression control region operably linked to a cloned wild-type gene "X" will preserve the phenotype of the engineered host cell under repressed conditions. Under induced conditions, however, the expression vector containing the tightly regulable expression control region that is operably linked to the cloned wild-type gene "X" will complement the mutant nonfunctional gene X to yield the wild-type phenotype. In other words, a host cell containing a null mutation which is transformed with a tightly regulable expression vector capable of expressing the chromosomally inactivated gene will exhibit the null phenotype under repressed conditions; but when expression is induced, the cell will exhibit a phenotype indistinguishable from the wild-type cell. It should be understood that the expression control region in a tightly regulable expression vector of the present invention can be readily modified to produce higher levels of an encoded biopeptide, if desired (see, e.g., Example 1, below). Such modification may unavoidably introduce some "leakiness" into expression control, resulting in a low level of peptide expression under repressed conditions.

In one embodiment, the expression control region of the inducible expression vector is derived from the wild-type *E. coli* lac promoter/operator region. The expression vector can contain a regulatory region that includes the auxiliary operator O3, the CAP binding region, the −35 promoter site, the −10 promoter site, the operator O1, the Shine-Dalgarno sequence for lacZ, and a spacer region between the end of the Shine-Dalgarno sequence and the ATG start of the lacZ coding sequence (see FIG. 1).

It is to be understood that variations in the wild-type nucleic acid sequence of the lac promoter/operator region can be tolerated in the expression control region of the preferred expression vector and are encompassed by the invention, provided that the expression control region remains tightly regulable as defined herein. For example, the −10 site of the wild-type icac operon (TATGTT) is weak compared to the bacterial consensus −10 site sequence TATAAT, sharing four out of six positions. It is contemplated that other comparably weak promoters are equally effective at the −10 site in the expression control region; a strong promoter is to be avoided in order to insure complete repression in the uninduced state. With respect to the −35 region, the sequence of the wild-type lac operon, TTTACA, is one base removed from the consensus −35 sequence TTGACA. It is contemplated that a tightly regulable lac operon-derived expression control region could be constructed using a weaker −35 sequence (i.e., one having less identity with the consensus −35 sequence) and a wild-type −10 sequence (TATAAT), yielding a weak promoter that needs the assistance of the CAP activator protein. Similarly, it is to be understood that the nucleic acid sequence of the CAP binding region can be altered as long as the CAP protein binds to it with essentially the same affinity. The spacer region between the end of the Shine-Dalgarno sequence and the ATG start of the lacZ coding sequence is typically between about 5 and about 10 nucleotides in length, preferably about 5 to about 8 nucleotides in length, more preferably about 7-9 nucleotides in length. The most preferred composition and length of the spacer region depends on the composition and length of Shine-Dalgarno sequence with which it is operably linked as well as the translation start codon employed (i.e., AUG, GUG, or UUG), and can be determined accordingly by one of skill in the art. Preferably the nucleotide composition of the spacer region is "AT rich"; that is, it contains more A's and T's than it does G's and C's.

In one embodiment of the method of the invention, the expression vector has the identifying characteristics of pLAC 11 (ATCC No. 207108) and, in a particularly convenient embodiment, is pLAC 11 (ATCC No. 207108).

As used in the present invention, the term "vector" is to be broadly interpreted as including a plasmid, including an episome, a viral vector, a cosmid, or the like. A vector can be circular or linear, single-stranded or double-stranded, and can comprise RNA, DNA, or modifications and combinations thereof. Selection of a vector or plasmid backbone depends upon a variety of characteristics desired in the resulting construct, such as selection marker(s), plasmid copy number, and the like. A nucleic acid sequence is "operably linked" to an expression control sequence in the regulatory region of a vector, such as a promoter, when the expression control sequence controls or regulates the transcription and/or the translation of that nucleic acid sequence. A nucleic acid that is "operably linked" to an expression control sequence includes, for example, an appropriate start signal (e.g., ATG) at the beginning of the nucleic acid sequence to be expressed and a reading frame that permits expression of the nucleic acid sequence under control of the expression control sequence to yield production of the encoded peptide. The regulatory region of the expression vector optionally includes a termination sequence, such as a codon for which there is no corresponding aminoacetyl-tRNA, thus ending peptide synthesis. Typically, when the ribosome reaches a termination sequence or codon during translation of the mRNA, the polypeptide is released and the ribosome-mRNA-tRNA complex dissociates.

An expression vector optionally includes one or more selection or marker sequences, which typically encode an enzyme capable of inactivating a compound in the growth medium. The inclusion of a marker sequence can, for example, render the host cell resistant to an antibiotic, or it can confer a compound-specific metabolic advantage on the host cell. Markers such as green fluorescent protein also can be used to monitor growth or toxicity in host cells in which it is expressed. Cells can be transformed with the expression vector using any convenient method known in the art, including chemical transformation, e.g., whereby cells are made competent by treatment with reagents such as $CaCl_2$; electroporation and other electrical techniques; microinjection and the like.

The vector may further include a tightly regulable expression control sequence operably linked to the nucleic acid sequence encoding the polypeptide, particularly a stabilized polypeptide, as described herein. In embodiments of the method that use a tightly regulable expression system derived from the lac operon, the host cell is or has been genetically engineered or otherwise altered to contain a source of Lac repressor protein in excess of the amount produced in wild-type E. coli. A host cell that contains an excess source of Lac repressor protein is one that expresses an amount of Lac repressor protein sufficient to repress expression of the peptide under repressed conditions, i.e., in the absence of an inducing agent, such as isopropyl β-D-thiogalactoside (IPTG). Preferably, expression of Lac repressor protein is constitutive. For example, the host cell can be transformed with a second vector comprising a gene encoding Lac repressor protein, preferably lacI, more preferably $lacI^q$, to provide an excess source of Lac repressor protein in trans, i.e., extraneous to the tightly regulable expression vector. An episome can also serve as a trans source of Lac repressor. Another option for providing a trans source of Lac repressor protein is the host chromosome itself, which can be genetically engineered to express excess Lac repressor protein. Alternatively, a gene encoding Lac repressor protein can be included on the tightly regulable expression vector that contains the peptide-encoding oligonucleotide so that Lac repressor protein is provided in cis. The gene encoding the Lac repressor protein is preferably under the control of a constitutive promoter.

The invention is not limited by the type of host cell used for screening. The host cell can be a prokaryotic or a eukaryotic cell. Preferred mammalian cells include human cells, of any tissue type, and can include cancer cells or cell lines (e.g., HeLa cells) or other immortalized cell lines, hybridomas, pluripotent or omnipotent cells such as stem cells or cord blood cells, etc., without limitation. Preferred yeast host cells include Saccharomyces cerevisiae and Schizosaccharomyces pombe. Preferred bacterial host cells include gram negative bacteria, such as E. coli and various Salmonella spp., and gram positive bacteria, such as bacteria from the genera Staphylococcus, Streptococcus and Enterococcus. Protozoan cells are also suitable host cells. In clear contrast to conventional recombinant protein expression systems, it is preferable that the host cell contains proteases and/or peptidases, since the selection will, as a result, be advantageously biased in favor of peptides that are protease- and peptidase-resistant. More preferably, the host cell has not been modified, genetically or otherwise, to reduce or eliminate the expression of any naturally expressed proteases or peptidases. The host cell can be selected with a particular purpose in mind. For example, if it is desired to obtain peptide drugs specific to inhibit *Staphylococcus*, peptides can be advantageously expressed and screened in *Staphylococcus*.

There is, accordingly, tremendous potential for the application of this technology in the development of new antibacterial peptides useful to treat various pathogenic bacteria. Of particular interest are pathogenic *Staphylococci, Streptococci*, and *Enterococci*, which are the primary causes of nosocomial infections. Many of these strains are becoming increasingly drug-resistant at an alarming rate. The technology of the present invention can be practiced in a pathogenic host cell to isolate inhibitor peptides that specifically target the pathogenic strain of choice. Inhibitory peptides identified using pathogenic microbial host cells in accordance with the invention may have direct therapeutic utility; based on what is known about peptide import, it is very likely that small peptides are rapidly taken up by *Staphylococci, Streptococci*, and *Enterococci*. Once internalized, the inhibitory peptides identified according to the invention would be expected to inhibit the growth of the bacteria in question. It is therefore contemplated that novel inhibitor peptides so identified can be used in medical treatments and therapies directed against microbial infection. It is further contemplated that these novel inhibitor peptides can be used, in turn, to identify additional novel antibacterial peptides using a synthetic approach. The coding sequence of the inhibitory peptides is determined, and peptides are then chemically synthesized and tested in the host cell for their inhibitory properties.

Novel inhibitor peptides identified in a pathogenic microbial host cell according to the invention can also be used to elucidate potential new drug targets. The protein target that the inhibitor peptide inactivated is identified using reverse genetics by isolating mutants that are no longer inhibited by the peptide. These mutants are then mapped in order to precisely determine the protein target that is inhibited. New antibacterial drugs can then be developed using various known or yet to be discovered pharmaceutical strategies.

Following transformation of the host cell, the transformed host cell is initially grown under conditions that repress expression of the peptide. Expression of the peptide is then induced. For example, when a lac promoter/operator system is used for expression, IPTG is added to the culture medium. A determination is subsequently made as to whether the peptide is inhibitory to host cell growth, wherein inhibition of host cell growth under induced but not repressed conditions is indicative of the expression of a bioactive peptide.

Alternatively, a vector encoding a marker such as green fluorescent protein (GFP) can be used to monitor toxicity of the random peptides in a host. In general, fluorescence can be monitored in cells that are expressing both GFP and a randomized peptide and compared with the fluorescence of control cells, i.e., cells expressing only GFP. If the randomized peptide is toxic to the host, fluorescence would not be observed or would be decreased relative to the control cells. Alternatively, GFP or other markers can be used to monitor the cells for complete or partial inhibition of cell division, or for induction of apoptosis.

For example, to identify a potential anticancer peptide, a cancer cell line such as the HeLa cell line can be used as the host. The cell line can be transfected with one or more vectors such that the cell line expresses both a marker (e.g., GFP) and a peptide from a library of random peptides. It should be noted that the nucleic acid sequences encoding the marker and the random peptides can be on the same or different vectors. Expression of the random peptides can be controlled by a tightly regulable control sequence, although this need not be the case. The transfected cells can be seeded into multi-well plates (e.g., 96-well plates) or into multiple flasks, with each well or plate receiving cells collectively expressing a single random peptide. In one embodiment, the number of cells seeded into each well or flask is chosen to ensure that an adequate number of cells expressing a random peptide and a marker is present in each well or flask. This can depend, for example, on the original transfection efficiency. Under these conditions, the marker will be observed in all wells or in each flask, unless a peptide that is being expressed is toxic to the cells or otherwise exhibits a desirable bioactivity (e.g., causes a complete or partial inhibition of cell division, or induces apoptosis). In wells in which fluorescence is not observed or the level of fluorescence is decreased, the random peptides are candidates for anti-cancer peptides. Candidate anti-cancer peptides identified by this method can be further screened to determine if the peptide is selectively toxic or otherwise bioactive in cancer cells. For example, the bioactivity can be compared between malignant and non-malignant cells using a 96-well screening format similar to that described above.

In a similar fashion, the method of the invention can be used to identify peptides that exert an agonist effect on cell division and growth. For example, stem cells and cord blood cells, which typically do not proliferate well, can be employed as the host cells. Candidate peptides can be assayed for a positive effect on cell division and growth. Agonistic peptides may be useful in wound healing, organ transplantation and cardiovascular applications.

A plurality of vectors (e.g., a library) that encode a population of randomized peptides can be used to identify bioactive peptides (e.g., antimicrobial or anticancer peptides). A library can include at least two different vectors (e.g., at least five, 50, 500, 5000, 50,000, 100,000, $1 \times 10^6$, $5 \times 10^6$ or more vectors), with each of the vectors encoding different, randomized peptides (e.g., at least five, 50, 500, 5000, 50,000, 100,000, $1 \times 10^6$, $5 \times 10^6$ or more different randomized peptides). Bioactive peptides can be identified by screening each of the randomized peptides encoded by the different vectors, for a desired bioactivity (e.g., cell toxicity). Randomized peptides that exhibit the desired bioactivity can be selected as bioactive peptides.

During development and testing of the intracellular screening method of the present invention, it was surprisingly discovered that several bioactive peptides identified from the randomized peptide library shared particular structural features. For example, a disproportionately high number of bioactive peptides identified using the intracellular screening method contained one or more proline residues at or near a peptide terminus. A disproportionate number also contained sequences predicted, using structure prediction algorithms well-known in the art, to form secondary structures such as a helices or sheets; or a hydrophobic membrane spanning domain. Bioactive fusion proteins comprising the randomized peptide sequence fused to the Rop protein, due to a deletion event in the expression vector, were also identified.

Accordingly, randomized peptides used in the screening method of the invention can be optionally engineered according to the method of the invention in a biased synthesis to increase their stability by making one or both of the N-terminal or C-terminal ends more resistant to proteases and peptidases. For example, a vector can include a nucleic acid sequence encoding a stabilized polypeptide, wherein the stabilized polypeptide includes a randomized peptide and a stabilizing group positioned at the N- and/or C-terminus of the randomized peptide. The resulting stabilized polypeptide includes the randomized peptide and the stabilizing group coupled to one or both of the randomized peptide's termini. By "coupled to . . . one or both . . . termini" it is meant that the randomized peptide is covalently linked, at one or both of its termini, to the stabilizing group. The nucleic acid sequence that encodes the randomized peptide in the expression vector or the expression vector itself is preferably modified such that a first stabilizing group is positioned at the N-terminus of the peptide, and a second stabilizing group is positioned at the C-terminus of the peptide.

Notably, the bioactive peptides identified according to the method of the invention are, by reason of the method itself, stable in the intracellular environment of the host cell. The method of the invention thus preferably identifies bioactive peptides that are resistant to proteases and peptidases. Resistance to proteases and peptidases can be evaluated by measuring peptide degradation when in contact with appropriate cell extracts (e.g., bacterial, yeast, or human cell extracts), employing methods well-known in the art. A bioactive peptide, without stabilization, can be used as a control. For example, degradation of a stabilized, biotinylated peptide can be assessed by electrophoresis through an SDS-polyacrylamide gel and Western blotting using an avidin-horseradish peroxidase conjugate. Alternatively, resistance to proteases and peptidases can be evaluated by measuring peptide degradation when in contact with purified peptidases and/or proteases (e.g., the Lon and Clp proteases from $E.$ $coli$). A protease- or peptidase-resistant peptide exhibits a longer half-life in the presence of proteases or peptidases compared to a control peptide.

In should be noted that the stabilization of peptides (e.g., polypeptides containing about 2 to about 50 amino acids) in accordance with the present invention is an unexpected as peptides, unlike proteins, are relatively unstable in physiological environments. For example, the half-life of most peptides in physiological environments is about 2 minutes, whereas the half-life of most proteins in physiological environments is typically well in excess of 2 minutes and is often measured in hours or days. Proteins possess an inherent stability as a result of complex intramolecular interactions wherein, due to "protein folding" sections of the polypeptide that are distant on the linear chain are close together in space resulting in tertiary and quaternary structure. Peptides, on the other hand, typically possess, at most, one or two secondary structural elements (e.g., α-helix, β-sheet or β-turn). Many peptides possess no apparent secondary structural elements at all.

Stabilizing groups are amino acid sequences that can range in size from a single amino acid to a polypeptide (>50 amino acids). Suitable stabilizing groups do not specifically bind to serum proteins (e.g., albumin) or immunoglobulins, and in many embodiments, are free of disulfide bonds. Thus, the stabilizing groups of the present invention directly stabilize the peptides to which they are attached. Stabilizing groups that do not elicit, or elicit only minimal (i.e., clinically acceptable), immune responses in subject mammals are particularly useful.

In one embodiment, the stabilizing group is a stable protein, preferably a small stable protein such as thioredoxin, glutathione sulfotransferase, maltose binding protein, glutathione reductase, or a four-helix bundle protein such as Rop protein, as described below, although no specific size limitation on the protein anchor is intended.

Proteins suitable for use as stabilizing groups can be either naturally occurring or non-naturally occurring. They can be isolated from an endogenous source, chemically or enzymatically synthesized, or produced using recombinant DNA technology. Proteins that are particularly well-suited for use as stabilizing groups are those that are relatively short in length and form very stable structures in solution. Proteins having molecular weights of less than about 70 kD (e.g., less than about 65, 60, 50, 40, 25, or 12 kD) are useful as stabilizing groups. For example, human serum albumin has a molecular weight of about 64 kD; $E.$ $coli$ thioredoxin has a molecular weight of about 11.7 kD; $E.$ $coli$ glutathione sulfotransferase has a molecular weight of about 22.9 kD; Rop from the ColE1 replicon has a molecular weight of about 7.2 kD; and maltose binding protein (without its signal sequence) has a molecular weight of about 40.7 kD. The small size of the Rop protein makes it especially useful as a stabilizing group, fusion partner, or peptide "anchor", in that it is less likely than larger proteins to interfere with the accessibility of the linked peptide, thus preserving its bioactivity. Rop's highly ordered anti-parallel four-helix bundle topology (after dimerization), slow unfolding kinetics (see, e.g., Betz et al, Biochemistry 36, 2450-2458 (1997)), and lack of disulfide bonds also contribute to its usefulness as a peptide anchor according to the invention. Other proteins with similar folding kinetics and/or thermodynamic stability (e.g., Rop has a midpoint temperature of denaturation, $T_m$, of about 71° C., Steif et al., Biochemistry 32, 3867-3876 (1993)) are also preferred peptide anchors.

Peptides or proteins having highly stable tertiary structures, such as a four-helix bundle topology as exemplified in Rop, are particularly useful. Thus, in another embodiment of the screening method of the invention, the expression vector encodes a stabilizing group comprising an α-helical moiety at the N-terminus, C-terminus, or both, of the randomized peptide. The resulting fusion protein is predicted to be more stable than the randomized peptide itself in the host intracellular environment. Suitable α-helical moieties can range from a single α-helix to two, three, four, or five α-helix bundles.

Non-limiting examples of single α-helical moieties that can be used to stabilize a bioactive peptide include the following: a 17 amino acid peptide based on the first α-helix of the α-helix/turn/α-helix peptide of Fezoui et al., Proc. Natl. Acad. Sci. USA 91, 3675-3679 (1994) (Asp-Trp-Leu-Lys-Ala-Arg-Val-Glu-Gln-Glu-Leu-Gln-Ala-Leu-Glu-Ala-Arg, SEQ ID NO:111); an 18 to 36 amino acid peptide containing only glutamic acid, lysine, and glutamine residues, such as (Glu-Lys-Gln)$_y$, where y is 6 to 12, although no specific arrangement of the three amino acids within the repeating tripeptide is intended; a 20 amino acid peptide containing amino acids 14-33 of Neuropeptide Y (Ala-Glu-Asp-Leu-Ala-Arg-Tyr-Tyr-Ser-Ala-Leu-Arg-His-Tyr-Ile-Asn-Leu-Ile-Thr-Arg, SEQ ID NO:112); a 21 amino acid peptide based on amino acids 88-108 of human mannose binding protein (Ala-Ala-Ser-Glu-Arg-Lys-Ala-Leu-Gln-Thr-Glu-Met-Ala-Arg-Ile-Lys-Lys-Ala-Leu-Thr-Ala, SEQ ID NO:113); a 24 amino acid peptide based on amino acids 4-27 of helodermin (Ala-Ile-Phe-Thr-Glu-Glu-Tyr-Ser-Lys-Leu-Leu-Ala-Lys-Leu-Ala-Leu-Gln-Lys-Tyr-Leu-Ala-Ser-Ile-Leu, SEQ ID NO:114); and a 34 amino acid peptide based on amino acids 41-74 of ribosomal protein L9 (Pro-Ala-Asn-Leu-Lys-Ala-Leu-Glu-Ala-Gln-Lys-Gln-Lys-Glu-Gln-Arg-Gln-Ala-Ala-Glu-Glu-Leu-Ala-Asn-Ala-Lys-Lys-Leu-Lys-Glu-Gln-Leu-Glu-Lys, SEQ ID NO: 115).

Non-limiting examples of two-helix bundles include two α-helices connected by a turn region (see, for example, the 38 amino acid α-helix/turn/α-helix peptide of Fezoui et al. (1994), supra); a 42 amino acid peptide based on amino acids 512-553 of the adhesion modulation domain (AMD) of α-catenin; a 64 amino acid peptide based on residues 411-475 of α-catenin; and a 78 amino acid a peptide based on residues 24-102 of seryl-tRNA synthetase from $E.$ $coli$.

Non-limiting examples of three-helix bundles include a peptide based on residues 410-504 of α-catenin, a (Gly-Pro-Pro-)$_{10}$ or (-Pro-Pro-Gly)$_{10}$ peptide, and an (Ala-Pro-Pro-)$_{10}$ or (-Pro-Pro-Ala)$_{10}$ peptide.

Two-helix bundles may dimerize and form a four-helix bundle. As indicated above, Rop, which is 63 amino acids in size, forms a two-helix bundle that automatically dimerizes to become a four-helix bundle. Other useful four-helix bundles include the 35 amino acid and 51 amino acid four-helix bundle peptides of Betz et al. (1997) supra, and the 125 amino acid AMD of the α-catenin protein (residues 509-633 of the α-catenin protein).

Where a small stable protein or an α-helical moiety, such as a four-helix bundle protein, is fused to the N-terminus, the randomized peptide can optionally be further stabilized by, for example, covalently linking one or more prolines, with or without a following undefined amino acids (e.g., -Pro, -Pro-Pro, -Pro-Xaa$_n$, -Pro-Pro-Xaa$_n$, etc.) at the C-terminus of the peptide sequence, where n is 1 or 2; likewise, when the α-helical moiety is fused to the C-terminus, the randomized peptide can be further stabilized by, for example, covalently linking one or more prolines, with or without a preceding undefined amino acid (e.g., Pro-, Pro-Pro-, Xaa$_n$-Pro-, Xaa$_n$-Pro-Pro-, etc.) at the N-terminus of the peptide sequence, where n is 1 or 2, as discussed in more detail below.

In another embodiment of the screening method of the invention, the stabilizing group can constitute one or more proline (Pro) residues. Preferably, a proline dipeptide (Pro-Pro) is used as a stabilizing group, although additional prolines may be included. The encoded proline(s) are typically naturally occurring amino acids. However, if and to the extent a proline derivative, for example a hydroxyproline or a methyl- or ethyl-proline derivative, can be encoded or otherwise incorporated into the peptide, those proline derivatives are also useful as stabilizing groups.

At the N-terminus of the peptide, the stabilizing group also can be an oligopeptide having the sequence Xaa$_n$-Pro$_m$-, wherein Xaa is any amino acid (e.g., Ala), m is greater than 0, and n is 1 or 2. For example, m can be about 1 to about 5 (e.g., m can be 2 or 3). An oligopeptide having the sequence Xaa$_n$-Pro$_m$-, wherein m=2, is particularly useful. Likewise, at the C-terminus of the peptide, the stabilizing group can be an oligopeptide having the sequence -Pro$_m$-Xaa$_n$, wherein Xaa is any amino acid (e.g., Ala), m is greater than 0, and n is 1 or 2. For example, m can be about 1 to about 5 (e.g., m can be 2 or 3). An oligopeptide having the sequence Pro$_m$-Xaa$_n$, wherein m=2, is particularly useful.

In one embodiment of the screening method of the invention, the nucleic acid sequence that encodes the randomized peptide in the expression vector is modified to encode both a first stabilizing group linked to the N-terminus of the peptide, the first stabilizing group being selected from the group consisting of small stable protein, Pro-, Pro-Pro-, Xaa$_n$-Pro-, and Xaa$_n$-Pro-Pro-, and a second stabilizing group linked to the C-terminus of the peptide, the second stabilizing group being selected from the group consisting of a small stable protein, -Pro, -Pro-Pro, Pro-Xaa$_n$ and Pro-Pro-Xaa$_n$. The resulting peptide has enhanced stability in the intracellular environment relative to a peptide lacking the terminal stabilizing groups.

In yet another embodiment of the screening method of the invention, the putative bioactive peptide is stabilized by engineering into the peptide a stabilizing motif such as an α-helix motif or an opposite charge ending motif. Chemical synthesis of an oligonucleotide according to the scheme [(CAG)A(T-CAG)] yields an oligonucleotide encoding a peptide consisting of a random mixture of the hydrophilic amino acids H is, Gln, Asn, Lys, Asp, and Glu (see Table 14). Except for aspartate, these amino acids are most often associated with α-helical secondary structural motifs; the resulting oligonucleotides are thus biased in favor of oligonucleotides that encode peptides that are likely to form α-helices in solution.

Alternatively, the putative bioactive peptide is stabilized by flanking a randomized region with a region of uniform charge (e.g., positive charge) on one end and a region of opposite charge (e.g., negative) on the other end, to form an opposite charge-ending motif. To this end, the nucleic acid sequence that encodes the randomized peptide in the expression vector or the expression vector itself is preferably modified to encode a plurality of sequential uniformly charged amino acids at the N-terminus of the peptide, and a plurality of sequential oppositely charged amino acids at the C-terminus of the peptide. The positive charges are supplied by a plurality of positively charged amino acids consisting of lysine, histidine, arginine or a combination thereof; and the negative charges are supplied by a plurality of negatively charged amino acids consisting of aspartate, glutamate or a combination thereof. It is expected that such a peptide will be stabilized by the ionic interaction of the two oppositely charged ends. Preferably, the putative bioactive peptide contains at least three charged amino acids at each end. More preferably, it contains at least four charged amino acids at each end. In a particularly preferred embodiment, the larger acidic amino acid glutamate is paired with the smaller basic amino acid lysine, and the smaller acidic amino acid aspartate is paired with the larger basic amino acid arginine.

The present invention further provides a bioactive peptide containing one or more structural features or motifs selected to enhance the stability of the bioactive peptide in an intracellular environment. For example, a bioactive peptide of the invention can include any stabilizing group as described above in connection with the screening method of the invention. Thus, stabilized bioactive peptides identified using the screening method of the invention are included in the invention. Likewise, both known bioactive peptides and bioactive peptides subsequently discovered, when linked to one or more stabilizing groups as described herein, are also within the scope of the present invention.

Accordingly, the invention provides a bioactive peptide having a stabilizing group at its N-terminus, its C-terminus, or at both termini.

The bioactive peptide of the invention includes a bioactive peptide that has been detectably labeled, derivatized, or modified in any manner desired prior to use, provided it contains one or more terminal stabilizing groups as provided herein. For example, a non-stabilizing moiety (e.g., a label) can be attached to either terminus of the bioactive peptide, which terminus may or may not also include a stabilizing group.

The stabilized bioactive peptide of the invention can be synthesized enzymatically, chemically, or produced by recombinant genetic engineering, without limitation, as described in more detail below. In any synthetic peptide having a stabilizing group that includes one or more prolines according to the present invention, the proline is preferably a naturally occurring amino acid; alternatively, however, it can be a synthetic derivative of proline, for example a hydroxyproline or a methyl- or ethyl-proline derivative. Accordingly, where the abbreviation "Pro" is used herein in connection with a stabilizing group that is part of a synthetic peptide, it is meant to include proline derivatives in addition to a naturally occurring proline.

In a bioactive peptide stabilized at only one terminus (i.e., at either the N- or the C-terminus), the stabilizing group is preferably an α-helical moiety (e.g., four-helix bundle protein such as Rop protein), or one or more proline residues, with or without an undefined amino acid (Xaa). The resulting polypeptide consists essentially of a bioactive peptide and the stabilizing group coupled to one terminus of the bioactive peptide.

A peptide stabilized at both termini can include a first stabilizing group attached to the N-terminus, and a second stabilizing group attached to the C-terminus, where the first and second stabilizing groups are as defined previously in connection with the method for identifying bioactive peptides. The stabilizing group is covalently attached to the peptide (e.g., via a peptide bond).

In one embodiment of the bioactive peptide of the invention, the first stabilizing group is $Xaa_n\text{-}Pro_m\text{-}$, with or without a preceding undefined amino acid (e.g., Pro-, Pro-Pro-, $Xaa_n\text{-}$Pro-, $Xaa_n$-Pro-Pro-, etc.), and the second stabilizing group is $\text{-}Pro_m\text{-}Xaa_n$, with or without a following undefined amino acids (e.g., -Pro, -Pro-Pro, -Pro-$Xaa_n$, -Pro-Pro-$Xaa_n$, etc.). In another embodiment, the first (N-terminal) stabilizing group is a small stable protein or an α-helical moiety (e.g., a four-helix bundle protein such as Rop protein); and the second (C-terminal) stabilizing group is $\text{-}Pro_m\text{-}Xaa_n$ or one or more proline residues (e.g., -Pro-Pro). In yet another embodiment, the second (C-terminal) stabilizing group is a small stable protein or an α-helical moiety (e.g., a four-helix bundle protein such as Rop protein) and the first (N-terminal) stabilizing group is $Xaa_n\text{-}Pro_m\text{-}$ or one or more proline residues.

The invention further provides a peptide stabilized by flanking the amino acid sequence of a bioactive peptide with an opposite charge ending motif, as described herein. Preferably, the resulting stabilized peptide retains at least a portion of the biological activity of the bioactive protein. The stabilized peptide includes a peptide that has been detectably labeled, derivatized, or modified in any manner desired prior to use.

It should be understood that any bioactive peptide, without limitation, can be stabilized according to the invention by attaching a stabilizing group to either or both of the N- and C-termini. Included in the present invention are various antimicrobial peptides, inhibitory peptides, therapeutic peptide drugs, and the like. Non-limiting examples include adrenocorticotropic hormone, bactericidal/permeability-increasing protein (BPI), brain natriuretic peptide, cercropin, endothelin, pentagastrin, scorpion peptides, teriparatide acetate, and all of the peptides listed in Tables 1 and 2, that have been modified at one or both peptide termini to include a stabilizing group as discussed above. Particularly useful bioactive peptides include insulin, glucagon, calcitonin, somatostatin, gonadotrophin, and secretin.

The invention is exemplified by peptides such as Pro-Pro-Asp-Arg-Val-Tyr-Ile-His-Pro-Phe-His-Ile-Pro-Pro (SEQ ID NO:3) and Glu-Asp-Glu-Asp-Asp-Arg-Val-Tyr-Ile-His-Pro-Phe-His-Ile-Arg-Lys-Arg-Lys (SEQ ID NO:4), wherein the middle nine amino acids (Asp-Arg-Val-Tyr-Ile-His-Pro-Phe-His-Ile-; SEQ ID NO: 5) constitute the sequence of angiotensin. In embodiments in which the bioactive peptide is a known peptide (e.g., angiotensin), the stabilizing group or groups that are coupled to one or both of the bioactive peptide's termini are not naturally associated with the peptide. In other words, the stabilizing groups that are coupled to the bioactive peptide are heterologous to the bioactive peptide.

In embodiments in which a first stabilizing group is coupled to the N-terminus of a bioactive peptide and a second stabilizing group is coupled to the C-terminus of the bioactive peptide, the first and second stabilizing groups can be the same or different. In some embodiments where the first and second stabilizing groups are different, they can be said to be "heterologous" to each other, i.e., the stabilizing groups have different amino acid sequences and (1) are from different proteins, or (2) are from the same protein, but the stabilizing groups are not contiguous with each other in a naturally occurring protein, or (3) are produced synthetically and one or both of the stabilizing groups do not correspond to a naturally occurring sequence. For example, a bioactive peptide can be coupled to Rop at the N-terminus and coupled to a two-helix bundle from the α-catenin AMD protein on the C-terminus.

Where the first and second stabilizing groups are from the same protein, it is not necessary that these flanking groups interact with each other so as to confine or constrain the N-terminus and C-terminus of the flanked peptide in close proximity to one another. For example, Lavallie and others (Bio/Technology 11:187-193 (1993); McCoy et al., U.S. Pat. Nos. 5,270,181; 5,292,646; 5,646,016 and 6,143,524) describe internal peptide fusions at the active site loop of thioredoxin, citing the advantages of strong secondary structure in that region, the absence of tertiary structure, and constraint of the peptide at both ends. In the internal thioredoxin fusion, the inserted peptide is bound at each end by cysteine residues, which may form a disulfide linkage and further limit the conformational freedom of the inserted peptide.

However, the present work suggests that neither steric constraint of the peptide ends nor any of the other unique characteristics of thioredoxin polypeptides are necessary. Proteins other than thioredoxin, such as Rop, can be effectively used as first and/or second stabilizing groups for bioactive peptides. Neither the first nor the second stabilizing group needs to possess the capacity to participate in the formation of an intramolecular disulfide bond. That is, the stabilizing group does not need to contain a cysteine or, if it does, the remainder of the polypeptide need not contain a cysteine. The stabilizing groups can be selected such that disulfide formation between the first and second stabilizing groups, if it occurs at all, does not bring the N-terminus and C-terminus of the bioactive peptide into close proximity. For example, flanking stabilizing groups can be selected such that they do not contain, within about three residues of the ends that are connected to the ends of the bioactive peptide, cysteine residues that interact with each other to form an intramolecular disulfide bond.

Moreover, in embodiments in which the first and second stabilizing groups are from the same polypeptide, the stabilizing groups need not, although they may, interact to from a naturally occurring secondary or tertiary structure. Naturally occurring secondary structures include, for example, α-helices, β-sheets, β-turns and the like that are present in, for example, the native solution or crystal structure of the protein as determined by X-ray crystallography or nuclear magnetic resonance spectroscopy. Naturally occurring tertiary structures result from the "folding" of sections the polypeptide that may be distant on the linear chain such that they are close together in space. Tertiary structure includes the three-dimensional relationships between and among the secondary structures and unstructured portions of the molecule.

Modification of a bioactive peptide to yield a stabilized bioactive peptide according to the invention can be achieved by standard techniques well-known in the arts of genetics and peptide synthesis. For example, where the peptide is synthesized de novo, as in solid state peptide synthesis, one or more prolines or other stabilizing groups can be added at the beginning and the end of the peptide chain during the synthetic reaction. In recombinant synthesis, for example as described in Example III herein, one or more codons encoding proline, or codons encoding α-helical moieties, for example, can be inserted into the peptide coding sequence at the beginning and/or the end of the sequence, as desired. Preferably, codons encoding N-terminal prolines are inserted after (i.e., 3' to) the initiation site ATG (which encodes methionine). Analogous techniques are used to synthesize bioactive peptides having an opposite charge ending motif. When a known bioactive peptide is modified to yield a stabilized bioactive peptide according to the invention, the unmodified peptide can conveniently be used as a control in a protease- or peptidase-resistance assay as described hereinabove to confirm, if desired, that the modified peptide exhibits increased stability.

A stabilized bioactive peptide according to the invention can include a peptide whose bioactivity is evident from or identified in a "phage display" experiment. In "phage display" peptides are displayed on the surface of phage and assayed for bioactivity. Displayed peptides are tethered at the one terminus, typically the C-terminus, to the bacteriophage surface. Their other terminus, typically the N-terminus, is free (i.e., non-fused). Structurally, the polypeptide produced in a phage display system is typically a fusion polypeptide that contains a peptide of interest at the N-terminus, followed by a phage protein at the C-terminus. In some phage display polypeptides, however, the order is reversed and the phage protein is at the N-terminus of the polypeptide and the peptide of interest is at the C-terminus. The phage protein is selected such that the polypeptide is displayed on the surface of the bacteriophage. Examples include bacteriophage proteins pIII and pVIII.

Phage display can be used to screen peptide libraries and identify novel bioactive peptides. Bioactive peptides that are active when displayed typically continue to exhibit bioactivity when fabricated synthetically (i.e., without fusion to the phage protein), but they frequently exhibit instability in vivo. This may be due to the fact that the C-terminus is no longer protected or tethered. Hence, the present invention includes a method for stabilizing a bioactive peptide by linking a stabilizing group to the N-terminus or C-terminus of a peptide, when the bioactive peptide has been identified using phage display.

Additionally or alternatively, the genetic constructs used to produce the fusion protein within the bacteriophage can be engineered encode a stabilizing group at the terminus of encoded fusion polypeptide that would otherwise have been free, such that the fusion polypeptide displayed on the surface of the bacteriophage contains a peptide of interest flanked by a stabilizing group at the terminus and a bacteriophage protein at the other terminus.

The invention thus includes methods for phage display of stabilized bioactive proteins, methods for stabilizing bioactive peptides identified using phage display, and bioactive peptides thus identified and/or stabilized.

The present invention also provides a cleavable polypeptide comprising a stabilized, bioactive peptide either immediately preceded by (i.e., adjacent to the N-terminus of the bioactive peptide) a cleavage site, or immediately followed by (i.e., adjacent to the C-terminus of the bioactive peptide) a cleavage site. Thus, a bioactive peptide as contemplated by the invention can be part of a cleavable polypeptide. The cleavable polypeptide is cleavable, either chemically, as with cyanogen bromide, or enzymatically, to yield the bioactive peptide. The resulting bioactive peptide either includes a first stabilizing group positioned at its N-terminus and/or a second stabilizing group positioned at its C-terminus, both as described hereinabove. The cleavage site immediately precedes the N-terminal stabilizing group or immediately follows the C-terminal stabilizing group. In the case of a bioactive peptide stabilized with an opposite charge ending motif, the cleavage site immediately precedes the first charged region or immediately follows the second charged region. The cleavage site makes it possible to administer a bioactive peptide in a form that could allow intracellular targeting and/or activation.

Alternatively, a bioactive peptide of the invention can be fused to a noncleavable N-terminal or C-terminal targeting sequence wherein the targeting sequence allows targeted delivery of the bioactive peptide, e.g., intracellular targeting or tissue-specific targeting of the bioactive peptide. In one embodiment of this aspect of the invention, a stabilizing group (e.g., one or more proline residues) is positioned at the free (i.e., non-fused) terminus of the bioactive peptide as described hereinabove in connection with the screening method for identifying bioactive peptides. The targeting sequence attached to the other peptide terminus can, but need not, contain a small stable protein such as Rop or one or more proline residues, as long as the targeting function of the targeting sequence is preserved. In another embodiment of this aspect of the invention, the bioactive peptide is stabilized with a charge ending motif as described hereinabove, wherein one charged region is coupled to the free terminus of the bioactive peptide, and the other charged region is disposed between the targeting sequence and the active sequence of the bioactive peptide.

The invention further includes a method for using an antimicrobial peptide that includes covalently linking a stabilizing group, as described above, to the N-terminus, the C-terminus, or to both termini, to yield a stabilized antimicrobial peptide, then contacting a microbe with the stabilized antimicrobial peptide. Alternatively, the stabilized antimicrobial peptide used in this aspect of the invention is made by covalently linking oppositely charged regions, as described above, to each end of the antimicrobial peptide to form an opposite charge ending motif. An antimicrobial peptide is to be broadly understood as including any bioactive peptide that adversely affects a microbe such as a bacterium, virus, protozoan, or the like, as described in more detail above. An example of an antimicrobial peptide is an inhibitory peptide that inhibits the growth of a microbe. When the antimicrobial peptide is covalently linked to a stabilizing group at only one peptide terminus, any of the stabilizing groups described hereinabove can be utilized. When the antimicrobial peptide is covalently linked to a stabilizing group at both peptide termini, the method includes covalently linking a first stabilizing group to the N terminus of the antimicrobial peptide and a second stabilizing group to the C terminus of the antimicrobial peptide, where the first and second stabilizing groups are as defined previously in connection with the method for identifying bioactive peptides. In a preferred embodiment of the method for using an antimicrobial peptide, one or more prolines, more preferably a Pro-Pro dipeptide, is attached to at least one, preferably both, termini of the antimicrobial peptide. Alternatively, or in addition, an $Xaa_n$-$Pro_m$-sequence, as described above, can be attached to the N-terminus of a microbial peptide, and/or a -$Pro_m$-$Xaa_n$ sequence can be attached to the C-terminus, to yield a stabilized antimicrobial peptide.

The antimicrobial peptide thus modified in accordance with the invention has enhanced stability in the intracellular environment relative to an unmodified antimicrobial peptide. As noted earlier, the unmodified peptide can conveniently be used as a control in a protease- or peptidase-resistance assay as described hereinabove to confirm, if desired, that the modified peptide exhibits increased stability. Further, the antimicrobial activity of the antimicrobial peptide is preferably preserved or enhanced in the modified antimicrobial peptide;

modifications that reduce or eliminate the antimicrobial activity of the antimicrobial peptide are easily detected and are to be avoided.

The invention further provides a method for inhibiting the growth of a microbe comprising contacting the microbe with a stabilized inhibitory peptide. As described above, the stabilized inhibitory peptide can have a stabilizing group attached at its N-terminus, C-terminus, or both termini.

Also included in the present invention is a method for treating a patient having a condition treatable with a peptide drug, comprising administering to the patient a peptide drug that has been stabilized as described herein. Peptide drugs for use in therapeutic treatments are well known (see, e.g., Table 1). However, they are often easily degraded in biological systems, which affects their efficacy. In one embodiment of the present method, the patient is treated with a stabilized drug comprising the peptide drug of choice and a stabilizing group linked to either the N-terminus, the C-terminus of, or to both termini of the peptide drug. In another embodiment of the present method, the patient is treated with a stabilized drug comprising the peptide drug of choice that has been stabilized by attachment of oppositely charged regions to both termini of the peptide drug. Because the peptide drug is thereby stabilized against proteolytic degradation, greater amounts of the drug should reach the intended target in the patient.

In embodiments of the method involving administration of a peptide drug that is covalently linked to a stabilizing group at only one peptide terminus, the stabilizing group is preferably an α-helical moiety, such as a four-helix bundle protein (e.g., Rop), provided that attachment of the α-helical moiety to the peptide terminus preserves a sufficient amount of efficacy for the drug. It is to be nonetheless understood that the group or groups used to stabilize the peptide drug are as defined hereinabove, without limitation. In embodiments involving administration of a peptide drug covalently linked to a stabilizing group at both peptide termini, the peptide drug includes a first stabilizing group linked to the N-terminus of the peptide drug and a second stabilizing group linked to the C-terminus of the peptide drug. Thus, in another preferred embodiment of the treatment method of the invention, the stabilized peptide drug includes one or more prolines, more preferably a proline-proline dipeptide, attached to one or both termini of the peptide drug. For example, the peptide drug can be stabilized by covalent attachment of a Rop protein at one terminus, and by covalent attachment of a proline or proline dipeptide at the other terminus; in another preferred embodiment, the peptide drug can be stabilized by proline dipeptides at each of the N-terminus and C terminus. Alternatively, or in addition, the stabilized peptide drug used in the treatment method can include an $Xaa_n$-$Pro_m$-sequence at the N-terminus of the peptide drug, and/or a -$Pro_m$-$Xaa_n$ sequence at the C-terminus. Optionally, prior to administering the stabilized peptide drug, the treatment method can include covalently linking a stabilizing group to one or both termini of the peptide drug to yield the stabilized peptide drug.

If desired, the unmodified peptide drug can conveniently be used as a control in a protease- or peptidase-resistance assay as described hereinabove to confirm that the stabilized peptide drug exhibits increased stability. Further, the therapeutic efficacy of the peptide drug is preferably preserved or enhanced in the stabilized peptide drug; modifications that reduce or eliminate the therapeutic efficacy of the peptide drug are easily detected and are to be avoided.

The present invention further includes a fusion protein comprising a four-helix bundle protein, preferably Rop protein, and a polypeptide. Preferably the polypeptide is bioactive; more preferably it is a bioactive peptide. The fusion protein of the invention can be used in any convenient expression vector known in the art for expression or overexpression of a peptide or protein of interest. Optionally, a cleavage site is present between the four-helix bundle protein and the polypeptide to allow cleavage, isolation and purification of the polypeptide. In one embodiment of the fusion protein, the four-helix bundle protein is covalently linked at its C-terminus to the N-terminus of the polypeptide; in an alternative embodiment, the four-helix bundle protein is covalently linked at its N-terminus to the C-terminus of the polypeptide. Fusion proteins of the invention, and expression vectors comprising nucleic acid sequences encoding fusion proteins wherein the nucleic acid sequences are operably linked to a regulatory control element such as a promoter, are useful for producing or overproducing any peptide or protein of interest.

EXAMPLES

The present invention is illustrated by the following examples. It is to be understood that the particular examples, materials, amounts, and procedures are to be interpreted broadly in accordance with the scope and spirit of the invention as set forth herein.

Example I

Construction and Characterization of a Highly Regulable Expression Vector, pLAC11, and its Multipurpose Derivatives, pLAC22 and pLAC33

A number of different expression vectors have been developed over the years to facilitate the production of proteins in *E. coli* and related bacteria. Most of the routinely employed expression vectors rely on lac control in order to overproduce a gene of choice. While these vectors allow for overexpression of the gene product of interest, they are leaky due to changes that have been introduced into the lac control region and gene expression can never be shut off under repressed conditions, as described in more detail below. Numerous researchers have noticed this problem with the more popular expression vectors pKK223-3 (G. Posfai et al. Gene. 50: 63-67 (1986); N. Scrutton et al., Biochem J. 245: 875-880 (1987)), pKK233-2 (P. Beremand et al., Arch Biochem Biophys. 256: 90-100 (1987); K. Ooki et al., Biochemie. 76: 398-403 (1994)), pTrc99A (S. Ghosh, Protein Expr. Purif. 10: 100-106 (1997); J. Ranie et al., Mol. Biochem. Parasitol. 61: 159-169 (1993)), as well as the pET series (M. Eren et al., J. Biol. Chem. 264: 14874-14879 (1989); G. Godson, Gene 100: 59-64 (1991)).

The expression vector described in this example, pLAC11, was designed to be more regulable and thus more tightly repressible when grown under repressed conditions. This allows better regulation of cloned genes in order to conduct physiological experiments. pLAC11 can be used to conduct physiologically relevant studies in which the cloned gene is expressed at levels equal to that obtainable from the chromosomal copy of the gene in question. The expression vectors described here were designed utilizing the wild-type lac promoter/operator in order to accomplish this purpose and include all of the lac control region, without modification, that is contained between the start of the O3 auxiliary operator through the end of the O1 operator. As with all lac based vectors, the pLAC11 expression vector described herein can be turned on or off by the presence or absence of the gratuitous inducer IPTG. In experiments in which a bacterial cell contained both a null allele in the chromosome and a second copy of the wild-type allele on pLAC11 cells grown under repressed conditions exhibited the null phenotype while cells grown under induced conditions exhibited the wild-type phenotype. Thus the pLAC11 vector truly allows for the gene of interest to be grown under either completely repressed or fully induced conditions. Two multipurpose derivatives of pLAC11, pLAC22 and pLAC33 were also constructed to fulfill different experimental needs.

The vectors pLAC11, pLAC22 and pLAC33 were deposited with the American Type Culture Collection (ATCC), 10801 University Blvd., Manassas, Va., 20110-2209, USA, on Feb. 16, 1999, and assigned ATCC deposit numbers ATCC 207108, ATCC 207110 and ATCC 207109, respectively. It is nonetheless to be understood that the written description herein is considered sufficient to enable one skilled in the art to fully practice the present invention. Moreover, the deposited embodiment is intended as a single illustration of one aspect of the invention and is not to be construed as limiting the scope of the claims in any way.

Materials and Methods

Media. Minimal M9 media (6 g disodium phosphate, 3 g potassium phosphate, 1 g ammonium chloride, 0.5 g sodium chloride, distilled water to 1 L; autoclave; add 1 mL m magnesium sulfate (1M) and 0.1 mL calcium chloride (1M); a sugar added to a final concentration of 0.2%; vitamins and amino acids as required for non-prototrophic strains) and rich LB media (10 g tryptone, 5 g yeast extract, 10 g sodium chloride, distilled water to 1 L; autoclave) were prepared as described by Miller (J. Miller, "Experiments in molecular genetics" Cold Spring Harbor Laboratory, Cold Spring Harbor, N.Y. (1972). The antibiotics ampicillin, kanamycin, streptomycin, and tetracycline (Sigma Chemical Company, St. Louis, Mo.) were used in rich media at a final concentration of 100, 40, 200, and 20 ug/ml, respectively. When used in minimal media, tetracycline was added at a final concentration of 10 îg/ml. 5-bromo-4-chloro-3-indoyl β-D-galactopyranoside (Xgal) was added to media at a final concentration of 40 îg/ml unless otherwise noted. IPTG was added to media at a final concentration of 1 mM.

Chemicals and Reagents. When amplified DNA was used to construct the plasmids that were generated in this study, the PCR reaction was carried out using native Pfu polymerase from Stratagene (Cat. No. 600135). Xgal and IPTG were purchased from Diagnostic Chemicals Limited.

Bacterial Strains and Plasmids. Bacterial strains and plasmids are listed in Table 4. To construct ALS225, ALS224 was mated with ALS216 and streptomycin resistant, blue recombinants were selected on a Rich LB plat that contained streptomycin, Xgal, and IPTG. To construct ALS226, ALS224 was mated with ALS217 and streptomycin resistant, kanomycin resistant recombinants were selected on a Rich LB plate that contained streptomycin and kanamycin. To construct ALSS15, ALSS14 was mated with ALS216 and streptomycin resistant, blue recombinants were selected on a Rich LB plate that contained streptomycin, Xgal, and IPTG. To construct ALS527, ALS524 was mated with ALS224 and streptomycin resistant, tetracycline resistant recombinants were selected on a Rich LB plate that contained streptomycin and tetracycline. To construct ALS535, ALS533 was mated with ALS498 and tetracycline resistant recombinants were selected on a Minimal M9 Glucose plate that contained tetracycline, leucine and thiamine ($B_1$) (Sigma Chemical Company). To construct ALS533, a P1 lysate prepared from *E. coli* strain K5076 (H. Miller et al., Cell 20: 711-719 (1980)) was used to transduce ALS224 and tetracycline resistant transductants were selected.

TABLE 4

Bacterial strains and plasmids used in Example I

*E. coli* Strains

| Laboratory Name | Original Name | Genotype | Source |
|---|---|---|---|
| ALS216 | SE9100 | araD139 Δ(lac)U169 thi flbB5301 deoC7 ptsF25 rpsE/F' lacl$^q$ Z$^+$ Y$^+$ A$^+$ | E. Altman et al., J. Biol. Chem. 265: 18148-18153 (1990) |
| ALS217 | SE9100.1 | araD139 Δ(lac)U169 thi flbB5301 deoC7 ptsF25 rpsE/F' lacl$^q$ Z::Tn5 Y+ A+ | S. Emr (Univ. of California, San Diego) |
| ALS221 | BL21(DE3) | ompT hsdS(b) (R-M-) gal dcm | F. Studier et al., J. Mol. Biol. 189: 113-130 (1986) |
| ALS224 | MC1061 | araD139 Δ(araABOIC-leu) 7679 Δ(lac)X74 galU galK rpsL hsr– hsm+ | M. Casadaban et al., J. Mol. Biol. 138: 179-207 (1980) |
| ALS225 | | MC1061/F' lacl$^q$ Z$^+$ Y$^+$ A$^+$ | This example |
| ALS226 | | MC1061/F' lacl$^q$ Z::Tn5 Y$^+$ A$^+$ | This example |
| ALS269 | CSH27 | F-trpA33 thi | J. Miller, "Experiments in molecular genetics" Cold Spring Laboratory, Cold Spring Harbor, NY (1972) |
| ALS413 | MG1655 | *E. coli* wild-type F-λ- | M. Guyer et al., Cold Spring Harbor Symp. Quant. Biol. 45: 135-140 (1980) |
| ALS498 | JM101 | supE thi Δ(lac-proAB)/ F' traD36proA$^+$B$^+$ lacl$^q$ Δ(lacZ) M15 | C. Yanisch-Perron et al., Gene. 33: 103-119 (1985) |
| ALS514 | NM554 | MC1061 recA13 | E. Raleigh et al., Nucl. Acids Res. 16: 1563-1575 (1988) |
| ALS515 | | MC1061 recA13/F' lacl$^q$ Z$^+$ Y$^+$ A$^+$ | This example |

TABLE 4-continued

Bacterial strains and plasmids used in Example I

| | | | |
|---|---|---|---|
| ALS524 | XL1-Blue | recAI endAI gyrA96 thi-I hsdRI7 supE44 relAI lac/F' proAB lacI$^q$ Δ(lacZ) M15 Tn10 | Stratagene (Cat. No. 200268) |
| ALS527 | | MC1061/F' proAB lacI$^q$ Δ(lacZ) M15 Tn10 | This example |
| ALS533 | | MC1061 proAB::Tn10 | This example |
| ALS535 | | MC1061 proAB::Tn10/ F' lacI$^q$ Δ(lacZ) M15 proA+B+ | This example |
| ALS598 | CAG18615 | zjb-3179::Tn10dKan lambda-rph-1 | M. Singer et al., Microbiol. Rev. 53: 1-24 (1989) |

Plasmids

| Plasmid Name | Relevant Characteristics | Source |
|---|---|---|
| pBH20 | wild-type lac promoter/operator, Amp$^R$, Tet$^R$, colE1 replicon | K. Itakura et al., Science. 198: 1056-1063 (1977) |
| pBR322 | Amp$^R$, Tet$^R$, colE1 replicon | F. Bolivar et al., Gene. 2: 95-113 (1977) |
| pET-21(+) | T7 promoter/lac operator, lacIq, Amp$^R$, colE1 replicon | Novagen (Cat. No. 69770-1) |
| pGE226 | wild-type recA gene, Amp$^R$ | J. Weisemann, et al., J. Bacteriol. 163: 748-755 (1985) |
| pKK223-3 | tac promoter/operator, Amp$^R$, colE1 replicon | J. Brosius et al., Proc. Natl. Acad. Sci. USA 81: 6929-6933 (1984) |
| pKK223-2 | trc promoter/operator, Amp$^R$, colE1 replicon | E. Amann et al., Gene. 40: 183-190 (1985) |
| pLysE | T7 lysozyme, Cam$^R$, P15A replicon | F. Studier, J. Mol. Biol. 219: 37-44 (1991) |
| pLysS | T7 lysozyme, Cam$^R$, P15A replicon | F. Studier, J. Mol. Biol. 219: 37-44 (1991) |
| pMS421 | wild-type lac promoter/operator, lacIq, Strep$^R$, Spec$^R$, SC101 replicon | D. Graña et al., Genetics. 120: 319-327 (1988) |
| pTer7 | wild-type lacZ coding region, Amp$^R$ | R. Young (Texas A&M University) |
| pTrc99A | trc promoter/operator, lacIq, Amp$^R$, colE1 replicon | E. Amann et al., Gene. 69: 301-315 (1988) |
| pUC8 | lac promoter/operator, Amp$^R$, colE1 replicon | J. Vieira et al., Gene. 19: 259-268 (1982) |
| pXE60 | wild-type TOL pWWO xylE gene, Amp$^R$ | J. Westpheling (Univ. of Georgia) |

Construction of the pLAC11, pLAC22, and pLAC33 expression vectors. To construct pLAC11, primers #1 and #2 (see Table 5) were used to polymerase chain reaction (PCR) amplify a 952 base pair (bp fragment from the plasmid pBH20 which contains the wild-type lac operon. Primer #2 introduced two different base pair mutations into the seven base spacer region between the Shine Dalgarno site and the ATG start site of the lacZ which converted it from AACAGCT to AAGATCT thus placing a Bgl II site in between the Shine Dalgarno and the start codon of the lacZ gene. The resulting fragment was gel isolated, digested with Pst I and EcoR I, and then ligated into the 3614 bp fragment from the plasmid pBR322ΔAvaI which had been digested with the same two restriction enzymes. To construct pBR322ΔAva1, pBr$_{322}$ was digested with Ava1, filled in using Klenow, and then religated. To construct pLAC22, a 1291 bp Nco I. EcoR I fragment was gel isolated from pLAC21 and ligated to a 4361 bp Nco I. EcoR I fragment which was gel isolated from pBR322/NcoI. To construct pLAC21, primers #2 and #3 (see Table 5) were used to PCR amplify a 1310 bp fragment from the plasmid pMS421 which contains the wild-type lac operon as well as the lacI$^q$ repressor. The resulting fragment was gel isolated, digested with EcoR I, and then ligated into pBR322 which had also been digested with EcoR I. To construct pBR322/Nco I, primers #4 and #5 (see Table 5) were used to PCR amplify a 788 bp fragment from the plasmid pBR322. The resulting fragment was gel isolated, digested with Pst I and EcoR I, and then ligated into the 3606 bp fragment from the plasmid pBR322 which had been digested with the same two restriction enzymes. The pBR322Mco I vector also contains added Kpn 1 and Sma I sites in addition to the new Nco I site. To construct pLAC33, a 2778 bp fragment was gel isolated from pLAC12 which had been digested with BsaB I and Bsa I and ligated to a 960 bp fragment from pUC8 which had been digested with Afl III, filled in with Klenow, and then digested with Bsa I. To construct pLAC12, a 1310 bp Pst I, BamH I fragment was gel isolated from pLAC11 and ligated to a 3232 bp Pst I, BamH I fragment which was gel isolated from pBR322.

TABLE 5

Primers employed to PCT amplify DNA fragments that were used in the construction of the various plasmids described in Example I

```
pLAC11 and pLAC22
 1 (for)   GTT GCC ATT GCT GCA GGC AT                                  (SEQ ID NO:  6)
 2 (rev)   ATT GAA TTC ATA AGA TCT TTC CTG TGT GAA ATT GTT ATC CGC    (SEQ ID NO:  7)
 3 (for)   ATT GAA TTC ACC ATG GAC ACC ATC GAA TGG TGC AAA A          (SEQ ID NO:  8)

pBr322/Nco I
 4 (for)   GTT GTT GCC ATT GCT GCA G                                   (SEQ ID NO:  9)
 5 (rev)   TGT ATG AAT TCC CGG GTA CCA TGG TTG AAG ACG AAA GGG CCT C  (SEQ ID NO: 10)

Bgl II-lacZ-Hind III
 6 (for)   TAC TAT AGA TCT ATG ACC ATG ATT ACG GAT TCA CTG            (SEQ ID NO: 11)
 7 (rev)   TAC ATA AAG CTT GGC CTG CCC GGT TAT TAT TAT TTT            (SEQ ID NO: 12)

Pst I-lacZ-Hind III
 8 (for)   TAT CAT CTG CAG AGG AAA CAG CTA TGA CCA TGA TTA CGG ATT CAC TG  (SEQ ID NO: 13)
 9 (rev)   TAC ATA CTC GAG CAG GAA AGC TTG GCC TGC CCG GTT ATT ATT ATT TT  (SEQ ID NO: 14)

BamH 1-lacZ-Hind III (also uses primer #9)
10 (for)   TAT CAT GGA TCC AGG AAA CAG CTA TGA CCA TGA TTA CGG ATT CAC TG  (SEQ ID NO: 15)

Bgl II-recA-Hind III
11 (for)   TAC TAT AGA TCT ATG GCT ATC GAC GAA AAC AAA CAG            (SEQ ID NO: 16)
12 (rev)   ATA TAT AAG CTT TTA AAA ATC TTC GTT AGT TTC TGC TAC G      (SEQ ID NO: 17)

BamH 1-xylE-EcoR I
13 (for)   TAC TAT AGA TCT ATG AAC AAA GGT GTA ATG CGA CC             (SEQ ID NO: 18)
14 (rev)   ATT AGT GAA TTC GCA CAA TCT CTG CAA TAA GTC GT             (SEQ ID NO: 19)
```

In Table 5 the regions of the primers that are homologous to the DNA target template are indicated with a dotted underline, while the relevant restriction sites are indicated with a solid underline. All primers are listed in the 5'→3' orientation.

Compilation of the DNA sequences for the pLAC11, pLAC22, and pLAC33 expression vectors. All of the DNA that is contained in the pLAC11, pLAC22, and, pLAC33 vectors has been sequenced.

The sequence for the pLAC11 vector, which is 4547 bp, can be compiled as follows: bp 1-15 are AGATCTTATGAATTC (SEQ ID NO: 20) from primer #2 (Table 5); bp 16-1434 are bp 4-1422 from pBR322 (GenBank Accession #JO1 749); bp 1435-1442 are TCGGTCGG, caused by filling in the Ava I site in pBR322ΔAvaI; bp 1443-4375 is bp 1427-4359 from pBR322 (GenBank Accession #JO1749); and bp 4376-4547 are bp 1106-1277 from the wild-type E. coli lac operon (GenBank Accession #J01636).

The sequence for the pLAC22 vector which is 5652 bp can be compiled as follows: bp 1-15 are AGATCTTATGAATTC (SEQ ID NO: 21) from primer #2 (Table 5); bp 16-4370 are bp 4-4358 from pBR322 (GenBank Accession# J01749); bp 4371-4376 is CCATGG which is the Nco I site from pBR322/Nco I; and bp 4377-5652 are bp 2-1277 from the wild-type E. coli lac operon (GenBank Accession #J01636), except that bp #4391 of the pLAC22 sequence or bp#16 from the wild-type E. coli lac operon sequence has been changed from a "C" to a "T" to reflect the presence of the lacI$^q$ mutation (J. Brosius et al., Proc. Natl. Acad. Sci. USA. 81: 6929-6933 (1984)).

The sequence for the pLAC33 vector which is 3742 bp can be compiled as follows: bp 1-15 is AGATCTTATGAATTC (SEQ. ID NO: 22) from primer #2 (Table 5); bp 16-1684 are bp 4-1672 from pEk322 (GenBank Accession # 501749); bp 1685-2638 are bp 786-1739 from pUC8 (GenBank Accession #L09132); bp 2639-3570 are bp 3428-4359 from pBR322 (GenBank Accession #30 J01749); and bp 3571-3742 are bp 1106-1277 from the wild-type E. coli lac operon (GenBank Accession #J01636). In the maps for these vectors, the ori is identified as per Balbás (P. Balbás et al., Gene. 50: 3-40 (1986)), while the lacPO is indicated starting with the O3 auxiliary operatic and ending with the O1 operator as per Müller-Hill (B. Müller-Hill, *The lac Operon: A Short History of a Genetic Paradigm*. Walter de Gruyter, Berlin, Germany (1996)).

Construction of the pLAC11-, pLAC22-, pLAC33-, pKK223-3-, pKK233-2-, pTrc99A-, and pET-21(+)-lacZ constructs. To construct pLAC11-lacZ, pLAC22-lacZ, and pLAC33-lacZ, primers #6 and #7 (see Table 5) were used to PCR amplify a 3115 bp fragment from the plasmid pTer7 which contains the wild-type lacZ gene. The resulting fragment was gel isolated, digested with Bgl II and Hind III, and then ligated into the pLAC11, pLAC22 or pLAC33 vectors that had been digested with the same two restriction enzymes. To construct pKK223-3-lacZ and pKK233-2-lacZ, primers #8 and #9 (see Table 5) were used to PCR amplify a 3137 bp fragment from the plasmid pTer7. The resulting fragment was gel isolated, digested with Pst I and Hind III, and then ligated into the pKK223-3 or pKK233-2 vectors which had been digested with the same two restriction enzymes. To construct pTrc99A-lacZ and pET-21 (+)-lacZ, primers #9 and #10 (see Table 5) were used to PCR amplify a 3137 bp fragment from the plasmid pTer7. The resulting fragment was gel isolated, digested with BamH I and Hind III, and then ligated into the pTrc99A or pET-21 (+) vectors which had been digested with the same two restriction enzymes.

Construction of the pLAC11-recA and xylE constructs. To construct pLAC11-recA, primers #11 and #12 (see Table 5)

were used to PCR amplify a 1085 bp fragment from the plasmid pGE226 which contains the wild-type recA gene. The resulting fragment was gel isolated, digested with Bgl II and Hind III, and then ligated into the pLAC11 vector which had been digested with the same two restriction enzymes. To construct pLAC11-xylE, primers #13 and #14 (see Table 5) were used to PCR amplify a 979 bp fragment from the plasmid pXE60 which contains the wild-type *Pseudomonas putida* xylE gene isolated from the TOL pWW0 plasmid. The resulting fragment was gel isolated, digested with Bgl II and EcoR I, and then ligated into the pLAC11 vector which had been digested with the same two restriction enzymes.

Assays. β-galactosidase assays were performed as described by Miller (J. Miller. "Experiments in molecular genetics," Cold Spring Harbor Laboratory, Cold Spring Harbor, N.Y. (1972)), while catechol 2,3-dioxygenase (catO$_2$ase) assays were performed as described by Zukowski, et. al. (M. Zukowski et al., Proc. Natl. Acad. Sci. U.S.A. 80: 1101-1105 (1983)).

Results

Figure 3:
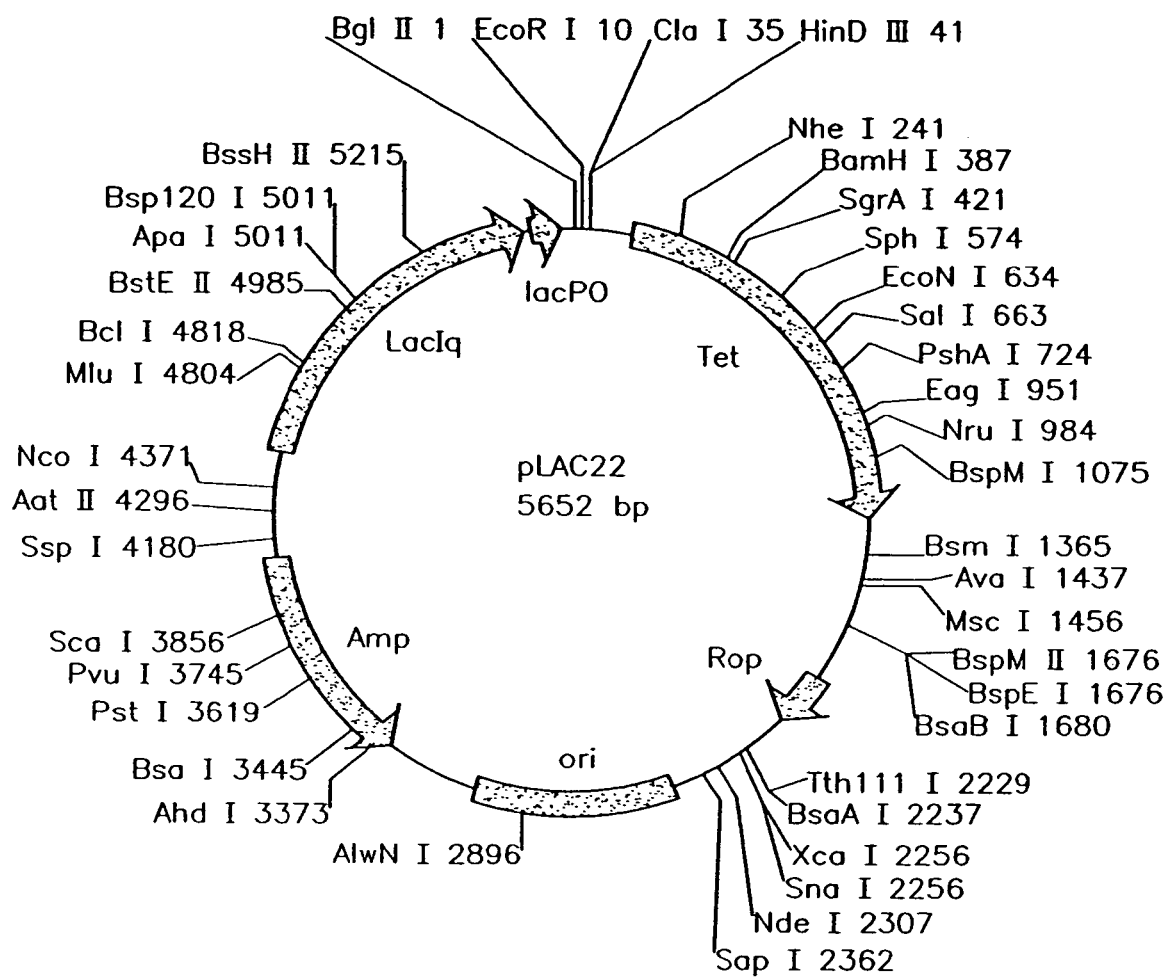
FIG. 3 is a map of plasmid pLAC22. The unique restriction sites and the base pair at which they cut are indicated. Other sites of interest are also shown, including Tet (98-1288), Rop (1927-2118), ori (2547-3134), Amp (3305-4165), lacI$^q$ (4452-5536), and lacPO (5529-5641).
Figure 4:
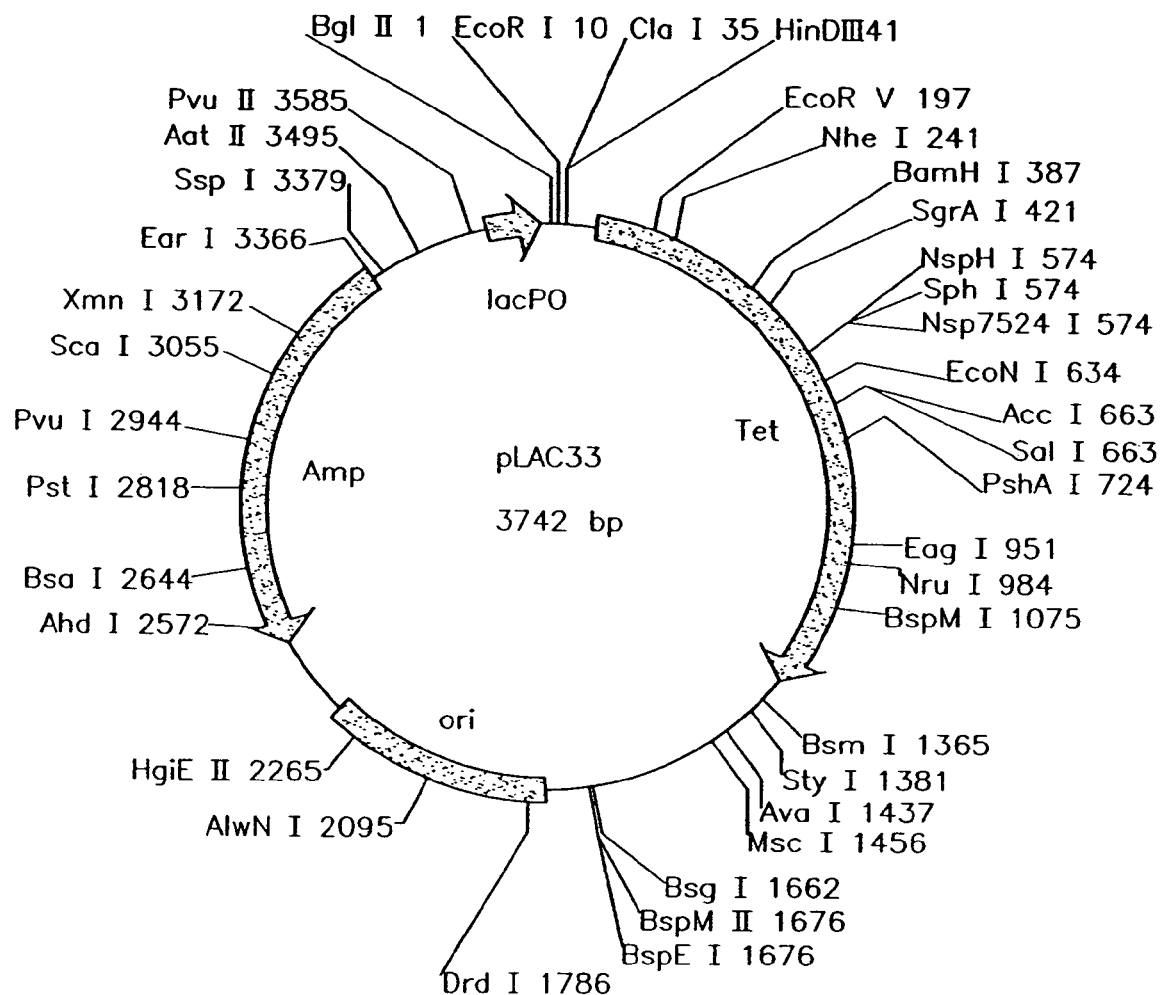
FIG. 4 is a map of plasmid pLAC33. The unique restriction sites and the base pair at which they cut are indicated. Other sites of interest are also shown, including Tet (98-1288), ori (1746-2333), Amp (2504-3364), and lacPO (3619-3731).

Construction and features of pLAC11, pLAC22, and pLAC33. Plasmid maps that indicate the unique restriction sites, drug resistances, origin of replication, and other relevant regions that are contained in pLAC11, pLAC22, and pLAC33 are shown in FIGS. 2, 3 and 4, respectively. pLAC11 was designed to be the most tightly regulable of these vectors. It utilizes the ColE1 origin of replication from pBR322 and LacI repressor is provided in trans from either an episome or another compatible plasmid. pLAC22 is very similar to pLAC11, however, it also contains lacI$^q$, thus a source of LacI does not have to be provided in trans. pLAC33 is a derivative of pLAC11 which utilizes the mutated ColE1 origin of replication from pUC8 (S. Lin-Chao et al., Mol. Micro. 6: 3385-3393 (1992)) and thus pLAC33's copy number is significantly higher than pLAC11 and is comparable to that of other pUC vectors. Because the cloning regions of these three vectors are identical, cloned genes can be trivially shuffled between and among them depending on the expression demands of the experiment in question.

To clone into pLAC 11, pLAC22, or pLAC33, PCR amplification is performed with primers that are designed to introduce unique restriction sites just upstream and downstream of the gene of interest. Usually a Bgl II site is introduced immediately in front of the ATG start codon and an EcoR I site is introduced immediately following the stop codon. An additional 6 bases is added to both ends of the oligonucleotide in order to ensure that complete digestion of the amplified PCR product will occur. After amplification the double-stranded (ds) DNA is restricted with Bgl II and EcoR I, and cloned into the vector which has also been restricted with the same two enzymes. If the gene of interest contains a BlgII site, then BamH I or Bcl I can be used instead since they generate overhangs which are compatible with Bgl II. If the gene of interest contains an EcoR I site, then a site downstream of EcoR I in the vector (such as Hind III) can be substituted.

Comparison of pLAC11, pLAC22, and pLAC33, to other expression vectors. In order to demonstrate how regulable the pLAC11, pLAC22, and pLAC33 expression vectors were, the wild-type lacZ gene was cloned into pLAC11, pLAC22, pLAC33, pKK223-3, pKK233-2, pTrc99A, and pET-21(+). Constructs which required an extraneous source of LacI for their repression were transformed into ALS225, while constructs which contained a source of LacI on the vector were transformed into ALS224. pET-21 (+) constructs were transformed into BL21 because they require T7 RNA polymerase for their expression. Four clones were chosen for each of these seven constructs and β-galactosidase assays were performed under repressed and induced conditions. Rich Amp overnights were diluted 1 to 200 in either Rich Amp Glucose or Rich Amp IPTG media and grown until they reached mid-log(OD$_{550}$=0.5). In the case of PET-21(+) the pLysE and pLysS plasmids, which make T7 lysozyme and thus lower the amount of available T7 polymerase, were also transformed into each of the constructs. Table 6 shows the results of these studies and also lists the induction ratio that was determined for each of the expression vectors. As the data clearly indicate, pLAC 11 is the most regulable of these expression vectors and its induction ratio is close to that which can be achieved with the wild-type lac operon. The vector which yielded the lowest level of expression under repressed conditions was pLAC 11, while the vector which yielded the highest level of expression under induced conditions was pLAC33.

TABLE 6

β-galactosidase levels obtained in different expression vectors grown under either repressed or induced conditions

| | | # of Miller Units Observed | | |
| --- | --- | --- | --- | --- |
| Vector | Source | Repressed Conditions | Induced Conditions | Fold Induction |
| pLAC11 | F' | 19 | 11209 | 590X |
| pLAC22 | Plasmid | 152 | 13315 | 88X |
| pLAC33 | F' | 322 | 23443 | 73X |
| pKK223-3 | F' | 92 | 11037 | 120X |
| pKK233-2 | F' | 85 | 10371 | 122X |
| pTrc99A | Plasmid | 261 | 21381 | 82X |
| pET-21(+) | Plasmid | 2929 | 16803 | 6X |
| pET-21(+)/pLysE | Plasmid | 4085 | 19558 | 5X |
| pET-21(+)/pLysS | Plasmid | 1598 | 20268 | 13X |

The average values obtained for the four clones that were tested from each vector are listed in the table. Standard deviation is not shown but was less than 5% in each case. Induction ratios are expressed as the ratio of enzymatic activity observed at fully induced conditions versus fully repressed conditions. The plasmid pLysE yielded unexpected results; it was expected to cause lower amounts of lacZ to be expressed from pET-21(+) under repressed conditions and, instead, higher amounts were observed. As a result, both pLysE and pLysS were restriction mapped to make sure that they were correct.

Figure 5:
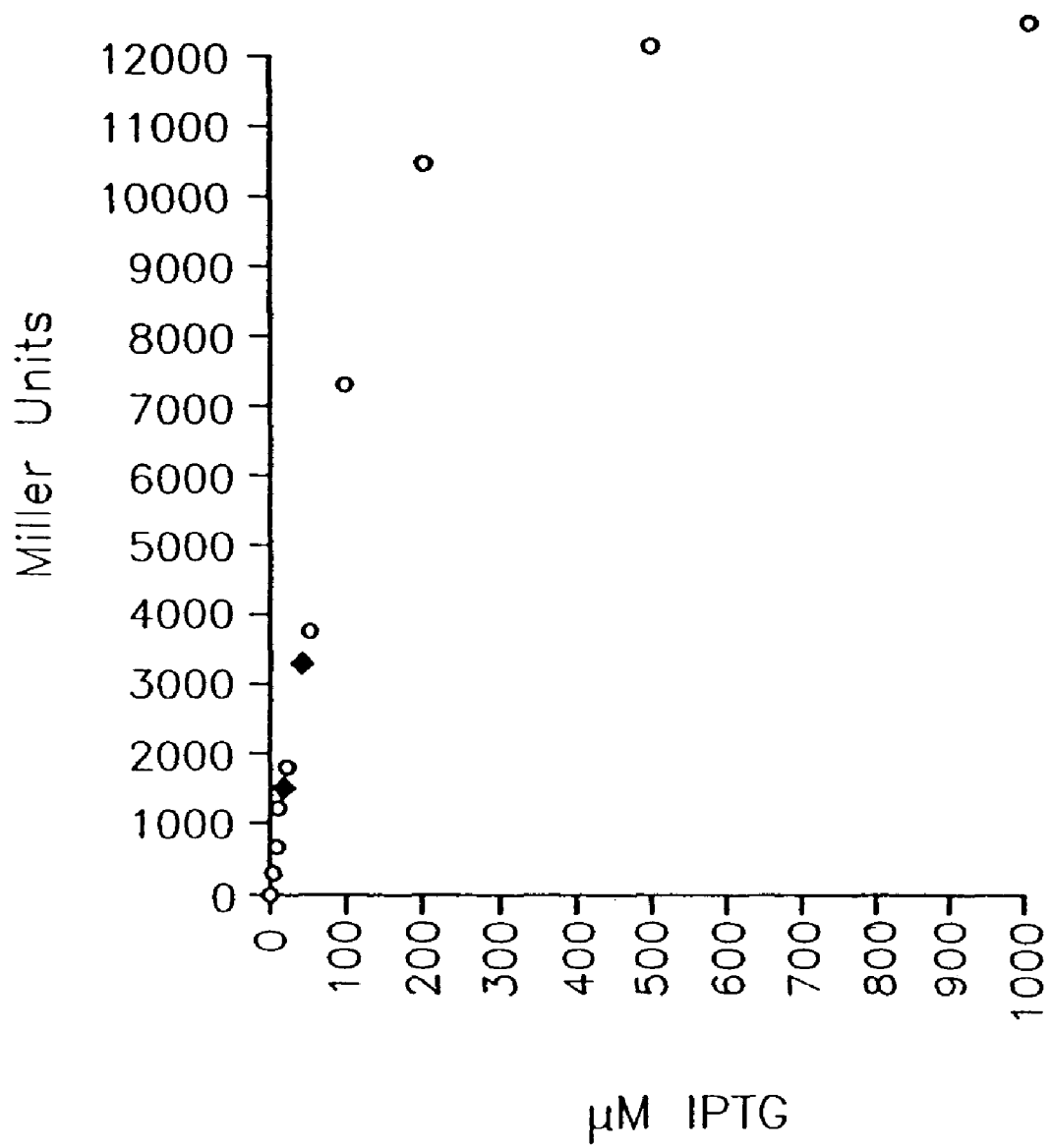
FIG. 5 shows the response of the pLAC11-lacZ construct (open circles) to varying amounts of isopropyl β-D-thiogalactoside (IPTG). A filled square indicates the β-galactosidase activity that was obtained when MG1655 or CSH27 cells were grown in rich media induced with 1 mM IPTG, while a filled diamond indicates the β-galactosidase activity that was obtained when MG1655 or CSH27 cells were grown in M9 minimal lactose media.

Demonstrating that pLAC11 constructs can be tightly regulated. pLAC11 was designed to provide researchers with an expression vector that could be utilized to conduct physiological experiments in which a cloned gene is studied under completely repressed conditions where it is off or partially induced conditions where it is expressed at physiologically relevant levels. FIG. 5 demonstrates how a pLAC11-lacZ construct can be utilized to mimic chromosomally expressed lacZ that occurs under various physiological conditions by varying the amount of IPTG inducer that is added. ALS226 cells containing pLAC11-lacZ were grown to mid-log in rich media that contained varying amounts of IPTG and then β-galactosidase activity was assayed. Also indicated in the graph are the average β-galactosidase activities obtained for strains with a single chromosomal copy of the wild-type lacZ gene that were grown under different conditions.

To demonstrate just how regulable pLAC11 is, the recA gene was cloned into the pLAC11 vector and transformed into cells which contained a null recA allele in the chromosome. As the results in Table 7 clearly show, recombination cannot occur in a host strain which contains a nonfunctional RecA protein and thus P1 lysates which provide a Tn10dKan transposon cannot be used to transduce the strain to Kan$^R$ at a high frequency. recA$^-$ cells which also contain the pLAC11-recA construct can be transduced to Kan$^R$ at a high frequency when grown under induced conditions but cannot be transduced to Kan$^R$ when grown under repressed conditions.

TABLE 7

The recombination (−) phenotype of a recA null mutant strain can be preserved with a pLAC11-recA (wild-type) construct under repressed conditions

| Strain | Repressed Conditions Number of Kan$^R$ transductants | Induced Conditions Number of Kan$^R$ transductants |
|---|---|---|
| ALS225 (recA$^+$) | 178,000 | 182,000 |
| ALS514 (recA$^-$) | 5 | 4 |
| ALS515 (recA$^-$ pLAC11-recA) | 4 | 174,000 |

The data presented in Table 7 are the number of Kan$^R$ transductants that were obtained from the different MC1061 derivative strains when they were transduced with a P1 lysate prepared from strain ALS598 which harbored a Tn10dKan transposon insertion. Overnights were prepared from each of these strains using either rich medium to which glucose was added at a final concentration of 0.2% (repressed conditions) or rich medium to which IPTG was added at a final concentration of 1 mM (induced conditions). The overnights were then diluted 1 to 10 into the same medium which contained CaCl$_2$ added to a final concentration of 10 mM and aerated for two hours to make them competent for transduction with P1 phage. Cells were then spectrophotometrically normalized and 0.1 ml aliquots of cells at an OD$_{550}$ of 5 were transduced with 0.1 ml of concentrated P1 lysate as well as 0.1 ml of P1 lysates that had been diluted to $10^{-1}$, $10^{-2}$, or $10^{-3}$. 0.2 ml of 0.1 M Sodium Citrate was added to the cell/phage mixtures and 0.2 ml of the final mixtures were plated onto Rich Kanamycin plates and incubated overnight at 37° C. The total number of Kan$^R$ colonies were then counted. ALS225 recA$^+$ data points were taken from the transductions which used the $10^{-3}$ diluted phage, while ALS514 recA$^-$ data points were taken from the transductions which used the concentrated phage. The data points for ALS515 recA$^-$ pCyt-3-recA grown under repressed conditions were taken from the transductions which used the concentrated phage, while the data points for ALS515 recA$^-$ pCyt-3-recA grown under induced conditions were taken from the transductions which used the $10^{-3}$ diluted phage.

Testing various sources of Lac for trans repression of pLAC11. Because pLAC11 was designed to be used with an extraneous source of LacI repressor, different episomal or plasmid sources of LacI which are routinely employed by researchers were tested. Since one of the LacI sources also contained the lacZ gene, a reporter construct other than pLAC11-lacZ was required and thus a pLAC11-xylE construct was engineered. Table 8 shows the results of this study.

All of the LacI sources that were tested proved to be adequate to repress expression from pLAC11, however, some were better than others. The basal level of expression that was observed with F's which provided lacI$^{q1}$ or with the plasmid pMS421 which provided lacI$^q$ at approximately six copies per cell was lower than the basal level of expression that was observed with F's which provided lacI$^q$ all three times that the assay was run. Unfortunately, however, the xylE gene could not be induced as high when lacI$^{q1}$ on a F' or lacI$^q$ on a plasmid was used as the source of Lac repressor.

TABLE 8

Catechol 2,3-dioxygenase levels obtained for a pLAC11-xylE construct when Lac repressor is provided by various sources

| | | Catechol 2,3-dioxygenase activity in milliunits/mg | |
|---|---|---|---|
| Strain | Source of LacI | Repressed Conditions | Induced Conditions |
| ALS224 | None | 32.7 | 432.8 |
| ALS535 | F'lacIq Δ(lacZ)M15 proA+B+ Tn10 | .3 | 204.4 |
| ALS527 | F'lacIq Δ(lacZ)M15 proA+B+ | .3 | 243.3 |
| ALS227 | pMS421 lacI$^q$ | .2 | 90.9 |
| ALS225 | F'lacIq$^I$ Z$^+$ Y$^+$ A$^+$ | .2 | 107.4 |
| ALS226 | F'lacIq$^I$ Z::Tn5 Y$^+$ A$^+$ | .2 | 85.1 |

The wild-type xylE gene was cloned into the pLAC11 vector and the resulting pLAC11-xylE construct was then transformed into each of the MC1061 derivative strains listed in the table. Rich overnights were diluted 1 to 200 in either Rich Glucose or Rich IPTG media and grown until they reached mid-log(OD$_{550}$=0.5). Cell extracts were then prepared and catechol 2,3-dioxygenase assays were performed as described by Zukowski, et. al. (Proc. Natl. Acad. Sci. U.S.A. 80:1101-1105 (1983)). The average values obtained in three different experiments are listed in the table. Standard deviation is not shown but was less 15 than 10% in each case.

Discussion

Most of the routinely employed expression vectors rely on lac control in order to overproduce a gene of choice. The lac promoter/operator functions as it does due to the interplay of three main components. First, the wild-type lac-10 region (TATGTT) is very weak. c-AMP activated CAP protein is able to bind to the CAP site just upstream of the −35 region which stimulates binding of RNA polymerase to the weak −10 site. Repression of the lac promoter is observed when glucose is the main carbon source because very little c-AMP is present which results in low amounts of available c-AMP activated CAP protein. When poor carbon sources such as lactose or glycerol are used, c-AMP levels rise and large amounts of c-AMP activated CAP protein become available. Thus induction of the lac promoter can occur. Second, Lac repressor binds to the lac operator. Lac repressor can be overcome by allolactose which is a natural byproduct of lactose utilization in the cell, or by the gratuitous inducer, IPTG. Third, the lac operator can form stable loop structures which prevents the initiation of transcription due to the interaction of the Lac repressor with the lac operator (O1) and one of two auxiliary operators, O2 which is located downstream in the coding region of the lacZ gene, or O3 which is located just upstream of the CAP binding site.

While binding of Lac repressor to the lac operator is the major effector of lac regulation, the other two components are not dispensable. However, most of the routinely used lac regulable vectors either contain mutations or deletions which alter the affect of the other two components. The pKK223-3 (J. Brosius et al., Proc. Natl. Acad. Sci. USA. 81:6929-6933 (1984)), pKK233-2 (E. Amann et al., Gene. 40:183-190 (1985)), pTrc99A (E. Amann et al., Gene. 69:301-315 (1988)), and pET family of vectors (F. Studier, Method Enzymol. 185:60-89 (1990)) contain only the lac operator (O1) and lack both the CAP binding site as well as the O3 auxiliary operator. pKK223-3, pKK233-2, and pTrc99 use a trp-lac hybrid promoter that contains the trp-35 region and the lacUV5-10 region which contains a strong TATAAT site instead of the weak TATGTT site. The pET family of vectors use the strong T7 promoter. Given this information, perhaps it is not so surprising researchers have found it is not possible to tightly shut off genes that are cloned into these vectors.

The purpose of the studies described in Example I was to design a vector which would allow researchers to better regulate their cloned genes in order to conduct physiological experiments. The expression vectors described herein were designed utilizing the wild-type lac promoter/operator in order to accomplish this purpose and include all of the lac control region, without modification, that is contained between the start of the O3 auxiliary operator through the end of the O1 operator. As with all lac based vectors, the pLAC11, pLAC22, and pLAC33 expression vectors can be turned on or off by the presence or absence of the gratuitous inducer IPTG.

Because the new vector, pLAC11, relies on the wild-type lac control region from the auxiliary lac O3 operator through the lac O1 operator, it can be more tightly regulated than the other available expression vectors. In direct comparison studies with pKK-223-3, pKK233-2, pTrc99A, and pET-21(+), the lowest level of expression under repressed conditions was achievable with the pLAC11 expression vector. Under fully induced conditions, pLAC11 expressed lacZ protein that was comparable to the levels achievable with the other expression vectors. Induction ratios of 1000× have been observed with the wild-type lac operon. Of all the expression vectors that were tested, only pLAC11 yielded induction ratios which were comparable to what has been observed with the wild-type lac operon. It should be noted that the regulation achievable by pLAC11 may be even better than the data in Table 6 indicates. Because lacZ was used in this test, the auxiliary lac $O_2$ operator which resides in the coding region of the lacZ gene was provided to the pKK223-3, pKK233-2, pTrc99A, and pET-21(+) vectors which do not normally contain either the O2 or O3 auxiliary operators. Thus the repressed states that were observed in the study in Table 6 are probably lower than one would normally observe with the pKK223-3, pKK233-2, pTrc99A, and pET-21(+) vectors.

To meet the expression needs required under different experimental circumstances, two additional expression vectors which are derivatives of pLAC11 were designed. pLAC22 provides lacIq on the vector and thus unlike pLAC11 does not require an extraneous source of LacI for its repression. pLAC33 contains the mutated ColE1 replicon from pUC8 and thus allows proteins to be expressed at much higher levels due to the increase in the copy number of the vector. Of all the expressions that were evaluated in direct comparison studies, the highest level of protein expression under fully induced conditions was achieved using the pLAC33 vector. Because the cloning regions are identical in pLAC11, pLAC22, and pLAC33, genes that are cloned into one of these vectors can be trivially subcloned into either of the other two vectors depending on experimental circumstances. For physiological studies, pLAC11 is the best suited of the three vectors. If, however, the bacterial strain of choice can not be modified to introduce elevated levels of Lac repressor protein which can be achieved by F's or compatible plasmids that provide $lacI^q$ or $lacI^{q1}$, the pLAC22 vector can be utilized. If maximal overexpression of a gene product is the goal, then the pLAC33 vector can be utilized.

Numerous experiments call for expression of a cloned gene product at physiological levels; i.e., at expression levels that are equivalent to the expression levels observed for the chromosomal copy of the gene. While this is not easily achievable with any of the commonly utilized expression vectors, these kinds of experiments can be done with the pLAC11 expression vector. By varying the IPTG concentrations, expression from the pLAC11 vector can be adjusted to match the expression levels that occur under different physiological conditions for the chromosomal copy of the gene. In fact, strains which contain both a chromosomal null mutation of the gene in question and a pLAC11 construct of the gene preserve the physiological phenotype of the null mutation under repressed conditions.

Because the use of Lac repressor is an essential component of any expression vector that utilizes the lac operon for its regulation, the ability of different source of LacI to repress the pLAC11 vector was also investigated. Researchers have historically utilized either $lacI^q$ constructs which make 10 fold more Lac repressor than wild-type lacI or $lacI^{q1}$ constructs which make 100 fold more Lac repressor than wild-type lacI (B. Müller-Hill, Prog. Biophys. Mol. Biol. 30:227-252 (1975)). The greatest level of repression of pLAC11 constructs could be achieved using F's which provided approximately one copy of the $lacI^{q1}$ gene or a multicopy compatible plasmid which provided approximately six copies of the $lacI^q$ gene. However, the induction that was achievable using these lacI sources was significantly lower than what could be achieved when F's which provided approximately one copy of the $lacI^{q1}$ gene were used to repress the pLAC11 construct. Thus if physiological studies are the goal of an investigation, then F's which provide approximately one copy of the $lacI^{q1}$ gene or a multicopy compatible plasmid which provides approximately six copies of the $lacI^q$ gene can be used to regulate the pLAC11 vector. However, if maximal expression is desired, then F's which provide approximately one copy of the $lacI^q$ gene can be utilized. Alternatively, if a bacterial strain can tolerate prolonged overexpression of an expressed gene and overexpression of a gene product is the desired goal, then maximal expression under induced conditions is obtained when a bacteria strain lacks any source of Lac repressor.

Example II

An In Vivo Approach for Generating Novel Bioactive Peptides that Inhibit the Growth of *E. coli*

A randomized oligonucleotide library containing sequences capable of encoding peptides containing up to 20 amino acids was cloned into pLAC11 (Example I) which allowed the peptides to either be tightly turned off or overproduced in the cytoplasm of *E. coli*. The randomized library was prepared using a [NNN] codon design instead of either the [NN(G,T)] or [NN(G,C)] codon design used by most fusion-phage technology researchers. [NN(G,T)] or [NN(G,C)] codons have been widely used instead of [NNN] codons to eliminate two out of the three stop codons, thus increasing the amount of full-length peptides that can be synthesized without a stop codon (J. Scott et al., Science 249:386-390 (1990); J. Delvin et al., Science 249:404-406 (1990); S. Cwirla et al., Proc. Nat'l. Acad. Sci. U.S.A. 87:6378-6382 (1990)). However, the [NN(G,T)] and [NN(G,C)] oligonucleotide codon schemes eliminate half of the otherwise available codons and, as a direct result, biases the distribution of amino acids that are generated. Moreover, the [NN(G,T)] and [NN(G,C)] codon schemes drastically affect the preferential codon usage of highly expressed genes and removes a number of the codons which are utilized by the abundant tRNAs that are present in *E. coli* (H. Grosjean et al., Gene. 18: 199-209 (1982); T. Ikemura, J. Mol. Biol. 151:389-409 (1981)).

Of the 20,000 peptides screened in this Example, 21 inhibitors of cell growth were found which could prevent the growth of *E. coli* on minimal media. The top twenty inhibitor peptides were evaluated for strength of inhibition, and the putative amino acid sequences of the top 10 "anchorless" inhibitor peptides were examined for commonly shared features or motifs.

Materials and Methods

Media. Rich LB and minimal M9 media used in this study was prepared as in Example I. Ampicillin was used in rich media at a final concentration of 100 ĩg/ml and in minimal media at a final concentration of 50 ĩg/ml. IPTG was added to media at a final concentration of 1 mM.

Chemicals and Reagents. Extension reactions were carried out using Klenow from New England Biolabs while ligation reactions were performed using T4 DNA Ligase from Life Sciences. IPTG was obtained from Diagnostic Chemicals Limited.

Bacterial Strains and Plasmids. ALS225, which is MC1061/F'lacI$^{q1}$Z+Y+A+ (see Example I), was the *E. coli* bacterial strain used in this Example. The genotype for MC1061 is araD139Δ(araABOIC-leu)7679Δ(lac)X74 galU galK rpsL hsr– hsml+ (M. Casadaban et al., J. Mol. Biol. 138: 179-207 (1980)). pLAC11, a highly regulable expression vector, is described in Example I.

Generation of the Randomized Peptide Library. The 93 base oligonucleotide 5'TAC TAT AGA TCT ATG (NNN)$_{20}$ TAA TAA GAA TTC TCG ACA 3' (SEQ ID NO:23), where N denotes an equimolar mixture of the nucleotides A, C, G, or T, was synthesized with the trityl group and subsequently purified with an OPC cartridge using standard procedures. The complementary strand of the 93 base oligonucleotide was generated by an extension/fill-in reaction with Klenow using an equimolar amount of the 18 base oligonucleotide primer 5' TGT CGA GAA TTC TTA TTA 3' (SEQ ID NO:24). After extension, the resulting ds-DNA was purified using a Promega DNA clean-up kit and restricted with EcoR 1 and Bgl II (Promega, Madison, Wis.). The digested DNA was again purified using a Promega DNA clean-up kit and ligated to pLAC11 vector which had been digested with the same two restriction enzymes. The resulting library was transformed into electrocompetent ALS225 *E. coli* cells under repressed conditions (LB, ampicillin, plus glucose added to 0.2%).

Screening of Transformants to Identify Inhibitor Clones. Transformants were screened to identify any that could not grow on minimal media when the peptides were overproduced. Using this scheme, any transformant bacterial colony that overproduces a peptide that inhibits the production or function of a protein necessary for growth of that transformant on minimal media will be identified. Screening on minimal media, which imposes more stringent growth demands on the cell, will facilitate the isolation of potential inhibitors from the library. It is well known that growth in minimal media puts more demands on a bacterial cell than growth in rich media as evidenced by the drastically reduced growth rate; thus a peptide that adversely affects cell growth is more likely to be detected on minimal media. Screening was carried out using a grid-patching technique. Fifty clones at a time were patched onto both a rich repressing plate (LB Amp glucose) and a minimal inducing plate (M9 glycerol Amp IPTG) using an ordered grid. Patches that do not grow are sought because presumably these represent bacteria that are being inhibited by the expressed bioactive peptide. To verify that all of the inhibitors were legitimate, plasmid DNA was made from each inhibitory clone (QIA Prep Spin Miniprep kit; Qiagen Cat. No. 27104) and transformed into a fresh background (ALS225 cells), then checked to confirm that they were still inhibitory on plates and that their inhibition was dependent on the presence of the inducer, IPTG.

Growth Rate Analysis in Liquid Media. Inhibition strength of the peptides was assessed by subjecting the inhibitory clones to a growth rate analysis in liquid media. To determine the growth rate inhibition, starting cultures of both the peptides to be tested and a control strain which contains pLAC11 were diluted from a saturated overnight culture to an initial $OD_{550}$ of ~0.01. All cultures were then induced with 1 mM IPTG and $OD_{550}$ readings were taken until the control culture reached an $OD_{550}$ of ~0.5. The hypothetical data in Table 9 shows that when the control strain reaches an $OD_{550}$ of about 0.64 (at about 15 hours), a strain which contains a peptide that inhibits the growth rate at 50% will only have reached an $OD_{550}$ of only about 0.08. Thus, the growth of a 50% inhibited culture at 15 hours (i.e., the $OD_{550}$ at 15 hours, which is proportional to the number of cells in a given volume of culture) is only about 12.5% (that is, 0.08/0.64×100) of that of a control strain after the same amount of time, and the inhibitor peptide would thus have effectively inhibited the growth of the culture (as measured by the $OD_{550}$ at the endpoint) by 87.5% (=100%–12.5%).

TABLE 9

Hypothetical data from a peptide that inhibits growth rate at 30%, 50% and 70%

| Time in Hours | 0D550 readings on a control culture which contains pLAC11 | OD550 readings on a culture which contains a peptide that inhibits the growth rate at ... | | |
|---|---|---|---|---|
| | | 25% | 50% | 75% |
| 0 | .010 | .010 | .010 | .010 |
| 2.5 | .020 | .017 | .015 | .012 |
| 5 | .040 | .028 | .020 | .014 |
| 7.5 | .080 | .047 | .030 | .017 |
| 10 | .160 | .079 | .040 | .020 |
| 12.5 | .320 | .133 | .060 | .024 |
| 15 | .640 | .226 | .080 | .028 |

Figure 6:
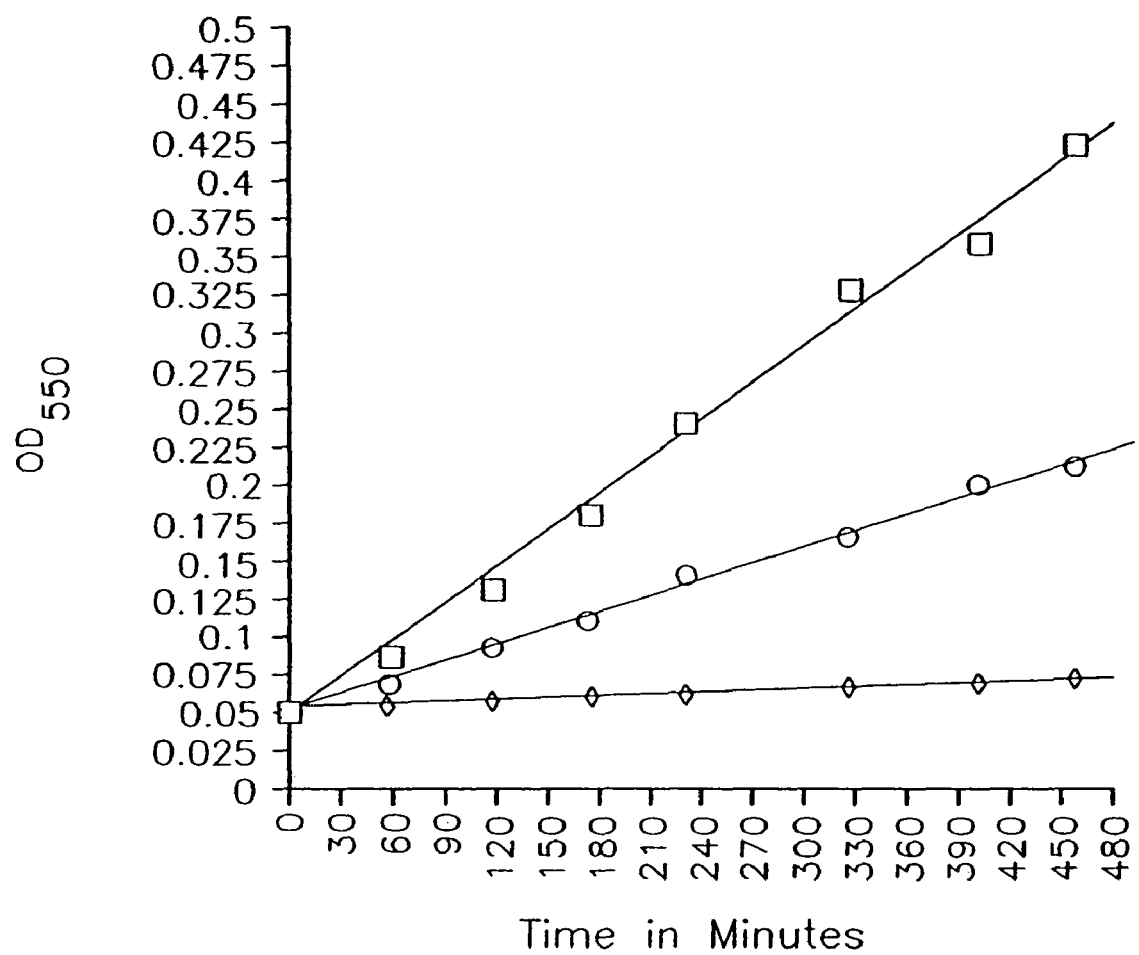
FIG. 6 shows growth curves depicting the inhibitory effects of a two day inhibitor (pPep12) versus a one day inhibitor (pPep1). Data points for the control, pLAC 11, for pPep 1, and for pPep 12, are indicated by squares, circles, and triangles, respectively.

An example is shown in FIG. 6, wherein ALS225 cells containing the pLAC11 vector (control), and either the one day inhibitor pPep1 or the two day inhibitor pPep12 (see below), were grown in minimal M9 glycerol media with IPTG added to 1 mM. $OD_{550}$ readings were then taken hourly until the cultures had passed log phase. Growth rates were determined by measuring the spectrophotometric change in $OD_{550}$ per unit time within the log phase of growth. The inhibition of the growth rate was then calculated for the inhibitors using pLAC11 as a control.

Sequencing the Coding Regions of the Inhibitor Peptide Clones. The forward primer 5' TCA TTA ATG CAG CTG GCA CG 3' (SEQ ID NO:25) and the reverse primer 5' TTC ATA CAC GGT GCC TGA CT 3' (SEQ ID NO:26) were used to sequence both strands of the top ten "anchorless" inhibitor peptide clones identified by the grid-patching technique.

If an error-free consensus sequence could not be deduced from these two sequencing runs, both strands of the inhibitor peptide clones in question were resequenced using the forward primer 5' TAG CTC ACT CAT TAG GCA CC 3' (SEQ ID NO:27) and the reverse primer 5' GAT GAC GAT GAG CGC ATT GT 3' (SEQ ID NO:28). The second set of primers were designed to anneal downstream of the first set of primers in the pLAC11 vector.

Generating Antisense Derivatives of the Top Five "Anchorless" Inhibitor Clones.

Oligonucleotides were synthesized which duplicated the DNA insert contained between the Bgl II and EcoR I restriction sites for the top five "anchorless" inhibitor peptides as shown in Table 12 with one major nucleotide change. The "T" of the ATG start codon was changed to a "C" which resulted in an ACG which can not be used as a start codon. The oligonucleotides were extended using the same 18 base oligonucleotide primer that was used to build the original peptide library. The resulting ds-DNA was then restricted, and cloned into pLAC11 exactly as described in the preceding section "Generating the randomized peptide library." The antisense oligonucleotides that were used are as follows:

pPep1(antisense):
(SEQ ID NO: 29)
5'TAC TAT AGA TCT ACG GTG ACT GAA TTT TGT GGC TTG

TTG GAC CAA CTG CCT TAG TAA TAG TGG AAG GCT GAA

ATT AAT AAG AAT TCT CGA CA 3';

pPep5(antisense):
(SEQ ID NO: 30)
5'TAC TAT AGA TCT ACG TGG CGG GAC TCA TGG ATT AAG

GGT AGG GAC GTG GGG TTT ATG GGT TAA AAT AGT TTG

ATA ATA AGA ATT CTC GAC A 3' pPep12(antisense):
(SEQ ID NO: 31)
5'TAC TAT AGA TCT ACG AAC GGC CGA ACC AAA CGA ATC

CGG GAC CCA CCA GCC GCC TAA ACA GCT ACC AGC TGT

GGT AAT AAG AAT TCT CGA CA 3' pPep13(antisense):
(SEQ ID NO: 32)
5'TAC TAT AGA TCT ACG GAC CGT GAA GTG ATG TGT GCG

GCA AAA CAG GAA TGG AAG GAA CGA ACG CCA TAG GCC

GCG TAA TAA GAA TTC TCG ACA 3' pPep19(antisense):
(SEQ ID NO: 33)
5'TAC TAT AGA TCT ACG AGG GGC GCC AAC TAA GGG GGG

GGG AAG GTA TTT GTC CCG TGC ATA ATC TCG GGT GTT

GTC TAA TAA GAA TTC TCG ACA 3'

Results

Identifying and Characterizing Inhibitor Peptides from the Library. Approximately 20,000 potential candidates were screened as described hereinabove, and 21 IPTG-dependent growth inhibitors were isolated. All the inhibitors so identified were able to prevent the growth of the E. coli bacteria at 24 hours, and three of the 21 inhibitors were able to prevent the growth of the E. coli bacteria at 48 hours, using the grid patching technique. These three inhibitors were classified as "two day" inhibitors; the other 18 were classified as "one-day" inhibitors.

Results from the growth rate analysis for candidate peptide inhibitors are shown in Table 10. The % inhibition of the growth rate was calculated by comparing the growth rates of cells that contained induced peptides with the growth rate of cells that contained the induced pLAC11 vector. Averaged values of three independent determinations are shown.

TABLE 10

Ability of the Inhibitor Peptides to Inhibit Cell Growth

| Inhibitor | Type | % Inhibition |
|---|---|---|
| pLAC11 (control) | — | 0 |
| pPep1 | 1 Day | 25 |
| pPep2 | 1 Day | 23 |
| pPep3 | 2 Day | 80 |
| pPep4 | 1 Day | 21 |
| pPep5 | 1 Day | 24 |
| pPep6 | 1 Day | 27 |
| pPep7 | 1 Day | 26 |
| pPep8 | 1 Day | 29 |
| pPep9 | 1 Day | 22 |
| pPep10 | 1 Day | 24 |
| pPep11 | 1 Day | 22 |
| pPep12 | 2 Day | 82 |
| pPep13 | 1 Day | 28 |
| pPep14 | 2 Day | 71 |
| pPep15 | 1 Day | 23 |
| pPep16 | 1 Day | 24 |
| pPep17 | 1 Day | 28 |
| pPep18 | 1 Day | 24 |
| pPep19 | 1 Day | 29 |
| pPep20 | 1 Day | 19 |
| pPep21 | 1 Day | 23 |

Of the 21 peptides that were tested, the one-day inhibitor peptides inhibited the bacterial growth rate at a level of approximately 25%, while the two-day inhibitor peptides inhibited the bacterial growth rate at levels greater than 75%. As can be seen from the hypothetical data in Table 9, a one-day inhibitor which inhibited the growth rate at 25% would have only reached an $OD_{550}$ of 0.226 when the control strain reached an $OD_{550}$ of 0.64. At that point in time, the growth of the culture that is inhibited by a one-day inhibitor (as measured by the end-point $OD_{550}$) only be only 35.3% of that of a control strain at that point; thus the inhibitor peptide would have effectively inhibited the growth of the culture by 64.7%. A two-day inhibitor which inhibited the growth rate at 75% would have only reached an $OD_{550}$ of 0.028 when the control strain reached an $OD_{550}$ of 0.64. Thus the growth of the culture that is being inhibited by a two-day inhibitor will only be 4.4% of that of the control strain at this point, and the inhibitor peptide would have effectively inhibited the growth of the culture by 95.6%. These calculations are consistent with the observation that two-day inhibitors prevent the growth of bacteria on plates for a full 48 hours while the one-day inhibitors only prevent the growth of bacteria on plates for 24 hours.

All 21 candidates were examined using restriction analysis to determine whether they contained 66 bp inserts as expected. While most of them did, the two-day inhibitors pPep3 and pPep14 were found to contain a huge deletion. Sequence analysis of these clones revealed that the deletion had caused the carboxy-terminal end of the inhibitor peptides to become fused to the amino-terminal end of the short 63 amino acid Rop protein. The rop gene, which is part of the ColE1 replicon, is located downstream from where the oligonucleotide library is inserted into the pLAC11 vector.

Sequence Analysis of the Top 10 "Anchorless" Inhibitor Peptides. The DNA fragments comprising the sequences encoding the top 10 "anchorless" inhibitor peptides (i.e., excluding the two Rop fusion peptides) were sequenced, and their coding regions are shown in Table 11. Stop codons are represented by stars, and the landmark Bgl II and EcoR I restriction sites for the insert region are underlined. Since the ends of the oligonucleotide from which these inhibitors were constructed contained these restriction sites, the oligonucleotide was not gel isolated when the libraries were prepared in order to maximize the oligonucleotide yields. Because of this, several of the inhibitory clones were found to contain one (n−1) or two (n−2) base deletions in the randomized portion of the oligonucleotide.

start codon. Interestingly, the start sites of several proteins such as Rop are identical to that proposed for the pPep 17 peptide (G. Cesareni et al., Proc. Natl. 35 Acad. Sci. USA. 79:6313-6317 (1982)). The average and median length for the 8 peptides whose termination signals occurred before or at the double TAA TAA termination site was 13 amino acids.

TABLE 11

Sequence analysis of the insert region from the top 10 inhibitory clones and the peptides that they are predicted to encode

```
pPep1 - 13 aa
CAG GAA AGA TCT ATG GTC ACT GAA TTT TGT GGC TTG TTG GAC CAA CTG CCT TAG TAA TAG TGG AAG    (SEQ ID NO: 35)
             M   V   T   E   F   C   G   L   L   D   Q   L   P   *   *   *                 (SEQ ID NO: 34)
                341
GCT GAA ATT AAT AAG AAT TC pPep5 - 16 aa
CAG GAA AGA TCT ATG TGG CGG GAC TCA TGG ATT AAG GGT AGG GAC GTG GGG TTT ATG GGT TAA AAT    (SEQ ID NO: 37)
             M   W   R   D   S   W   I   K   G   R   D   V   G   F   M   G   *             (SEQ ID NO: 36)
AGT TTG ATA ATA AGA ATT C pPep6 - 42 aa - last 25 aa could form a hydrophobic membrane-spanning domain
CAG GAA AGA TCT ATG TCA GGG GGA CAT GTG ACG AGG GAG TGC AAG TCG GCG ATG TCC AAT CGT TGG    (SEQ ID NO: 39)
             M   S   G   G   H   V   T   R   E   C   K   S   A   M   S   N   R   W   I    (SEQ ID NO: 38)
ATC TAC GTA ATA AGA ATT CTC ATG TTT GAC AGC TTA TCA TCG ATA AGC TTT AAT GCG GTA GTT TAT
  V   I   R   I   L   M   F   D   S   L   S   S   I   S   F   N   A   V   V   Y
CAC AGT Y *
 H   S   Y * pPep7 - 6 aa
CAG GAA AGA TCT ATG TAT TTG TTC ATC GGA TAA TAC TTA ATG GTC CGC TGG AGA ACT TCA GTT TAA    (SEQ ID NO: 41)
             M   Y   L   F   I   G   *                                                     (SEQ ID NO: 40)
TAA GAA TTC pPep8 - 21 aa
CAG GAA AGA TCT ATG CTT CTA TTT GGG GGG GAC TGC GGG CAG AAA GCC GGA TAC TTT ACT GTG CTA    (SEQ ID NO: 42)
             M   L   L   F   G   G   D   C   G   Q   K   A   G   Y   F   T   V   L         (SEQ ID NO: 43)
CCG TCA AGG TAA TAA GAA TTC
 P   S   R   *   * pPep10 - 20 aa - predicted to be 45% β-sheet -amino acids 6-14
CAG GAA AGA TCT ATG ATT GGG GGA TCG TTG AGC TTC GCC TGG GCA ATA GTT TGT AAT AAG AAT TCT    (SEQ ID NO: 44)
             M   I   G   G   S   L   S   F   A   W   A   I   V   C   N   K   N   S        (SEQ ID NO: 45)
CAT GTT TGA
 H   V   * pPep12 - 14 aa
CAG GAA AGA TCT ATG AAC GGC CGA ACC AAA CGA ATC CGG GAC CCA CCA GCC GCC TAA ACA GCT ACC    (SEQ ID NO: 47)
             M   N   G   R   T   K   R   I   R   D   P   P   A   A   *                    (SEQ ID NO: 46)
AGC TGT GGT AAT AAG AAT TC pPep13 - 18 aa - predicted to be 72% α-helical - amino acids 3-15
CAG GAA AGA TCT ATG GAC CGT GAA GTG ATG TGT GCG GCA AAA CAG GAA TGG AAG GAA CGA ACG CCA    (SEQ ID NO: 49)
             M   D   R   E   V   M   C   A   A   K   Q   E   W   K   E   R   T   P        (SEQ ID NO: 48)
TAG GCC GCG TAA TAA GAA TTC
 * pPep17 - 12 aa
CAG GAA AGA TCT ATG TAG CCC AAT GCA CTG GGA GCA CGC GTG TTA GGT CTA GAA GCC ACG TAC CCA    (SEQ ID NO: 50)
             M   *                       M   L   G   L   E   A   T   Y   P                (SEQ ID NO: 51)
TTT AAT CCA TAA TAA GAA TTC
 F   N   P   *   * pPep19 - 5 aa
CAG GAA AGA TCT ATG AGG GGC GCC AAC TAA GGG GGG GGG AAG GTA TTT GTC CCG TGC ATA ATC TCG    (SEQ ID NO: 53)
             M   R   G   A   N   *                                                        (SEQ ID NO: 52)
GGT GTT GTC TAA TAA GAA TTC
```

Eight out of the top 10 inhibitors were predicted to encode peptides that terminate before the double TAA TAA termination site, which was engineered into the oligonucleotide. Two of the inhibitors, pPep6 and pPep10, which contain deletions within the randomized portion of the oligonucleotide, are terminated beyond the EcoR I site. One of the inhibitors, pPep17, contains a termination signal just after the ATG start codon. However, just downstream from this is a Shine Dalgarno site and a GTG codon, which should function as the The characteristics of the predicted coding regions of the inhibitor peptides proved to be quite interesting. Three out of the top 10 peptides, pPep1, pPep13, and pPep17, contained a proline residue as their last (C-terminal) amino acid. Additionally, one of the peptides, pPep12, contained 2 proline residues near the C-terminus, at the n−2 and n−3 positions. Thus there appears to be a bias for the placement of proline residues at or near the end of several of the inhibitory peptides. Secondary structure analysis predicted that 3 out of the 10 peptides contained a known motif that could potentially form a very stable structure. pPep13, a peptide containing a C-terminal proline, is predicted to be 72% α-helical, pPep 10 is predicted to be 45% β-sheet, and pPep6 is predicted to form a hydrophobic membrane spanning domain.

Verifying that the Inhibitory Clones do not Function as Antisense. To rule out the possibility that the bioactivity of the inhibitory clones resulted from their functioning as antisense RNA or DNA (thus hybridizing to host DNA or RNA) rather than by way of the encoded peptides, the insert regions between the Bgl II and EcoR I sites for the top five inhibitors from Table 10 were recloned into the pLAC11 vector using oligonucleotides which converted the ATG start codon to an ACG codon thus abolishing the start site. In all five cases the new constructs were no longer inhibitory (see Table 12), thus confirming that it is the encoded peptides that causes the inhibition and not the DNA or transcribed mRNA.

TABLE 12

Antisense test of the top 5 "anchorless" inhibitory peptides

| Inhibitory peptide | % inhibition versus pLAC11 control | Antisense construct | % inhibition versus pLAC11 control |
|---|---|---|---|
| pPep1 | 26 | pPep1-anti | 0 |
| pPep5 | 23 | pPep5-anti | 0 |
| pPep12 | 80 | pPep12-anti | 0 |
| pPep13 | 28 | pPep13-anti | 0 |
| pPep19 | 29 | pPep19-anti | 0 |

Growth rates for cells containing the induced inhibitors or antisense constructs were determined and then the % inhibition was calculated by comparing these values to the growth rate of cells that contained the induced pCyt-3 vector.

Discussion

Use of the tightly regulable pLAC11 expression vector made possible the identification of novel bioactive peptides. The bioactive peptides identified using the system described in this Example inhibit the growth of the host organism (*E. coli*) on minimal media. Moreover, bioactive peptides thus identified are, by reason of the selection process itself, stable in the host's cellular environment. Peptides that are unstable in the host cell, whether or not bioactive, will be degraded; those that have short half-lives are, as a result, not part of the selectable pool. The selection system thus makes it possible to identify and characterize novel, stable, degradation-resistant bioactive peptides in essentially a single experiment.

The stability of the inhibitory peptides identified in this Example may be related to the presence of certain shared structural features. For example, three out of the top 10 inhibitory "anchorless" (i.e., non-Rop fusion) peptides contained a proline residue as their last amino acid. According to the genetic code, a randomly generated oligonucleotide such as the one used in this Example has only a 6% chance of encoding a proline at a given position, yet the frequency of a C-terminal proline among the top ten inhibitory peptides is a full 30%. This 5-fold bias in favor of a C-terminal proline is quite surprising, because although the presence of proline in a polypeptide chain generally protects biologically active proteins against nonspecific enzymatic degradation, a group of enzymes exists that specifically recognize proline at or near the N- and C-termini of peptide substrates. Indeed, proline-specific peptidases have been discovered that cover practically all situations where a proline residue might occur in a potential substrate (D. F. Cunningham et al., Biochimica et Biophysics Acta 1343:160-186 (1997)). For example, although the N-terminal sequences Xaa-Pro-Yaa- and Xaa-Pro-Pro-Yaa (SEQ ID NO:54) have been identified as being protective against nonspecific N-terminal degradation, the former sequence is cleaved by aminopeptidase P (at the Xaa-Pro bond) and dipeptidyl peptidases IV and II (at the -Pro-Yaa-bond)) (Table 5, G. Vanhoof et al., FASEB J. 9:736-44 (1995); D. F. Cunningham et al., Biochimica et Biophysics Acta 1343:160-186 (1997)); and the latter sequence, present in bradykinin, interleukin 6, factor XII and erythropoietin, is possibly cleaved by consecutive action of aminopeptidase P and dipeptidyl peptidase IV (DPPIV), or by prolyl oligopeptidase (post Pro-Pro bond) (Table 5, G. Vanhoof et al., FASEB J. 9:736-44 (1995)). Prolyl oligopeptidase is also known to cleave Pro-Xaa bonds in peptides that contain an N-terminal acyl-Yaa-Pro-Xaa sequence (D. F. Cunningham et al., Biochimica et Biophysics Acta 1343:160-186 (1997)). Other proline specific peptidases acting on the N-terminus of substrates include prolidase, proline iminopeptidase and prolinase. Prolyl carboxypeptidase and carboxypeptidase P, on the other hand, cleave C-terminal residues from peptides with proline being the preferred $P_1$ residue (D. F. Cunningham et al., Biochimica et Biophysics Acta 1343:160-186 (1997).

Also of interest with respect to the stability of the inhibitory peptides, three of the top ten (30%) contained motifs that were predicted, using standard protein structure prediction algorithms, to form stable secondary structures. One of the peptides (which also has a C-terminal proline) was predicted to be 72% α-helical. Another was predicted to be 45% β-sheet; this peptide may dimerize in order to effect the hydrogen bonding necessary to form the β-sheet. A third was predicted to possess a hydrophobic membrane spanning domain. According to these algorithms (see, e.g., P. Chou et al., Adv. Enzymol. 47:45-148 (1978); J. Garnier et al., J. Mol. Biol. 120:97-120 (1978); P. Chou, "Prediction of protein structural classes from amino acid composition," In Prediction of Protein Structure and the Principles of Protein Conformation (Fasman, G. D. ed.). Plenum Press, New York, N.Y. 549-586 (1990); P. Klein et al., Biochim. Biophys. Acta 815:468-476 (1985)), a randomly generated oligonucleotide such as the one used in our studies would have had no better than a 1 in a 1000 chance of generating the motifs that occurred in these peptides.

Finally, two of the three two-day inhibitors proved to be fusion peptides in which the carboxyl terminus of the peptides was fused to the amino terminus of the Rop protein. Rop is a small 63 amino acid protein that consists of two antiparallel É-helices connected by a sharp hairpin loop. It is a dispensable part of the ColE1 replicon which is used by plasmids such as pBR322, and it can be deleted without causing any ill-effects on the replication, partitioning, or copy numbers of plasmids that contain a ColE1 ori (X. Soberon, Gene. 9:287-305 (1980). Rop is known to possess a highly stable structure (W. Eberle et al., Biochem. 29:7402-7407 (1990); S. Betz et al., Biochemistry 36:2450-2458 (1997)), and thus it could be serving as a stable protein anchor for these two peptides.

Table 13 lists naturally occurring bioactive peptides whose structures have been determined. Most of these peptides contain ordered structures, further highlighting the importance of structural stabilization. Research on developing novel synthetic inhibitory peptides for use as potential therapeutic agents over the last few years has shown that peptide stability is a major problem that must be solved if designer synthetic peptides are to become a mainstay in the pharmaceutical industry (J. Bai et al., Crit. Rev. Ther. Drug. 12:339-371 (1995); R. Egleton Peptides. 18:1431-1439 (1997); L. Wearley, Crit. Rev Ther Drug Carrier Syst. 8:331-394 (1991). The system described in this Example represents a major advance in the art of peptide drug development by biasing the selection process in favor of bioactive peptides that exhibit a high degree of stability in an intracellular environment.

îg/ml and in minimal media at a final concentration of 50 îg/ml. IPTG was added to media at a final concentration of 1 mM.

TABLE 13

Structural motifs observed in naturally occurring bioactive peptides

| Bioactive Peptide | Size in Amino acids | Structural Motif | Reference |
|---|---|---|---|
| Dermaseptin | 34 | α-helix | Mor et al., Biochemistry, 33: 6642-6650 (1994) |
| Endorphin | 30 | α-helix | Blanc et al., J. Biol. Chem., 258: 8277-8284 (1983) |
| Glucagons | 29 | α-helix | Bedarkar et al., Ciba Found Symp 60: 105-121 (1977) |
| Magainins[a] | 23 | α-helix | Bechinger et al., Protein Sci. 2: 2077-2084 (1993) |
| Mastoparan | 14 | α-helix | Cachia et al., Biochemistry 25: 3553-3562 (1986) |
| Melittin | 26 | α-helix | Terwilliger et al., J. Biol. Chem. 257: 6010-6015 (1982) |
| Motilin | 22 | α-helix | Khan et al., Biochemistry 29: 5743-5751 (1990) |
| PK1 (5-24) | 20 | α-helix | Reed et al., Biochemistry 26: 7641-7647 (1987) |
| Secretin | 27 | α-helix | Gronenborn, et al. FEBS Lett., 215: 88-94 (1987) |
| Atrial Natriuretic Peptide | 28 | disulfide bonds | Misono, et al., Biochem. Biophys. Res. Comm. 119: 524-529 (1984) |
| Calcitonin | 32 | disulfide bonds | Barling et al., Anal. Biochem. 144: 542-552 (1985) |
| Conotoxins[a] | 10-30 | disulfide bonds | Olivera, et al., J. Biol. Chem. 266: 22067-22070 (1991) |
| Defensins[a] | 29-34 | disulfide bonds | Lehrer, et al., Ann. Intern. Med. 109: 127-142 (1988) |
| EETI II | 29 | disulfide bonds | Heitz, et al., Biochemistry 28: 2392-2398 (1989) |
| Oxytocin | 9 | disulfide bonds | Urry, et al., Proc. Natl. Acad. Sci. USA 60: 967-974 (1968) |
| Somatostatin | 14 | disulfide bonds | Namboodiri, et al. J. Biol. Chem. 257: 10030-10032 (1982) |
| Vasopressin | 9 | disulfide bonds | Fong, et al., Biochem. Biophys. Res. Comm. 14: 302-306 (1964) |
| Bombesin | 14 | disordered | Carmona, et al., Biochim. Biophys. Acta 1246: 128-134 (1995) |
| Histatin | 24 | disordered | Xu, et al. J. Dent. Res. 69: 1717-1723 (1990) |
| Substance P | 11 | disordered | Williams and Weaver, J. Biol. Chem. 265: 2505-2513 (1990) |

[a]These peptides belong to multi-member families.

Example III

Directed Synthesis of Stable Synthetically Engineered Inhibitor Peptides

These experiments were directed toward increasing the number of bioactive peptides produced by the selection method described in Example II. In the initial experiment, randomized peptides fused to the Rop protein, at either the N- or C-terminus, were evaluated. In the second experiment, nucleic acid sequences encoding peptides containing a randomized internal amino acid sequence flanked by terminal prolines were evaluated. Other experiments included engineering into the peptides an α-helical structural motif, and engineering in a cluster of opposite charges at the N- and C-termini of the peptide.

Materials and Methods

Media. Rich LB and minimal M9 media used in this study was prepared as described by Miller (see Example I). Ampicillin was used in rich media at a final concentration of 100

Chemicals and Reagents. Extension reactions were carried out using Klenow from New England Biolabs (Bedford, Mass.) while ligation reactions were performed using T4 DNA ligase from Life Sciences (Gaithersburg, Md.) Alkaline phosphatase (calf intestinal mucosa) from Pharmacia (Piscataway, N.J.) was used for dephosphorylation. IPTG was obtained from Diagnostic Chemicals Limited (Oxford, Conn.).

Bacterial Strains and Plasmids. ALS225, which is MC1061/F'lacI$^{q1}$Z+Y+A+, was the *E. coli* bacterial strain used in this study (see Example I). The genotype for MC1061 is araD139 Δ(araABOIC-leu)7679 Δ(lac)X74 galU galK rpsL hsr−hsm+ as previously described. pLAC11 (Example I), a highly regulable expression vector, was used to make p-Rop(C) and p(N)Rop-fusion vectors as well as the other randomized peptide libraries which are described below.

Figure 7:
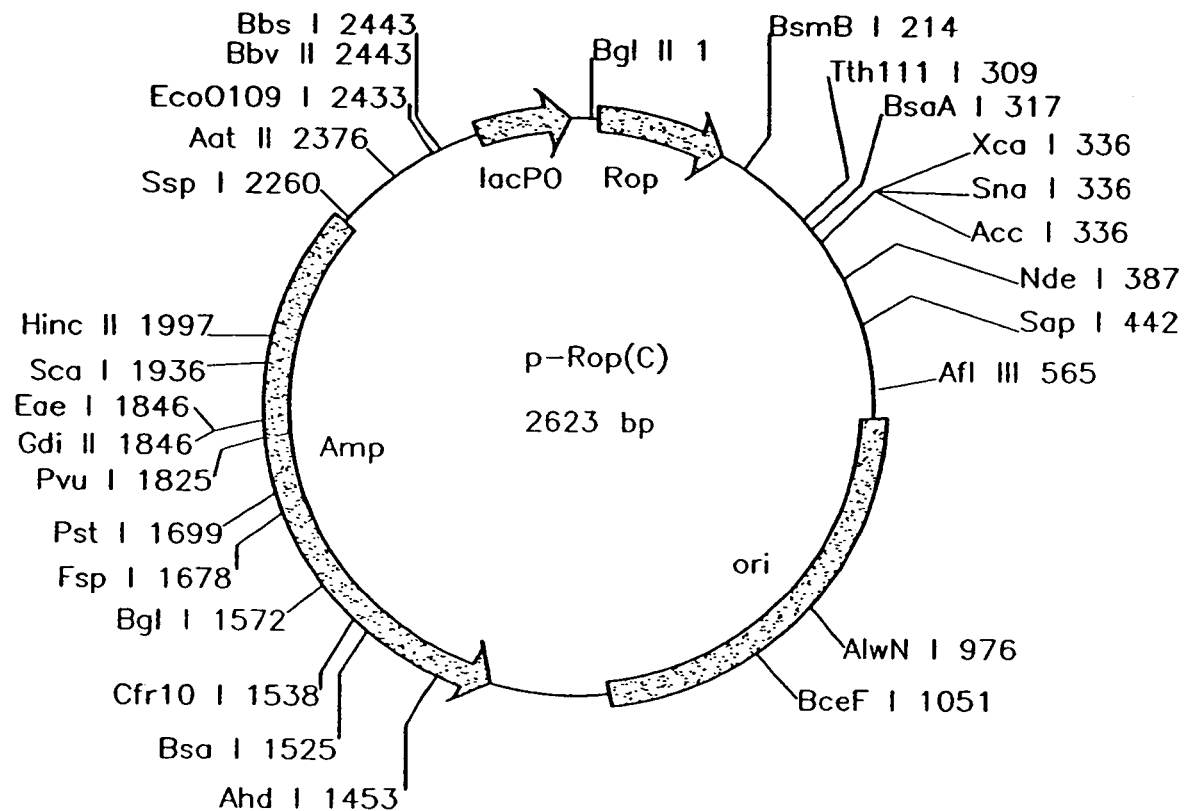
FIG. 7 is a map of the p-Rop(C) fusion vector. The unique restriction sites and the base pair at which they cut are indicated. Other sites of interest are also shown, including Rop (7-198), ori (627-1214), Amp (2245-1385), lacPO (2500-2612).

Construction of the p-Rop(C) Fusion Vector. The forward primer 5'TAC TAT AGA TCT ATG ACC AAA CAG GAA AAA ACC GCC 3' (SEQ ID NO:55) and the reverse primer 5'TAT ACG TAT TCA GTT GCT CAC ATG TTC TTT CCT GCG 3' (SEQ ID NO:56) were used to PCR amplify a 558 bp DNA fragment using pBR322 as a template. This fragment contained a Bgl II restriction site which was incorporated into the forward primer followed by an ATG start codon and the Rop coding region. The fragment extended beyond the Rop stop codon through the Afl III restriction site in pBR322. The amplified dsDNA was gel isolated, restricted with Bgl II and Afl III, and then ligated into the pLAC expression vector which had been digested with the same two restriction enzymes. The resulting p-Rop(C) fusion vector is 2623 bp in size (FIG. 7).

Figure 8:
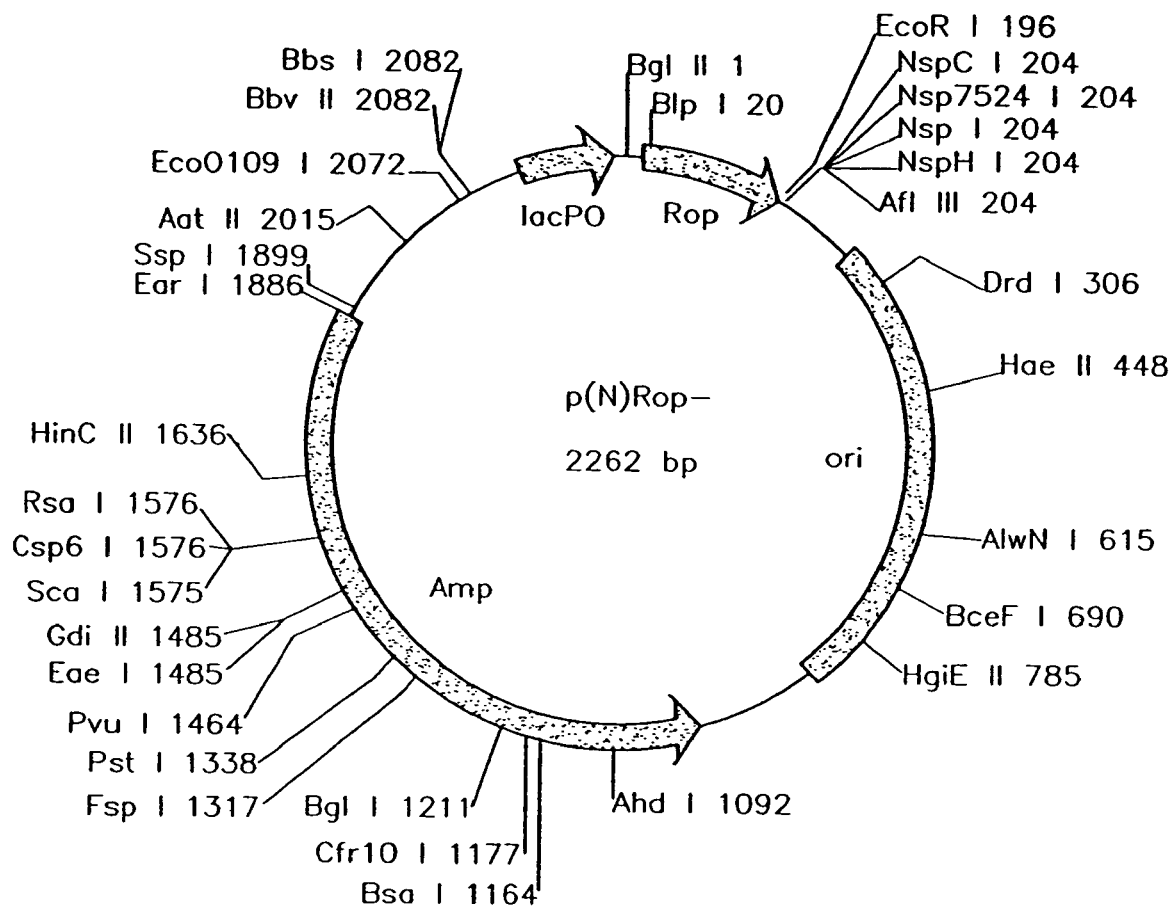
FIG. 8 is a map of the p(N)Rop-fusion vector. The unique restriction sites and the base pair at which they cut are indicated. Other sites of interest are also shown: Rop (7-204), ori (266-853), Amp (1024-1884), lacPO (2139-2251).

Construction of the p(N)Rop-Fusion Vector. The forward primer 5'AAT TCA TAC TAT AGA TCT ATG ACC AAA CAG GAA AAA ACC GC 3' (SEQ ID NO:57) and the reverse primer 5'TAT ATA ATA CAT GTC AGA ATT CGA GGT TTT CAC CGT CAT CAC 3' (SEQ ID NO:58) were used to PCR amplify a 201 bp DNA fragment using pBR322 as a template. This fragment contained a Bgl II restriction site which was incorporated into the forward primer followed by an ATG start codon and the Rop coding region. The reverse primer placed an EcoR I restriction site just before the Rop TGA stop codon and an Afl III restriction site immediately after the Rop TGA stop codon. The amplified dsDNA was gel isolated, restricted with Bgl II and Afl III, and then ligated into the pLAC II expression vector which had been digested with the same two restriction enzymes. The resulting p(N)Rop-fusion vector is 2262 bp in size (FIG. 8).

Generation of Rop Fusion Randomized Peptide Libraries. Peptide libraries were constructed as described in Example II. The synthetic oligonucleotide 5'TAC TAT AGA TCT ATG (NNN)$_{20}$ CAT AGA TCT GCG TGC TGT GAT 3' (SEQ ID NO:59) was used to construct the randomized peptide libraries for use with the p-Rop(C) fusion vector, substantially as described in Example II. The complementary strand of this oligonucleotide was generated by a fill-in reaction with Klenow using an equimolar amount of the oligonucleotide primer 5'ATC ACA GCA CGC AGA TCT ATG 3' were used (SEQ ID NO:60). After extension, the resulting dsDNA was digested with Bgl II and ligated into the pLAC11 expression vector which had been digested with the same restriction enzyme and subsequently dephosphorylated using alkaline phosphatase. Because of the way the oligonucleotide library has been engineered, either orientation of the incoming digested double-stranded DNA fragment results in a fusion product.

To construct the randomized peptide libraries for use with the p(N)Rop fusion vector, the randomized oligonucleotide 5'TAC TAT GAA TTC(NNN)$_{20}$ GAA TTC TGC CAC CAC TAC TAT 3' (SEQ ID NO:61), and the primer 5' ATA GTA GTG GTG GCA GAA TTC 3' (SEQ ID NO:62) were used. After extension, the resulting dsDNA was digested with EcoRI and ligated into the pLAC11 expression vector which had been digested with the same restriction enzyme and subsequently dephosphorylated using alkaline phosphatase. Because of the way the oligonucleotide library has been engineered, either orientation of the incoming digested double-stranded DNA fragment results in a fusion product.

Generation of a Randomized Peptide Library Containing Terminal Prolines. Randomized amino acid peptide libraries containing two proline residues at both the amino and the carboxy terminal ends of the peptides were constructed using the synthetic oligonucleotide 5'TAC TAT AGA TCT ATG CCG CCG (NNN)$_{16}$ CCG CCG TAA TAA GAA TTC GTA CAT 3' (SEQ ID NO:63). The complementary strand of the 93 base randomized oligonucleotide was generated by filling in with Klenow using the oligonucleotide primer 5'ATG TAC GAA TTC TTA TTA CGG CGG 3' (SEQ ID NO:64). After extension, the resulting dsDNA was digested with Bgl II and EcoR I and ligated into the pLAC11 expression vector which had been digested with the same two restriction enzymes. Because the initiating methionine of the peptides coded by this library is followed by a proline residue, the initiating methionine will be removed (F. Sherman et al, Bioessays 3:27-31 (1985)). Thus the peptide libraries encoded by this scheme are 20 amino acids in length.

Generation of a Randomized Hydrophilic α-Helical Peptide Library. Table 14 shows the genetic code highlighted to indicate certain amino acid properties.

TABLE 14

Genetic Code Highlighted to Indicate Amino Acid Properties

| TTT | phe | $h_a$ | TCT | ser | | TAT | tyr | $b_a$ | TGT | cys | |
|-----|-----|-------|-----|-----|---|-----|-----|-------|-----|-----|---|
| TTC | phe | $h_a$ | TCC | ser | | TAC | tyr | $b_a$ | TGC | cys | |
| TTA | leu | $H_a$ | TCA | ser | | TAA | OCH | | TGA | OPA | |
| TTG | leu | $H_a$ | TCG | ser | | TAG | AMB | | TGG | trp | |
| CTT | leu | $H_a$ | CCT | pro | $B_a$ | CAT | *his* | $h_a$ | CGT | *arg* | |
| CTC | leu | $H_a$ | CCC | pro | $B_a$ | CAC | *his* | $h_a$ | CGC | *arg* | |
| CTA | leu | $H_a$ | CCA | pro | $B_a$ | CAA | *gln* | $h_a$ | CGA | *arg* | |
| CTG | leu | $H_a$ | CCG | pro | $B_a$ | CAG | *gln* | $h_a$ | CGG | *arg* | |
| ATT | ile | $h_a$ | ACT | thr | | AAT | *asn* | $b_a$ | AGT | ser | |
| ATC | ile | $h_a$ | ACC | thr | | AAC | *asn* | $b_a$ | AGC | ser | |
| ATA | ile | $h_a$ | ACA | thr | | AAA | *asn* | $h_a$ | AGA | *arg* | |
| ATG | met | $H_a$ | ACG | thr | | AAG | *asn* | $h_a$ | AGG | *arg* | |
| GTT | val | $h_a$ | GCT | ala | $H_a$ | GAT | *asp* | $h_a$ | GGT | gly | $B_a$ |
| GTC | val | $h_a$ | GCC | ala | $H_a$ | GAC | *asp* | $h_a$ | GGC | gly | $B_a$ |
| GTA | val | $h_a$ | GCA | ala | $H_a$ | GAA | *asp* | $h_a$ | GGA | gly | $B_a$ |
| GTG | val | $h_a$ | GCG | ala | $H_a$ | GAG | *asp* | $h_a$ | GGG | gly | $B_a$ |

Boldface amino acids are hydrophobic while *italicized* amino acids are hydrophilic. The propensity for various amino acids to form α-helical structures is also indicated in this table using the conventions first described by Chou and Fasman (P. Chou et al., *Adv. Enzymol.* 47: 45-148 (1978)). $H_a$ = strong α-helix former, $h_a$ = α-helix former, $B_a$ = strong α-helix breaker, $b_a$ = α-helix breaker. The assignments given in this table are the consensus agreement from several different sources. Hydrophilic versus hydrophobic assignments for the amino acids were made from data found in Wolfenden et. al. (Biochemistry. 20: 849-55 (1981)); Miller et. al. (J Mol. Biol. 196: 641-656 (1987)); and Roseman (*J Mol. Biol.* 200: 5 13-22(1988)). The propensity for amino acids to form α-helical structures were obtained from consensus agreements of the Chou and Fasman (P. Chou et al., Adv. Enzymol. 47: 45-148 (1978); P. Chou, "Prediction of protein structural classes from amino acid compositions," in *Prediction of protein structure and the principles of protein conformation* (G. Fasman, G. D. ed.). Plenum Press, New York, N.Y. 549-586 (1990)); Garnier, Osguthorpe, and Robson (*J Mol. Biol.* 120: 97-120 (1978)); and O'Neill and DeGrado (*Science.* 250: 646-65 1 (1990)) methods for predicting secondary structure.

By analyzing the distribution pattern of single nucleotides in the genetic code relative to the properties of the amino acids encoded by each nucleotide triplet, a novel synthetic approach was identified that would yield randomized 18 amino acid hydrophilic peptide libraries with a propensity to form α-helices. According to Table 14, the use of a [(CAG) A(TCAG)] codon mixture yields the hydrophilic amino acids His, Gln, Asn, Lys, Asp, and Glu. These amino acids are most often associated with α-helical motifs except for asparagine, which is classified as a weak α-helical breaker. If this codon mixture was used to build an α-helical peptide, asparagine would be expected to occur in about 17% of the positions, which is acceptable in an α-helical structure according to the secondary structure prediction rules of either Chou and Fasman (P. Chou et al., *Adv. Enzymol.* 47:45-148 (1978); P. Chou, "Prediction of protein structural classes from amino acid compositions," in *Prediction of protein structure and the principles of protein conformation* (G. Fasman, G. D. ed.). Plenum Press, New York, N.Y. 549-586 (1990)) or Garnier, Osguthorpe, and Robson (J. Garnier et al., *J. Mol. Biol.* 120: 97-120 (1978)). Additionally, several well-characterized proteins have been observed to contain up to three $b_a$ breaker amino acids within a similarly sized α-helical region of the protein (T. Creighton, "Conformational properties of polypeptide chains," in *Proteins: structures and molecular properties*, W.H. Freeman and Company, N.Y., 182-186 (1993)). Since in most α-helices there are 3.6 amino acids per complete turn, the 18 amino acid length was chosen in order to generate α-helical peptides which contained 5 complete turns. Moreover, the use of hydrophilic amino acids would be expected to yield peptides which are soluble in the cellular cytosol.

Randomized 18 amino acid hydrophilic α-helical peptide libraries were synthesized using the synthetic oligonucleotide 5'TAC TAT AGA TCT ATG (VAN)$_{17}$ TAA TAA GAA TTC TGC CAG CAC TAT 3' (SEQ ID NO:65). The complementary strand of the 90 base randomized oligonucleotide was generated by filling in with Klenow using the oligonucleotide primer 5'ATA GTG CTG GCA GAA TTC TTA TTA 3' (SEQ ID NO:66). After extension the resulting dsDNA was digested with Bgl II and EcoR I and ligated into the pLAC11 expression vector which had been digested with the same two restriction enzymes.

Generating a Randomized Peptide Library Containing the +/− Charge Ending Motif. Randomized peptide libraries stabilized by the interaction of oppositely charge amino acids at the amino and carboxy termini were generated according to the scheme shown in FIG. 9. To maximize the potential interactions of the charged amino acids, the larger acidic amino acid glutamate was paired with the smaller basic amino acid lysine, while the smaller acidic amino acid aspartate was paired with the larger basic amino acid arginine. To construct the randomized peptide libraries, the synthetic oligonucleotide 5'TAC TAT AGA TCT ATG GAA GAC GAA GAC (NNN)$_{16}$ CGT AAA CGT AAA TAA TAA GAA TTC GTA CAT 3' (SEQ ID NO:67) and the oligonucleotide primer 5'ATG TAC GAA TTC TTA TTA TTT ACG TTT ACG 3' (SEQ ID NO: 68) were used. After extension, the resulting dsDNA was digested with Bgl II and EcoR I and ligated into the pLAC11 expression vector which had been digested with the same two restriction enzymes.

For all libraries of randomized oligonucleotides, N denotes that an equimolar mixture of the four nucleotides A, C, G. and T was used, and V denotes that an equimolar mixture of the three nucleotides A, C and G was used. The resulting libraries were transformed into electrocompetent ALS225 E. coli cells (Example I) under repressed conditions as described in Example II.

Screening of Transformants to Identify Inhibitor Clones. Transformants were initially screened using the grid-patching technique to identify any that could not grow on minimal media as described in Example II when the peptides were overproduced. To verify that all the inhibitors were legitimate, plasmid DNA was made from each inhibitory clone, transformed into a fresh background, then checked to make sure that they were still inhibitory on plates and that their inhibition was dependent on the presence of the inducer, IPTG, as in Example II.

Growth Rate Analysis in Liquid Media. Inhibition strength of the peptides was assessed by subjecting the inhibitory clones to a growth rate analysis in liquid media. Minimal or rich cultures containing either the inhibitor to be tested or the relevant vector as a control were diluted to an initial OD$_{550}$ of approximately 0.01 using new media and induced with 1 mM IPTG. OD$_{550}$ readings were then taken hourly until the cultures had passed log phase. Growth rates were determined as the spectrophotometric change in OD$_{550}$ per unit time within the log phase of growth, and inhibition of the growth rate was calculated for the inhibitors using the appropriate vector as a control.

Results

Isolation and Characterization of Inhibitor Peptides that are Fused at Their Carboxy Terminal End to the Amino Terminal End of the Rop Protein.

Approximately 10,000 peptides protected by the Rop protein at their carboxy terminal end were screened using the grid-patching technique described in Example II, and 16 two day inhibitors were isolated. The inhibitory effects were determined as described in the Example II, using pRop(C) as a control. Unlike the anchorless inhibitors identified in Example II that were only inhibitory on minimal media, many of the Rop fusion inhibitors were also inhibitory on rich media as well, which reflects increased potency. As indicated in Table 15, the inhibitors inhibited the bacterial growth rate at levels that averaged 90% in minimal media and at levels that averaged 50% in rich media. The data in Table 15 is the average of duplicate experiments.

TABLE 15

Inhibitory effects of peptide inhibitors stabilized by fusing the carboxy terminal end of the peptide to the amino terminal end of the Rop protein (Rop(C) fusion peptide inhibitors

| Inhibitor | % inhibition in minimal media | % inhibition in rich media |
|---|---|---|
| pRop(C)1 | 87 | 47 |
| pRop(C)2 | 99 | 58 |
| pRop(C)3 | 85 | 54 |
| pRop(C)4 | 98 | 49 |
| pRop(C)5 | 95 | 54 |
| pRop(C)6 | 99 | 46 |
| pRop(C)7 | 91 | 59 |
| pRop(C)8 | 86 | 51 |
| pRop(C)9 | 93 | 57 |
| pRop(C)10 | 91 | 35 |

Isolation and Characterization of Inhibitor Peptides that are Fused at Their Amino Terminal End to the Carboxy Terminal End of the Rop Protein. Approximately 6000 peptides protected at their amino terminal end by Rop protein were screened using the grid-patching technique described in Example II, and 14 two day inhibitors were isolated. As observed for the Rop fusion peptides isolated using the p-Rop (C) vector, most of the inhibitor peptides isolated using the p(N)Rop- vector were inhibitory on rich media as well as minimal media. The inhibitors were verified as described hereinabove and subjected to growth rate analysis using p(N) Rop- as a control in order to determine their potency. As indicated in Table 16, the inhibitors inhibited the bacterial growth rate at levels that averaged 90% in minimal media and at levels that averaged 40% in rich media. The data in Table 16 is the average of duplicate experiments.

TABLE 16

Inhibitory effects of peptide inhibitors stabilized by fusing the amino terminal end of the peptide to the carboxy terminal end of the Rop protein (Rop(N) fusion peptide inhibitors)

| Inhibitor | % inhibition in minimal media | % inhibition in rich media |
|---|---|---|
| pRop(N)1 | 81 | 30 |
| pRop(N)2 | 96 | 53 |
| pRop(N)3 | 95 | 43 |
| pRop(N)4 | 92 | 38 |
| pRop(N)5 | 99 | 33 |
| pRop(N)6 | 93 | 38 |
| pRop(N)7 | 87 | 34 |
| pRop(N)8 | 91 | 44 |
| pRop(N)9 | 95 | 37 |
| pRop(N)10 | 96 | 40 |

Isolation and Characterization of Anchorless Inhibitor Peptides Containing Two Prolines at Both Their Amino Terminal and Carboxy Terminal Ends. Approximately 7500 peptides were screened using the grid-patching technique described in Example II, and 12 two day inhibitors were isolated. As indicated in Table 17, the top ten inhibitors inhibited the bacterial growth rate at levels that averaged 50% in minimal media. The inhibitory effects were determined as described in the text using pLAC11 as a control. The data in Table 17 is the average of duplicate experiments.

TABLE 17

Inhibitory effects of peptide inhibitors stabilized by two proline residues at both the amino and carboxy terminal ends of the peptide

| Inhibitor | % inhibition in minimal media |
|---|---|
| pPro1 | 50 |
| pPro2 | 49 |
| pPro3 | 50 |
| pPro4 | 59 |
| pPro5 | 52 |
| pPro6 | 93 |
| pPro7 | 54 |
| pPro8 | 42 |

TABLE 17-continued

Inhibitory effects of peptide inhibitors stabilized by two proline residues at both the amino and carboxy terminal ends of the peptide

| Inhibitor | % inhibition in minimal media |
|---|---|
| pPro9 | 41 |
| pPro10 | 42 |

Sequence analysis of the coding regions for the top ten inhibitors is shown in Table 19. The landmark Bgl II and EcoR I restriction sites for the insert region are underlined, as are the proline residues.

Since the ends of the oligonucleotide from which these inhibitors were constructed contained Bgl II and EcoRI I restriction sites, the oligonucleotide was not gel isolated when the libraries were prepared in order to maximize the oligonucleotide yields. Because of this, three of the inhibitory clones, pPro2, Ppro5, and pPro6 were found to contain deletions in the randomized portion of the oligonucleotide.

TABLE 18

Sequence analysis of the insert region from the proline peptides

```
pPro1 - 21 aa
AGA TCT ATG CCG CCG ATT CTA TGG GGC GAA GCG AGA AAG CGC TTG TGG GGT GGG GAT CAT ACA CCG    (SEQ ID NO: 69)
        M   P   P   I   L   W   G   E   A   R   K   R   L   W   G   D   H   T   P      (SEQ ID NO: 70)
CCG TAA TAA GAA TTC
 P   *   * pPro2 - 27 aa
AGA TCT ATG CCG CCG CCG TTG GAT ATT GTG TCG GGT ATT GAG GTA GGG GGG CAT TTG TGG TGC CGC    (SEQ ID NO: 71)
        M   P   P   P   L   D   I   V   S   G   I   E   V   G   G   H   L   W   C   R      (SEQ ID NO: 72)
CGT ATT AAG AAT TCT CAT GTT TGA
 R   I   K   N   S   H   V   * pPro3 - 8 aa
AGA TCT ATG CCG CCG GAC AAT CCG GTC CTG TGA TGA AGC GGA GGT CGA CCA AGG GGA TAT CAG CCG    (SEQ ID NO: 73)
        M   P   P   D   N   P   V   L   *                                                  (SEQ ID NO: 74)
CCG TAA TAA GAA TTC pPro4 - 9 aa
AGA TCT ATG CCG CCG CTA TTG GAC GGA GAT GAC AAA TAG ATA TAT GCG TGG TTG TTT TTC TGT CCG    (SEQ ID NO: 75)
        M   P   P   L   L   D   G   D   D   K   *                                          (SEQ ID NO: 76)
CCG TAA TAA GAA TTC pPro5 - 10 aa
AGA TCT ATG CCG CCG AGG TGG AAG ATG TTG ATA AGA CAG TGA CAG ATG CGT TCC ATT ACT CCC GCC    (SEQ ID NO: 77)
        M   P   P   R   W   K   M   L   I   R   Q   *                                      (SEQ ID NO: 78)
GTA ATA AGA ATT C pPro6 - 7 aa
AGA TCT ATG ATG AGA GTA GCG CCG CCG TAA TAA GAA TTC                                        (SEQ ID NO: 79)
        M   M   R   V   A   P   P   *   *                                                  (SEQ ID NO: 80)

pPro7 - 14 aa
AGA TCT ATG CCG CCG TTG CGC GGG GCA TGC GAT GTA TAT GGG GTA AAT TGA ATG TCT TGT GGG CCG    (SEQ ID NO: 81)
        M   P   P   L   R   G   A   C   D   V   Y   G   V   N   *                          (SEQ ID NO: 82)
CCG TAA TAA GAA TTC pPro8 - 21 aa
AGA TCT ATG CCG CCG GGG AGA GGG GAA GCG GTG GGA GTG ACA TGC TTG AGC GCG AAC GTG TAC CCG    (SEQ ID NO: 83)
        M   P   P   G   R   G   E   A   V   G   V   T   C   L   S   A   N   V   Y   P      (SEQ ID NO: 84)
CCG TAA TAA GAA TTC
 P   *   * pPro9 - 21 aa
AGA TCT ATG CCG CCG GGA AGG GTA GTG TTC TTT GTC GCT ATC TTT GTT TCC GCA ATA TGC CTC CCG    (SEQ ID NO: 85)
        M   P   P   G   R   V   V   F   F   V   A   I   F   V   S   A   I   C   L   P      (SEQ ID NO: 86)
CCG TAA TAA GAA TTC
 P   *   * pPro10 - 21 aa
AGA TCT ATG CCG CCG AGG TTC GCT CAT GAG AGT GTT AAA GGG CTG GGG GAC GTT ACA AAA GCT CCG    (SEQ ID NO: 87)
```

TABLE 18-continued

Sequence analysis of the insert region from the proline peptides

| | | M | P | P | R | F | A | H | E | S | V | K | G | L | G | D | V | T | K | A | P | (SEQ ID NO: 88) |
|---|---|---|---|---|---|---|---|---|---|---|---|---|---|---|---|---|---|---|---|---|---|---|
| CCG | TAA | TAA | GAA | TTC | | | | | | | | | | | | | | | | | | |
| P | * | * | | | | | | | | | | | | | | | | | | | | |

All the inhibitors were found to contain two proline residues at either their amino or carboxy termini as expected. Four inhibitors contained two proline residues at both their amino and carboxy termini, five inhibitors contained two proline residues at only their amino termini, and one inhibitor contained two proline residues at only its carboxy terminus.

Isolation and Characterization of Anchorless Hydrophilic Inhibitor Peptides Stabilized by an α-Helical Motif. Approximately 12,000 peptides were screened using the grid-patching technique and 5 two-day inhibitors were isolated. The inhibitors were verified as already described for the Rop-peptide fusion studies and subjected to growth rate analysis using pLAC11 as a control in order to determine their potency. As indicated in Table 19, the inhibitor peptides inhibited the bacterial growth rate at levels that averaged 50% in minimal media. The averaged values of two independent determinations are shown.

Sequence analysis of the coding regions for the 5 inhibitors is shown in Table 20. The landmark Bgl II and EcoR I restriction sites for the insert region are underlined. Since the ends of the oligonucleotide from which these inhibitors were constructed contained these restriction sites, the oligonucleotide was not gel isolated when the libraries were prepared in order to maximize the oligonucleotide yields. Because of this, two of the inhibitory clones, pHelix2 and pHelix3, were found to contain deletions in the randomized portion of the oligonucleotide. The predicted α-helical content of these peptides is indicated in Table 20 according to the secondary structure prediction rules of Garnier, Osguthorpe, and Robson (J. Garnier et al., J. Mol. Biol. 120: 97-120 (1978)) prediction rules.

TABLE 20

Sequence analysis of the insert region from the hydrophilic α-helical peptides

```
pHelix1 - 18 aa, 83% α-helical
AGA TCT ATG CAT GAC GAA CAA GAG GAG GAG CAC AAT AAA AAG GAT AAC GAA AAA GAA CAC TAA TAA    (SEQ ID NO: 89)
        M   H   D   E   Q   E   E   E   H   N   K   K   D   N   E   K   E   H   *   *      (SEQ ID NO: 90)
GAA TTC pHelix2 - 22 aa 68% α-helical
AGA TCT ATG CAG CAG GAG CAC GAG CAA GGC AGG ATG AGC AAG AGG ATG AAG AAT AAT AAG AAT TCT    (SEQ ID NO: 91)
        M   Q   Q   E   H   E   Q   G   R   M   S   K   R   M   K   N   N   K   N   S      (SEQ ID NO: 92)
CAT GTT TGA
 H   V   * pHelix3 - 22 aa, 55% α-helical
AGA TCT ATG AAC CAT CAT AAT GAG GCC ATG ATC AAC ACA ATG AAA ACG AGG AAT AAT AAG AAT TCT    (SEQ ID NO: 93)
        M   N   H   H   N   E   A   M   I   N   T   M   K   T   R   N   N   K   N   S      (SEQ ID NO: 94)
CAT GTT TGA
 H   V   * pHelix4 - 18 aa, 17% α-helical
AGA TCT ATG AAC GAC GAC AAT CAG CAA GAG GAT AAT CAT GAT CAG CAT AAG GAT AAC AAA TAA TAA    (SEQ ID NO: 95)
    M   N   D   D   N   Q   Q   E   D   N   H   D   Q   H   K   D   N   K   *   *          (SEQ ID NO: 96)
GAA TTC pHelix5 - 18 aa, 50% α-helical
AGA TCT ATG CAA GAG CAG GAT CAG CAT AAT GAT AAC CAT CAC GAG GAT AAA CAT AAG AAG TAA TAA    (SEQ ID NO: 97)
        M   Q   E   Q   D   Q   H   N   D   N   H   H   E   D   K   H   K   K   *   *      (SEQ ID NO: 98)
GAA TTC
```

TABLE 19

Inhibitor effects of the hydrophilic α-helical peptides

| Inhibitor | % inhibition in minimal media |
|---|---|
| pHelix1 | 67 |
| pHelix2 | 46 |
| pHelix3 | 48 |
| pHelix4 | 45 |
| pHelix5 | 42 |

According to Garnier, Osguthorpe, and Robson secondary structure prediction, all of the encoded peptides are expected to be largely α-helical except for pHelix4. Interestingly, pHelix1, which had the highest degree of α-helical content, was also the most potent inhibitory peptide that was isolated in this study.

Isolation and Characterization of Anchorless Inhibitor Peptides Stabilized by an Opposite Charge Ending Motif. Approximately 20,000 peptides were screened using the grid-patching technique and 6 two day inhibitors were isolated. The inhibitors were verified as already described for the Rop-peptide fusion studies and subjected to growth rate analysis using pLAC11 as a control in order to determine their potency. As indicated in Table 21, the inhibitor peptides inhibited the bacterial growth rate at levels that averaged 50% in minimal media. The averaged values of two independent determinations are shown.

TABLE 21

Inhibitory effects of peptide inhibitors that are stabilized by the opposite charge ending motif

| Inhibitor | % inhibition in minimal media |
|---|---|
| p +/− 1 | 41 |
| p +/− 2 | 43 |
| p +/− 3 | 48 |
| p +/− 4 | 60 |
| p +/− 5 | 54 |
| p +/− 6 | 85 |

Sequence analysis of the coding regions for the six inhibitors is shown in Table 22. The landmark Bgl II and EcoR I restriction sites for the insert region are underlined. With the exception of p+/−4, which was terminated prematurely, the coding regions for the inhibitors were as expected based on the motif that was used to generate the peptide libraries.

Discussion

In Example II, where fully randomized peptides were screened for inhibitory effect, only three peptides (one "anchorless" and two unanticipated Rop fusions resulting from deletion) were identified out of 20,000 potential candidates as a potent (i.e., two day) inhibitor of *E. coli* bacteria. Using a biased synthesis as in this Example, it was possible to significantly increase the frequency of isolating potent growth inhibitors (see Table 23).

TABLE 23

Summary of the frequency at which the different types of inhibitor peptides can be isolated

| Type of inhibitor peptide | Frequency at which a two day inhibitor peptide can be isolated | Reference |
|---|---|---|
| anchorless | 1 in 20,000 | Example II |
| protected at the C-terminal end via Rop | 1 in 625 | This example |

TABLE 22

Sequence analysis of the insert region from the opposite charge ending peptides

```
p +/- 1 - 25 aa
AGA TCT ATG GAA GAC GAA GAC GAG GGT GCG TCA GCG TGG GGA GCA GAA CTT TGG TCG TGG CAG TCG   (SEQ ID NO: 99)
        M   E   D   E   D   E   G   A   S   A   W   G   A   E   L   W   S   W   Q   S      (SEQ ID NO: 100)
GTG CGT AAA CGT AAA TAA TAA GAA TTC
 V   R   K   R   K   *   * p +/- 2 - 25 aa
AGA TCT ATG GAA GAC GAA GAC GGT CTA GGC ATG GGG GGT GGG TTG GTC AGG CTC ACT TTA TTA TTC   (SEQ ID NO: 101)
        M   E   D   E   D   G   L   G   M   G   G   G   L   V   R   L   T   L   L   F      (SEQ ID NO: 102)
TTC CGT AAA CGT AAA TAA TAA GAA TTC
 F   R   K   R   K   *   * p +/- 3 - 25 aa
AGA TCT ATG GAA GAC GAA GAC GGG GAG AGG ATC CAG GGG GCC CGC TGT CCA GTA GCG CTG GTA GAT   (SEQ ID NO: 103)
        M   E   D   E   D   G   E   R   I   Q   G   A   R   C   P   V   A   L   V   D      (SEQ ID NO: 104)
AGA CGT AAA CGT AAA TAA TAA GAA TTC
 R   R   K   R   K   *   * p +/- 4 - 11 aa
AGA TCT ATG GAA GAC GAA GAC GAC AGG GGG CGT GGG GGG TAG CTT TAA GTT GCG CTA AGT TGC GAG   (SEQ ID NO: 106)
        M   E   D   E   D   D   R   G   R   G   R   *                                      (SEQ ID NO: 105)
ATA CGT AAA CGT AAA TAA TAA GAA TTC p +/- 5 -25 aa
AGA TCT ATG GAA GAC GAA GAC GGG GGG GCC GGG AGG AGG GCC TGT CTT TGT TCC GCG CTT GTT GGG   (SEQ ID NO: 107)
        M   E   D   E   D   G   G   A   G   R   R   A   C   L   C   S   A   L   V   G      (SEQ ID NO: 108)
GAA CGT AAA CGT AAA TAA TAA GAA TTC
 E   R   K   R   K   *   * p +/-6 - 25 aa
AGA TCT ATG GAA GAC GAA GAC AAG CGT CGC GAG AGG AGT GCA AAA GGG CGT CAT GTC GGT CGG TCG   (SEQ ID NO: 109)
        M   E   D   E   D   K   R   R   E   R   S   A   K   G   R   H   V   G   R   S      (SEQ ID NO: 110)
ATG CGT AAA CGT AAA TAA GAC TGT
 M   R   K   R   K   *
```

TABLE 23-continued

Summary of the frequency at which the different types of inhibitor peptides can be isolated

| Type of inhibitor peptide | Frequency at which a two day inhibitor peptide can be isolated | Reference |
|---|---|---|
| protected at the N-terminal end via Rop | 1 in 429 | This example |
| protected at both the C-terminal and N-terminal end via two prolines | 1 in 625 | This example |
| protected with an α-helix structural motif | 1 in 2,400 | This example |
| protected with an opposite charge ending motif | 1 in 3,333 | This example |

Many more aminopeptidases have been identified than carboxypeptidases in both prokaryotic and eukaryotic cells (J. Bai, et al., Pharm. Res. 9: 969-978 (1992); J. Brownlees et al., J. Neurochem. 60:793-803 (1993); C. Miller, In *Escherichia coli* and *Salmonella typhimurium* cellular and molecular biology, 2nd edition (Neidhardt, F. C. ed.), ASM Press, Washington, D.C. 1:938-954 (1996)). In the Rop fusion studies, it might have therefore been expected that stabilizing the amino terminal end of the peptide would have been more effective at preventing the action of exopeptidases than stabilizing the carboxy end of the peptides. Surprisingly, it was found that stabilizing either end of the peptide caused about the same effect.

Peptides could also be stabilized by the addition of two proline residues at the amino and/or carboxy termini, the incorporation pf opposite charge ending amino acids at the amino and carboxy termini, or the use of helix-generating hydrophilic amino acids. As shown in Table 23, the frequency at which potent inhibitor peptides could be isolated increased significantly over that of the anchorless peptides characterized in Example II.

These findings can be directly implemented to design more effective peptide drugs that are resistant to degradation by peptidases. In this example, several strategies were shown to stabilize peptides in a bacterial host. Because the aminopeptidases and carboxypeptidases that have been characterized in prokaryotic and eukaryotic systems appear to function quite similarly (C. Miller, In *Escherichia coli* and *Salmonella typhimurium* cellular and molecular biology, 2nd edition (Neidhardt, F. C. ed.), ASM Press, Washington, D.C. 1:938-954 (1996); N. Rawlings et al., Biochem J. 290: 205-218 (1993)), the incorporation of on or more of these motifs into new or known peptide drugs should slow or prevent the action of exopeptidases in a eukaryotic host cell as well.

Example IV

Confirmation of the Stabilizing Effects of Proline Residues using an In Vitro System To extend the in vivo studies described above, an in vitro system for directly assessing peptide stability was developed. In the in vitro system, peptides to be tested were mixed with a cellular extract containing the proteases and peptidases present in a particular cell type. To validate this approach, the stability or half-life of a randomized biotinylated peptide initially was measured using both wild-type bacterial extracts and bacterial extracts that were deficient in known proteases or peptidases.

Material and Methods

Bacterial strains. The bacterial strains used in this study are shown in Table 24. MG1655 clpP::cam was constructed by transducing MG1655 to chloramphenicol resistance using a P1 lysate that was prepared from SG22098.

TABLE 24

Bacterial strains

| Strain | Genotype | Reference |
|---|---|---|
| *E. coli* strains | | |
| MG1655 | F-λ- | Guyer, M. S. et al., 1980* |
| MG1655 lon::Tn10 | F-λ-lon::Tn10 | Carol Gross, University of California, San Francisco |
| MG1655 clpP::cam | F-λ-clpP::cam | This study |
| SG22098 | F-λ-araD139 Δ(lac)U169 rpsL150 thi flbB5301 deoC7 ptsF25 clpP::cam | Michael Maurizi, National Cancer Institute |
| *S. typhimurium* LT2 strains | | |
| TN1379 | leuBCD485 | Charles Miller, University of Illinois |
| TN1727 | leuBCD485 pepA16 pepB11 pepN90 pepP1 pepQ1 pepT1 ΔsupQ302(proAB pepD) optA1 zxx848::Tn5 dcp-1 zxx845::Tn10 | Charles Miller, University of Illinois |

*Guyer, M. S. et al., Cold Spring Harbor Symp. Quant. Biol. 45: 135-140 (1980).

Media. Bacterial cells were grown in LB media; yeast cells were grown in 1.0% yeast extract, 2.0% peptone, 2.0% glucose; human HeLa cells (ATCC CCL-2) and colon CCD-18Co cells (ATCC CRL-1459) were grown in Minimal Essential Medium Eagle (ATCC 30-2003) with Earle's balanced salt solution, 0.1 mM non-essential amino acids, 2.0 mM L-glutamine, 1.0 mM sodium pyruvate, 1.5 g/L NaHCO$_3$, and 10% fetal bovine serum; and human small intestine FHs74 Int cells (ATCC CCL-241) were grown in Hybri-Care media (ATCC 46-X) with 1.5 g/L NaHCO$_3$ and 10% fetal bovine serum.

Preparation of the extracts. For bacteria and yeast, 500 mL of cells were grown to an OD$_{550}$ of 0.5, centrifuged, washed twice with T$_{10}$E$_{0.1}$ (10.0 mM Tris; pH 8.0, 0.1 mM EDTA; pH 8.0) and resuspended in 2.0 mL of 10.0 mM Tris; pH 8.0. For human cells, 10-50 75 cm$^2$ T flasks were seeded and allowed to grow to 95% confluency in a 37° C. incubator with 5% CO$_2$ atmosphere. Each flask was then washed with HBSS (0.4 g/L KCl, 0.06 g/L KH$_2$PO$_4$, 8 g/L NaCl, 0.35 g/L NaHCO$_3$, 0.048 g/L $Na_2HPO_4$, 1.0 g/L Glucose) that contained 0.125 mM EDTA; pH 8.0. To liberate the cells, the flasks were treated with 1.5 mL of HBSS that contained 0.25% trypsin and 0.5 mM EDTA; pH 8.0. The trypsin was neutralized by adding 5 mL of media with 10% fetal bovine serum to each flask. The cells were centrifuged, washed with HBSS that contained 0.125 mM EDTA; pH 8.0, washed twice with HBSS lacking glucose and ETDA, and resuspended in 2.0 mL of 10.0 mM Tris; pH 8.0. All cell suspensions were lysed with three passes at 15,000 psi in a French Pressure cell maintained at 4° C. The lysates were then centrifuged at 15,000 rpm, 4° C., for 10 minutes to pellet debris and unlysed cells and the supernatant was saved as the cell extract. To prepare rat serum, one 300 g Sprague Dawley rat was euthanized with $CO_2$ and a heart puncture was performed to draw the blood which was immediately transferred to a tube and centrifuged at 4° C., 10,000 rpm, for 10 minutes. The cleared serum was removed with a pipette except for 1 cm of serum at the interface with the blood cell pellet.

Peptide synthesis. The following randomized biotinylated peptides were synthesized by Sigma Genosys (The Woodlands, Texas):

| | |
|---|---|
| Unprotected | XXXXXX[KBtn]XXXXXA |
| P at both ends | PXXXX[KBtn]XXXXP |
| PP at both ends | PPXXXX[KBtn]XXXXPP |
| APP at both ends | APPXXXX[KBtn]XXXXPPA |
| APP amino | APPXXXX[K-Btn]XXXXA |
| APP carboxyl | AXXXX[K-Btn]XXXXPPA |
| Acetylated | (Ac)AXXXXX[KBtn]XXXXXA |
| Amidated | XXXXXX[KBtn]XXXXXA(NH$_2$) |
| Cyclized | CXXXXXX[KBtn]XXXXXXC | where A denotes the L-amino acid alanine, P denotes the L-amino acid proline, X denotes an equimolar mixture of the 20 natural L-amino acids except for proline, and KBtn denotes the L-amino acid lysine to which biotin has been attached.

To ensure that the length of the randomized portion of the peptides did not affect the degradation profiles, we also tested the unprotected peptides XXXx[KBtn]XXXXA and AXXXX[KBtn]XXXXA. Their half-lives were determined to be within 5% of the XXXXXX[KBtn]XXXXXA peptide which was used as the control for these studies.

In vitro degradation assay. All extracts were used at a final concentration of 10 mg/mL, except for the *S. typhimurium* extracts, which were used at a final concentration of 25 mg/mL. The cell extract (50 µL) was mixed with 50 µL of a peptide at a concentration of 1 mg/mL in 10 mM Tris; pH 8.0 and incubated at 37° C. Aliquots were removed (10 µL) at 30, 60, 90, or 120 minute intervals, placed into 90 µL of SDS-PAGE gradient gel buffer, boiled for 5 minutes, and electrophoresed through a 10-20% tricine gradient gel. The gel was blotted onto a nitrocellulose membrane and the resulting Western blot was treated with NeutrAvidin Horseradish Peroxidase Conjugate and SuperSignal West Dura Extended Duration Chemiluminescent Substrate (Pierce, Rockford, Ill.). The biotinylated peptides were then visualized by exposing the blots to autoradiography film and the resulting bands were quantified using the AlphaEase 5.5 Densitometry Program from Alpha Innotech, San Leandro, Calif.

Results

The proteases and peptidases have been well characterized in *E. coli* and *S. typhimurium*. In *E. coli*, the two main proteases that have been shown to have a role in peptide degradation are Lon and ClpP, which are encoded respectively by the lon and clpP genes. In *S. typhimurium*, numerous peptidases have been identified, and strains have been constructed that delete several of the peptidases. Using extracts prepared from *E. coli* strains that contained lon or clpP deletions and a *S. typhimurium* strain in which nine peptidase genes were deleted, half-lives were determined for the unprotected randomized biotinylated control peptide. As shown in Table 25, deletion of the Lon protease caused the peptide's half-life to increase by 6.5 fold, deletion of the ClpP protease caused the peptide's half-life to increase by 1.8 fold, and deletion of multiple peptidases caused the peptide's half-life to increase by 7.1 fold. These results prove that the in vitro system provides an accurate method by which to assess peptide stability.

TABLE 25

Peptide degradation in protease and peptidase deficient extracts.

| Strain from which extract was prepared* | Peptide half-life in minutes |
|---|---|
| MG1655 | 44.9 |
| MG1655 lon::Tn10 | 290.6 |
| MG1655 clpP::cam | 82.5 |
| TN1379 | 42.0 |
| TN1379 dcp-1 optA1 pepA16 pepB11 ΔpepD pepN90 pepP1 pepQ1 pepT1 | 298.5 |

*Because of the decreased potency of *S. typhimurium* extracts relative to *E. coli* extracts, the *S. typhimurium* extracts were used at a concentration of 25 mg/mL.

With the system validated, the stabilizing effects of proline residues were analyzed. Three randomized biotinylated peptides were tested using extracts prepared from bacterial (wild-type *E. coli*), Baker's yeast (wild-type *Saccharomyces cerevisiae*), human (HeLa) cells, human intestine and colon cells, and rat serum. One randomized peptide was unprotected, while the other two peptides were stabilized on both the N- and C-termini with a Pro (P) motif, a Pro-Pro motif (PP), or an Ala-Pro-Pro motif (APP). The results are shown in the Table 26.

TABLE 26

The effect of proline-containing stabilizing groups on peptide degradation

| | Peptide half-lives in minutes | | | |
|---|---|---|---|---|
| Extract | Unprotected peptide | Peptide protected at both ends by P | Peptide protected at both ends by PP | Peptide protected at both ends by APP |
| E. coli | 44.9 | 38.2 | 51.1 | 69.8 |
| S. cereviseae | 23.3 | 44.4 | 99.0 | 156.0 |
| Human HeLa | 90.8 | ND | 423.4 | 1,054.3 |
| Human Intestine | 121.6 | 99.2 | 166.3 | 171.8 |
| Human Colon | 58.1 | 64.5 | 76.1 | 109.2 |
| Rat serum | 54.1 | 80.7 | 85.3 | 154.5 |

ND: not determined

As the data indicate, the APP motif offered significantly more protection than the PP motif, which provided better protection than the P motif.

Table 27 shows the results of degradation studies on peptides that contain the APP motif at either or both of the amino or carboxyl termini.

TABLE 27

The effect of APP stabilizing groups on peptide degradation

| | Peptide half-lives in minutes | | | |
|---|---|---|---|---|
| Extract | Unprotected | APP at both ends | APP Amino terminus | APP Carboxyl terminus |
| E. coli | 44.9 | 69.8 | 99.6 | 54.6 |
| S. cereviseae | 23.3 | 156.0 | 86.0 | 44.4 |
| Human Intestine | 121.6 | 171.8 | 200.7 | 99.0 |
| Human Colon | 58.1 | 109.2 | 144.0 | 95.1 |
| Rat serum | 54.1 | 154.5 | 165.3 | 121.2 |

The data show that APP at only the amino terminus offers slightly better protection than APP at both termini, and that APP at only the amino terminus offers significantly better protection than APP at only the carboxyl terminus.

Table 28 shows the results of degradation studies on peptides that contain the APP motif at the N- or C-terminus compared to peptides that are acetylated at their amino terminus, amidated at their carboxyl terminus, or cyclized.

TABLE 28

The effect of APP stabilizing groups on peptide degradation in comparison to acetylation, amidation or cyclization.

| | Peptide half-lives in minutes | | | | | |
|---|---|---|---|---|---|---|
| Extract | Unprotected | APP Amino | Acetylated | APP Carboxyl | Amidated | Cyclized |
| E. coli | 44.9 | 99.6 | 34.9 | 54.6 | 46.7 | 52.3 |
| S. cereviseae | 23.3 | 86.0 | 44.2 | 44.4 | 73.9 | 145.0 |
| Rat serum | 54.1 | 165.3 | 67.3 | 121.2 | 75.7 | 217.2 |

The data clearly shows that APP at the amino terminus offers better protection than amidating the carboxyl terminus or acetylating the amino terminus, and is almost as good as cyclization.

Example V

Bioactivity of Natural Galanin, APP-Galanin, and APP-Galanin-PPA

Radio immunoassays (RIAs) were performed to determine the ability of galanin and its APP derivatives to displace radiolabeled galanin from its receptor. Binding (displacement) constants were then calculated from this data.

| Natural galanin | $K_i = 5.21 \times 10^{-9}$ |
|---|---|
| APP-galanin | $K_i = 6.42 \times 10^{-9}$ |
| APP-galanin-PPA | $K_i = 9.46 \times 10^{-9}$ |

As the data shows the binding constants for the APP derivatives were in the same range as natural galanin and thus these compounds were able to interact with the galanin receptor in a manner similar to natural galanin.

Example VI

In vivo Glucagon, APP-Glucagon and APP-Glucagon-PPA Degradation

A catheter was placed in the right jugular vein of six Male Sprague-Dawley rats for dosing and sampling. Two rats were used for each of the three compounds that were tested. The rats received an intravenous bolus injection of the peptide, and serial blood samples (0.3 ml) were obtained. The glucagon was extracted from plasma by organic protein precipitation and quantified by electrospray LC-MS.

The presence of the APP motif affected both the half-life of glucagon as well as the rate at which it is cleared from the body. The data (Table 29) suggests that a significant portion of the glucagon harboring the APP motif becomes sequestered and thus is much more resistant to degradation. It should be noted that significantly more APP-glucagon-PPA and APP-glucagon is present at 20 and 60 minutes than would be predicted due to its half-life.

TABLE 29

| Peptide | Half-life in minutes | Percent remaining after 20 minutes | Percent remaining after 60 minutes |
|---|---|---|---|
| Glucagon | 1.031 | 0.2 | 0.0 |
| APP-Glucagon-PPA | 1.555 | 3.0 | ND |
| APP-Glucagon | 2.253 | 7.3 | 8.6 |

ND (not determined)

Sequence Listing Free Text

SEQ ID NO:2
peptide sequence having opposite charge ending motif
SEQ ID NOs:3, 4
stabilized angiotensin
SEQ ID NOs:6-19, 24-28, 55-58, 60, 62, 64, 66, 68
primer
SEQ ID NOs:20-22
primer fragment
SEQ ID NOs:23, 59, 61, 63, 65, 67
randomized oligonucleotide
SEQ ID NOs:29-33
antisense oligonucleotide
SEQ ID NOs:34, 36, 39, 40, 43, 45, 46, 48, 51, 52, 70, 72, 74, 76, 78, 80, 82, 84, 86, 88, 90, 92, 94, 96, 98, 100, 102, 104, 105, 108, 110
stabilized peptide
SEQ ID NOs:35, 37, 38, 41, 42, 44, 47, 49, 50, 53, 69, 71, 73, 75, 77, 79, 81, 83, 85, 87, 89, 91, 93, 95, 97, 99, 101, 103, 106, 107, 109 nucleic acid encoding stabilized peptide
SEQ ID NO:54
N-terminal protective sequence
SEQ ID NO:111-115
α-helical moieties The foregoing detailed description and examples have been given for clarity of understanding only. No unnecessary limitations are to be understood therefrom. The invention is not limited to the exact details shown and described, for variations obvious to one skilled in the art will be included within the invention defined by the claim.

What is claimed is:

1. An isolated nucleic acid encoding a stabilized polypeptide, wherein said stabilized polypeptide comprises a bioactive peptide and a first stabilizing group covalently linked to a terminus of said bioactive peptide, and a second stabilizing group covalently linked to the other terminus of said bioactive peptide, wherein said first stabilizing group is heterologous to the bioactive peptide and lacks the capacity to participate in the formation of an intramolecular disulfide bond within the polypeptide, and wherein said second stabilizing group is $Xaa_n$-Pro-, $Xaa_n$-Pro- Pro-, Pro-$Xaa_n$ or -Pro-Pro-$Xaa_n$, wherein Xaa is any amino acid and n=1 or 2.

2. The isolated nucleic acid of claim 1, wherein at least one Xaa is Ala.

3. A method of making a stabilized polypeptide, said method comprising:
   a) providing host cells transformed with the nucleic acid of claim 1;
   b) expressing said stabilized polypeptide encoded by said nucleic acid; and
   c) recovering said stabilized polypeptide.

4. The method of claim 3, wherein said host cells are bacteria.

5. The method of claim 3, wherein said host cells are eukaryotic host cells.

6. The method of claim 3, wherein the second stabilizing group is heterologous to the bioactive peptide.

7. The method of claim 6, wherein said first and said second heterologous stabilizing groups are the same.

8. A method of making a polypeptide comprising:
   providing a bacteriophage that comprises the nucleic acid of claim 1; and
   culturing said bacteriophage under conditions to cause the bacteriophage to express the polypeptide encoded by said nucleic acid and display it on the surface of the bacteriophage.

9. The method of claim 8, wherein the stabilizing group is covalently linked to the N-terminus of the bioactive peptide.

10. The method of claim 8, wherein the stabilizing group is covalently linked to the C-terminus of the bioactive peptide.

11. The method of claim 8 further comprising cleaving the polypeptide from the host cell surface to yield a stabilized bioactive peptide comprising the bioactive peptide and the stabilizing group.

12. A vector comprising an expression control sequence operably linked to a nucleic acid sequence encoding a stabilized polypeptide, wherein said stabilized polypeptide comprises a bioactive peptide and a first stabilizing group covalently linked to one of said bioactive peptide's termini, wherein said first stabilizing group is $Xaa_n$-Pro-, $Xaa_n$-Pro- Pro-, -Pro-$Xaa_n$ or -Pro-Pro-$Xaa_n$, wherein Xaa is any amino acid and wherein n=1 or 2.

13. The vector of claim 12, wherein said stabilized polypeptide further comprises a second stabilizing group covalently linked to the other terminus of said bioactive peptide, wherein the second stabilizing group is heterologous to the bioactive peptide.

14. The vector of claim 12, wherein said vector further comprises a tightly regulable expression control sequence operably linked to said nucleic acid sequence encoding said stabilized polypeptide.

15. The vector of claim 14, wherein said tightly regulable expression control sequence is from a wild-type *E. coli* lac promoter/operator region.

16. The vector of claim 14, wherein said expression control sequence comprises the auxiliary operator O3, the CAP binding region, the −35 promoter site, the −10 promoter site, the operator O1, lacZ Shine-Dalgarno sequence, and a spacer sequence between the end of the Shine-Dalgarno sequence and the start codon of said nucleic acid sequence.

17. The vector of claim 16, wherein said spacer region is 5 to 10 nucleotides in length.

18. The vector of claim 12, wherein said vector is pLAC11 having ATCC Accession No. 207108.

19. An isolated nucleic acid encoding a stabilized polypeptide, wherein said stabilized polypeptide comprises a bioactive peptide and a stabilizing group covalently lined to one or both of said bioactive peptide's termini, wherein said stabilizing group is $Xaa_n$-Pro-Pro-, or -Pro-Pro-$Xaa_n$, wherein Xaa is any amino acid and n=1 or 2.

20. The nucleic acid of claim 19 wherein a stabilizing group is covalently linked to each of said bioactive peptide's N-terminus and C-terminus.

21. The nucleic acid of claim 20 wherein the stabilizing group covalently lined to the N-terminus and the stabilizing group covalently linked to the C-terminus of said bioactive peptide are heterologous.

22. The nucleic acid of claim 19 wherein said bioactive peptide is selected from the group consisting of insulin, glucagon, calcitonin, somatostatin, gonadotrophin and secretin.

* * * * *